(12) United States Patent
Jacobson et al.

(10) Patent No.: US 6,716,841 B2
(45) Date of Patent: Apr. 6, 2004

(54) NITROGEN CONTAINING HETEROBICYCLES AS FACTOR XA INHIBITORS

(75) Inventors: Irina C. Jacobson, Sammamish, WA (US); Mimi L. Quan, Newark, DE (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 12 days.

(21) Appl. No.: 10/205,792

(22) Filed: Jul. 26, 2002

(65) Prior Publication Data

US 2003/0096820 A1 May 22, 2003

Related U.S. Application Data

(62) Division of application No. 09/615,465, filed on Jul. 13, 2000, now Pat. No. 6,429,205.
(60) Provisional application No. 60/144,344, filed on Jul. 16, 1999.

(51) Int. Cl.[7] .................. A61K 31/423; A61K 31/4155; C07D 413/14; C07D 403/02
(52) U.S. Cl. .................... 514/235.2; 514/248; 514/259; 514/300; 514/301; 514/302; 514/303; 514/310; 514/359; 514/363; 514/373; 514/379; 514/406; 544/137; 544/140; 544/235; 544/284; 546/112; 546/113; 546/114; 546/115; 546/118; 546/143; 548/138; 548/212; 548/241; 548/255; 548/264.6; 548/362.1; 548/362.5; 548/374.1
(58) Field of Search ............................. 544/137, 140, 544/235, 284; 546/112–115, 118, 143; 548/138, 212, 241, 255, 264.4, 362.1, 362.5, 374.1; 514/235.2, 379, 406

(56) References Cited

FOREIGN PATENT DOCUMENTS

| WO | WO 9723212 | 7/1997 |
|---|---|---|
| WO | WO 9828269 | 7/1998 |
| WO | WO 9828282 | 7/1998 |
| WO | WO 9857951 | 12/1998 |
| WO | WO 9867937 | 12/1998 |
| WO | WO 9932454 | 7/1999 |

*Primary Examiner*—Fiona T. Powers
(74) *Attorney, Agent, or Firm*—David H. Vance; Jing S. Belfield

(57) ABSTRACT

This invention relates generally to nitrogen containing heterobicycles of formulas A and B:

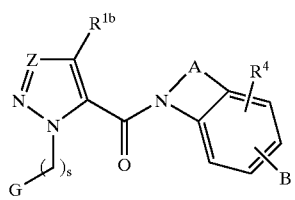

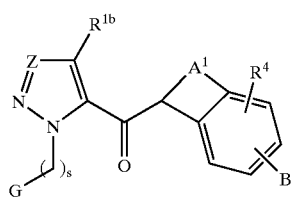

which are inhibitors of trypsin-like serine protease enzymes, especially factor Xa, pharmaceutical compositions containing the same, and methods of using the same as anticoagulant agents for treatment and prevention of thromboembolic disorders.

18 Claims, No Drawings

NITROGEN CONTAINING HETEROBICYCLES AS FACTOR Xa INHIBITORS

CROSS-REFERENCE TO RELATED APPLICATIONS

This application is a divisional application of U.S. application Ser. No. 09/615,465, filed Jul. 13, 2000, Now U.S. Pat. No. 6,429,205, which claims the priority benefit of U.S. Provisional Application No. 60/144,344, filed Jul. 16, 1999, all of which are expressly incorporated fully herein by reference.

FIELD OF THE INVENTION

This invention relates generally to nitrogen containing heterobicycles, which are inhibitors of trypsin-like serine protease enzymes, especially factor Xa, pharmaceutical compositions containing the same, and methods of using the same as anticoagulant agents for treatment and prevention of thromboembolic disorders.

BACKGROUND OF THE INVENTION

WO98/28269 describes factor Xa inhibitors of the formula:

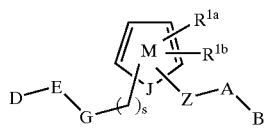

wherein ring M contains, in addition to J, 0–3 N atoms, J is N or NH, and D is substituted meta or para to G on E. However, WO98/28269 does not disclose compounds containing heterobicycles like those of the present invention.

WO98/57951 describes factor Xa inhibitors of the formula:

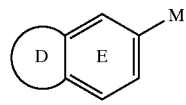

wherein ring D is selected from —CH$_2$N=CH—, —CH$_2$CH$_2$N=CH—, a 5–6 membered aromatic system containing from 0–2 heteroatoms selected from the group N, O, and S, ring E contains 0–2 N atom and M is a variety of rings including pyrazole and triazole. WO98/57951 does not, however, disclose compounds containing heterobicycles like those of the present invention.

WO98/57937 describes factor Xa inhibitors of the formula:

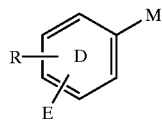

wherein ring D is phenyl or pyridyl and M is a variety of rings including pyrazole and triazole. However, WO98/57937 does not disclose compounds containing heterobicycles like those of the present invention.

PCT/US98/26427 describes factor Xa inhibitors of the formula:

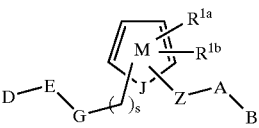

wherein ring M contains, in addition to J, 0–3 N atoms and J is N or NH and D is substituted ortho to G on E. However, PCT/US98/26427 does not disclose compounds containing heterobicycles like those of the present invention.

Activated factor Xa, whose major practical role is the generation of thrombin by the limited proteolysis of prothrombin, holds a central position that links the intrinsic and extrinsic activation mechanisms in the final common pathway of blood coagulation. The generation of thrombin, the final serine protease in the pathway to generate a fibrin clot, from its precursor is amplified by formation of prothrombinase complex (factor Xa, factor V, Ca$^{2+}$ and phospholipid). Since it is calculated that one molecule of factor Xa can generate 138 molecules of thrombin (Elodi, S., Varadi, K.: Optimization of conditions for the catalytic effect of the factor IXa-factor VIII Complex: Probable role of the complex in the amplification of blood coagulation. *Thromb. Res.* 1979, 15, 617–629), inhibition of factor Xa may be more efficient than inactivation of thrombin in interrupting the blood coagulation system.

Therefore, efficacious and specific inhibitors of factor Xa are needed as potentially valuable therapeutic agents for the treatment of thromboembolic disorders. It is thus desirable to discover new factor Xa inhibitors.

SUMMARY OF THE INVENTION

Accordingly, one object of the present invention is to provide novel nitrogen containing heterobicycles which are useful as factor Xa inhibitors or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt or prodrug form thereof.

It is another object of the present invention to provide a method for treating thromboembolic disorders comprising administering to a host in need of such treatment a therapeutically effective amount of at least one of the compounds of the present invention or a pharmaceutically acceptable salt or prodrug form thereof.

It is another object of the present invention to provide novel bicyclic compounds for use in therapy.

It is another object of the present invention to provide the use of novel bicyclic compounds for the manufacture of a medicament for the treatment of a thromboembolic disorder.

These and other objects, which will become apparent during the following detailed description, have been achieved by the inventors' discovery that compounds of Formulas A and B

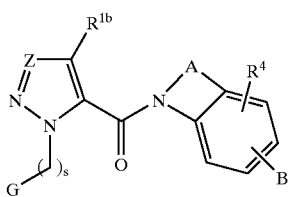

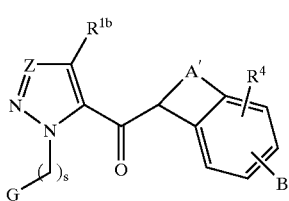

or pharmaceutically acceptable salt or prodrug forms thereof, are effective factor Xa inhibitors.

DETAILED DESCRIPTION OF PREFERRED EMBODIMENTS

[1] Thus, in an embodiment, the present invention provides a novel compound of formula A or B:

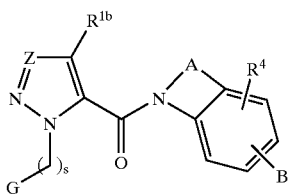

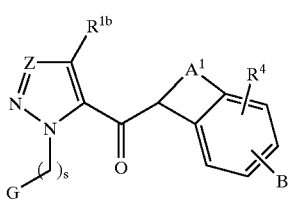

or a stereoisomer or pharmaceutically acceptable salt thereof;

G is a group of formula I or II:

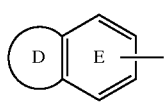

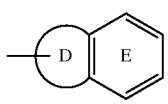

ring D is selected from —$(CH_2)_3$—, —$(CH_2)_4$—, —$CH_2N=CH$—, —$CH_2CH_2N=CH$—, and a 5–6 membered aromatic system containing from 0–2 heteroatoms selected from the group N, O, and S;

ring D, when present, is substituted with 0–2 R, provided that when ring D is unsubstituted, it contains at least one heteroatom;

E is selected from phenyl, pyridyl, pyrimidyl, pyrazinyl, and pyridazinyl, substituted with 0–1 R;

R is selected from Cl, F, Br, I, OH, $C_{1-3}$ alkoxy, $NH_2$, $NH(C_{1-3}$ alkyl), $N(C_{1-3}$ alkyl$)_2$, $CH_2NH_2$, $CH_2NH(C_{1-3}$ alkyl), $CH_2N(C_{1-3}$ alkyl$)_2$, $CH_2CH_2NH_2$, $CH_2CH_2NH(C_{1-3}$ alkyl), and $CH_2CH_2N(C_{1-3}$ alkyl$)_2$;

alternatively, ring D is absent;

when ring D is absent, ring E is selected from phenyl, pyridyl, pyrimidyl, pyrazinyl, and pyridazinyl, and ring E is substituted with $R^a$ and $R^b$;

$R^a$ is selected from H, F, Cl, Br, I, $SR^3$, $CO_2R^3$, $NO_2$, $(CH_2)_tOR^3$, $C_{1-4}$ alkyl, $OCF_3$, $CF_3$, $C(O)NR^7R^8$, and $(CR^8R^9)_tNR^7R^8$;

$R^b$ is selected from F, Cl, Br, I, OH, $C_{1-3}$ alkoxy, CN, $C(=NR^8)NR^7R^9$, $NHC(=NR^8)NR^7R^9$, $NR^8CH(=NR^7)$, $C(O)NR^7R^8$, $(CR^8R^9)_tNR^7R^8$, SH, $C_{1-3}$ alkyl-S, $S(O)R^{3b}$, $S(O)_2R^{3a}$, $S(O)_2NR^2R^{2a}$, $OCF_3$, and a 5–6 membered heteroaromatic system containing from 1–4 heteroatoms selected from the group N, O, and S and substituted with $R^c$;

alternatively, $R^a$ and $R^b$ combine to form methylenedioxy or ethylenedioxy;

$R^c$ is selected from OH, SH, $C_{1-3}$ alkoxy, $C_{1-3}$ thioalkoxy, $NH_2$, $NH(C_{1-3}$ alkyl), $N(C_{1-3}$ alkyl$)_2$, $CH_2NH_2$, $CH_2NH(C_{1-3}$ alkyl), $CH_2N(C_{1-3}$ alkyl$)_2$, $CH_2CH_2NH_2$, $CH_2CH_2NH(C_{1-3}$ alkyl), and $CH_2CH_2N(C_{1-3}$ alkyl$)_2$;

Z is N or $CR^{1a}$;

$R^{1a}$ is absent or selected from —$(CH_2)_r$—$R^{1c}$, —$CH=CH$—$R^{1c}$, $NCH_2R^{1d}$, $OCH_2R^{1d}$, $SCH_2R^{1d}$, $NH(CH_2)_2(CH_2)_tR^{1c}$, $O(CH_2)_2(CH_2)_tR^{1c}$, and $S(CH_2)_2(CH_2)_tR^{1c}$;

$R^{1b}$ is absent or selected from —$(CH_2)_r$—$R^{1c}$, —$CH=CH$—$R^{1c}$, $NCH_2R^{1d}$, $OCH_2R^{1d}$, $SCH_2R^{1d}$, $NH(CH_2)_2(CH_2)_tR^{1c}$, $O(CH_2)_2(CH_2)_tR^{1c}$, and $S(CH_2)_2(CH_2)_tR^{1c}$;

alternatively, $R^{1a}$ and $R^{1b}$, when both are present, together with the atoms to which they are attached form a 5–8 membered saturated, partially saturated or unsaturated ring substituted with 0–2 $R^4$ and which contains from 0–2 heteroatoms selected from the group consisting of N, O, and S;

$R^{1c}$ is selected from H, $C_{1-3}$ alkyl, F, Cl, Br, I, —CN, —CHO, $(CF_2)_rCF_3$, $(CH_2)_rOR^2$, $NR^2R^{2a}$, $C(O)R^{2c}$, $OC(O)R^2$, $(CF_2)_rCO_2R^{2c}$, $S(O)_pR^{2b}$, $NR^2(CH_2)_rOR^2$, $CH(=NR^{2c})NR^2R^{2a}$, $NR^2C(O)R^{2b}$, $NR^2C(O)NHR^{2b}$, $NR^2C(O)_2R^{2a}$, $OC(O)NR^{2a}R^{2b}$, $C(O)NR^2R^{2a}$, $C(O)NR^2(CH_2)_rOR^2$, $SO_2NR^2R^{2a}$, $NR^2SO_2R^{2b}$, $C_{3-6}$ carbocyclic residue substituted with 0–2 $R^4$, and 5–10 membered heterocyclic system containing from 1–4 heteroatoms selected from the group consisting of N, O, and S substituted with 0–2 $R^4$;

$R^{1d}$ is selected from H, $CH(CH_2OR^2)_2$, $C(O)R^{2c}$, $C(O)NR^2R^{2a}$, $S(O)R^{2b}$, $S(O)_2R^{2b}$, and $SO_2NR^2R^{2a}$;

$R^2$, at each occurrence, is selected from H, $CF_3$, $C_{1-6}$ alkyl, benzyl, $C_{3-6}$ carbocyclic residue substituted with 0–2 $R^{4b}$, a $C_{3-6}$ carbocyclic-$CH_2$— residue substituted with 0–2 $R^{4b}$, and 5–6 membered heterocyclic system containing from 1–4 heteroatoms selected from the group consisting of N, O, and S substituted with 0–2 $R^{4b}$;

$R^{2a}$, at each occurrence, is selected from H, $CF_3$, $C_{1-6}$ alkyl, benzyl, $C_{3-6}$ carbocyclic residue substituted with 0–2 $R^{4b}$, and 5–6 membered heterocyclic system containing from 1–4 heteroatoms selected from the group consisting of N, O, and S substituted with 0–2 $R^{4b}$;

$R^{2b}$, at each occurrence, is selected from $CF_3$, $C_{1-4}$ alkoxy, $C_{1-6}$ alkyl, benzyl, $C_{3-6}$ carbocyclic residue substituted with 0–2 $R^{4b}$, and 5–6 membered heterocyclic system containing from 1–4 heteroatoms selected from the group consisting of N, O, and S substituted with 0–2 $R^{4b}$;

$R^{2c}$, at each occurrence, is selected from $CF_3$, OH, $C_{1-4}$ alkoxy, $C_{1-6}$ alkyl, benzyl, $C_{3-6}$ carbocyclic residue substituted with 0–2 $R^{4b}$, and 5–6 membered heterocyclic system containing from 1–4 heteroatoms selected from the group consisting of N, O, and S substituted with 0–2 $R^{4b}$;

alternatively, $R^2$ and $R^{2a}$, together with the atom to which they are attached, combine to form a 5 or 6 membered saturated, partially saturated or unsaturated ring substituted with 0–2 $R^{4b}$ and containing from 0–1 additional heteroatoms selected from the group consisting of N, O, and S;

$R^3$, at each occurrence, is selected from H, $C_{1-4}$ alkyl, and phenyl;

$R^{3a}$, at each occurrence, is selected from H, $C_{1-4}$ alkyl, and phenyl;

$R^{3b}$, at each occurrence, is selected from H, $C_{1-4}$ alkyl, and phenyl;

$R^{3c}$, at each occurrence, is selected from $C_{1-4}$ alkyl, and phenyl;

A is 2–5 membered linker substituted with 0–2 $R^4$ and selected from $C_{2-4}$ alkylene, $C_{2-4}$ alkenylene, $(CH_2)_uO(CH_2)_u$, $(CH_2)_uNH(CH_2)_u$, $(CH_2)_uC(O)(CH_2)_u$, $(CH_2)_uC(O)O(CH_2)_u$, $(CH_2)_uOC(O)(CH_2)_u$, $(CH_2)_uC(O)NH(CH_2)_u$, $(CH_2)_uNHC(O)(CH_2)_u$, $(CH_2)_uS(O)_p(CH_2)_u$, $(CH_2)_uSO_2NH(CH_2)_u$, and $(CH_2)_uNHSO_2(CH_2)_u$, provided that A forms other than a N—O or N—S bond;

$A^1$ is 2–5 membered linker substituted with 0–2 $R^4$ and selected from $C_{2-4}$ alkylene, $C_{2-4}$ alkenylene, $(CH_2)_uO(CH_2)_u$, $(CH_2)_uNH(CH_2)_u$, $(CH_2)_uC(O)(CH_2)_u$, $(CH_2)_uC(O)O(CH_2)_u$, $(CH_2)_uOC(O)(CH_2)_u$, $(CH_2)_uC(O)NH(CH_2)_u$, $(CH_2)_uNHC(O)(CH_2)_u$, $(CH_2)_uS(O)_p(CH_2)_u$, $(CH_2)_uSO_2NH(CH_2)_u$, and $(CH_2)_uNHSO_2(CH_2)_u$, provided that $A^1$ forms other than a N—O or N—S bond;

alternatively, the $CH_2$—$A^1$ group is replaced by a group selected from C=CH—NH, C=CH—O, and C=CH—S;

B is selected from:
X—Y, $NR^2R^{2a}$, $C(=NR^2)NR^2R^{2a}$, $NR^2C(=NR^2)NR^2R^{2a}$,
$C_{3-10}$ carbocyclic residue substituted with 0–2 $R^{4a}$, and
5–10 membered heterocyclic system containing from 1–4 heteroatoms selected from the group consisting of N, O, and S substituted with 0–2 $R^{4a}$;

X is selected from $C_{1-4}$ alkylene, $-CR^2(CR^2R^{2b})(CH_2)_t-$, $-C(O)-$, $-C(=NR^{1d})-$, $-CR^2(NR^{1d}R^2)-$, $-CR^2(OR^2)-$, $-CR^2(SR^2)-$, $-C(O)CR^2R^{2a}-$, $-CR^2R^{2a}C(O)$, $-S(O)_p-$, $-S(O)_pCR^2R^{2a}-$, $-CR^2R^{2a}S(O)_p-$, $-S(O)_2NR^2-$, $-NR^2S(O)_2-$, $-NR^2S(O)_2CR^2R^{2a}-$, $-CR^2R^{2a}S(O)_2NR^2-$, $-NR^2S(O)_2NR^2-$, $-C(O)NR^2-$, $-NR^2C(O)-$, $-C(O)NR^2CR^2R^{2a}-$, $-NR^2C(O)CR^2R^{2a}-$, $-CR^2R^{2a}C(O)NR^2-$, $-CR^2R^{2a}NR^2C(O)-$, $-NR^2C(O)O-$, $-OC(O)NR^2-$, $-NR^2C(O)NR^2-$, $-NR^2-$, $-NR^2CR^2R^{2a}-$, $-CR^2R^{2a}NR^2-$, O, $-CR^2R^{2a}O-$, and $-OCR^2R^{2a}-$;

Y is selected from:
$(CH_2)_rNR^2R^{2a}$, provided that X—Y do not form a N—N, O—N, or S—N bond,
$C_{3-10}$ carbocyclic residue substituted with 0–2 $R^{4a}$, and
5–10 membered heterocyclic system containing from 1–4 heteroatoms selected from the group consisting of N, O, and S substituted with 0–2 $R^{4a}$;

$R^4$, at each occurrence, is selected from H, =O, $(CH_2)_rOR^2$, F, Cl, Br, I, $C_{1-4}$ alkyl, —CN, $NO_2$, $(CH_2)_rNR^2R^{2a}$, $(CH_2)_rC(O)R^{2c}$, $NR^2C(O)R^{2b}$, $C(O)NR^2R^{2a}$, $NR^2C(O)NR^2R^{2a}$, $CH(=NR^2)NR^2R^{2a}$, $CH(=NS(O)_2R^5)NR^2R^{2a}$, $NHC(=NR^2)NR^2R^{2a}$, $C(O)NHC(=NR^2)NR^2R^{2a}$, $SO_2NR^2R^{2a}$, $NR^2SO_2NR^2R^{2a}$, $NR^2SO_2-C_{1-4}$ alkyl, $NR^2SO_2R^5$, $S(O)_pR^5$, $(CF_2)_rCF_3$, $NCH_2R^{1d}$, $OCH_2R^{1d}$, $SCH_2R^{1d}$, $N(CH_2)_2(CH_2)_rR^{1c}$, $O(CH_2)_2(CH_2)_rR^{1c}$, and $S(CH_2)_2(CH_2)_rR^{1c}$;

$R^{4'}$, at each occurrence, is selected from H, =O, $(CH_2)_rOR^2$, F, Cl, Br, I, $C_{1-4}$ alkyl, —CN, $NO_2$, $(CH_2)_rNR^2R^{2a}$, $(CH_2)_rC(O)R^{2c}$, $NR^2C(O)R^{2b}$, $C(O)NR^2R^{2a}$, $SO_2NR^2R^{2a}$, and $(CF_2)_rCF_3$;

$R^{4a}$, at each occurrence, is selected from H, =O, $(CH_2)_rOR^2$, $(CH_2)_r$—F, $(CH_2)_r$—Br, $(CH_2)_r$—Cl, Cl, Br, F, I, $C_{1-4}$ alkyl, —CN, $NO_2$, $(CH_2)_rNR^2R^{2a}$, $(CH_2)_rC(O)R^{2c}$, $NR^2C(O)R^{2b}$, $C(O)NR^2R^{2a}$, $C(O)NH(CH_2)_2NR^2R^{2a}$, $NR^2C(O)NR^2R^{2a}$, $CH(=NR^2)NR^2R^{2a}$, $NHC(=NR^2)NR^2R^{2a}$, $SO_2NR^2R^{2a}$, $NR^2SO_2NR^2R^{2a}$, $NR^2SO_2-C_{1-4}$ alkyl, $C(O)NHSO_2-C_{1-4}$ alkyl, $NR^2SO_2R^5$, $S(O)_pR^5$, and $(CF_2)_rCF_3$;

alternatively, one $R^{4a}$ is a 5–6 membered aromatic heterocycle containing from 1–4 heteroatoms selected from the group consisting of N, O, and S substituted with 0–1 $R^5$;

$R^{4b}$, at each occurrence, is selected from H, =O, $(CH_2)_rOR^3$, F, Cl, Br, I, $C_{1-4}$ alkyl, —CN, $NO_2$, $(CH_2)_rNR^3R^{3a}$, $(CH_2)_rC(O)R^3$, $(CH_2)_rC(O)OR^{3c}$, $NR^3C(O)R^{3a}$, $C(O)NR^3R^{3a}$, $NR^3C(O)NR^3R^{3a}$, $CH(=NR^3)NR^3R^{3a}$, $NR^3C(=NR^3)NR^3R^{3a}$, $SO_2NR^3R^{3a}$, $NR^3SO_2NR^3R^{3a}$, $NR^3SO_2-C_{1-4}$ alkyl, $NR^3SO_2CF_3$, $NR^3SO_2$-phenyl, $S(O)_pCF_3$, $S(O)_p-C_{1-4}$ alkyl, $S(O)_p$-phenyl, and $(CF_2)_rCF_3$;

$R^5$, at each occurrence, is selected from $CF_3$, $C_{1-6}$ alkyl, phenyl substituted with 0–2 $R^6$, and benzyl substituted with 0–2 $R^6$;

$R^6$, at each occurrence, is selected from H, OH, $(CH_2)_rOR^2$, halo, $C_{1-4}$ alkyl, CN, $NO_2$, $(CH_2)_rNR^2R^{2a}$, $(CH_2)_rC(O)R^{2b}$, $NR^2C(O)R^{2b}$, $NR^2C(O)NR^2R^{2a}$, $CH(=NH)NH_2$, $NHC(=NH)NH_2$, $SO_2NR^2R^{2a}$, $NR^2SO_2NR^2R^{2a}$, and $NR^2SO_2C_{1-4}$ alkyl;

$R^7$, at each occurrence, is selected from H, OH, $C_{1-6}$ alkyl, $C_{1-6}$ alkylcarbonyl, $C_{1-6}$ alkoxy, $C_{1-4}$ alkoxycarbonyl, $(CH_2)_n$-phenyl, $C_{6-10}$ aryloxy, $C_{6-10}$ aryloxycarbonyl, $C_{6-10}$ arylmethylcarbonyl, $C_{1-4}$ alkylcarbonyloxy $C_{1-4}$ alkoxycarbonyl, $C_{6-10}$ arylcarbonyloxy $C_{1-4}$ alkoxycarbonyl, $C_{1-6}$ alkylaminocarbonyl, phenylaminocarbonyl, and phenyl $C_{1-4}$ alkoxycarbonyl;

$R^8$, at each occurrence, is selected from H, $C_{1-6}$ alkyl and $(CH_2)_n$-phenyl;

alternatively, $R^7$ and $R^8$ combine to form a 5 or 6 membered saturated, ring which contains from 0–1 additional heteroatoms selected from the group consisting of N, O, and S;

$R^9$, at each occurrence, is selected from H, $C_{1-6}$ alkyl and $(CH_2)_n$-phenyl;

n, at each occurrence, is selected from 0, 1, 2, and 3;
m, at each occurrence, is selected from 0, 1, and 2;
p, at each occurrence, is selected from 0, 1, and 2;
r, at each occurrence, is selected from 0, 1, 2, and 3;
s, at each occurrence, is selected from 0, 1, and 2;
t, at each occurrence, is selected from 0, 1, 2, and 3; and,
u, at each occurrence, is selected from 0, 1, 2, and 3.

[2] In a preferred embodiment, the present invention provides a novel compound, wherein the compound is selected from the group:

G is selected from the group:

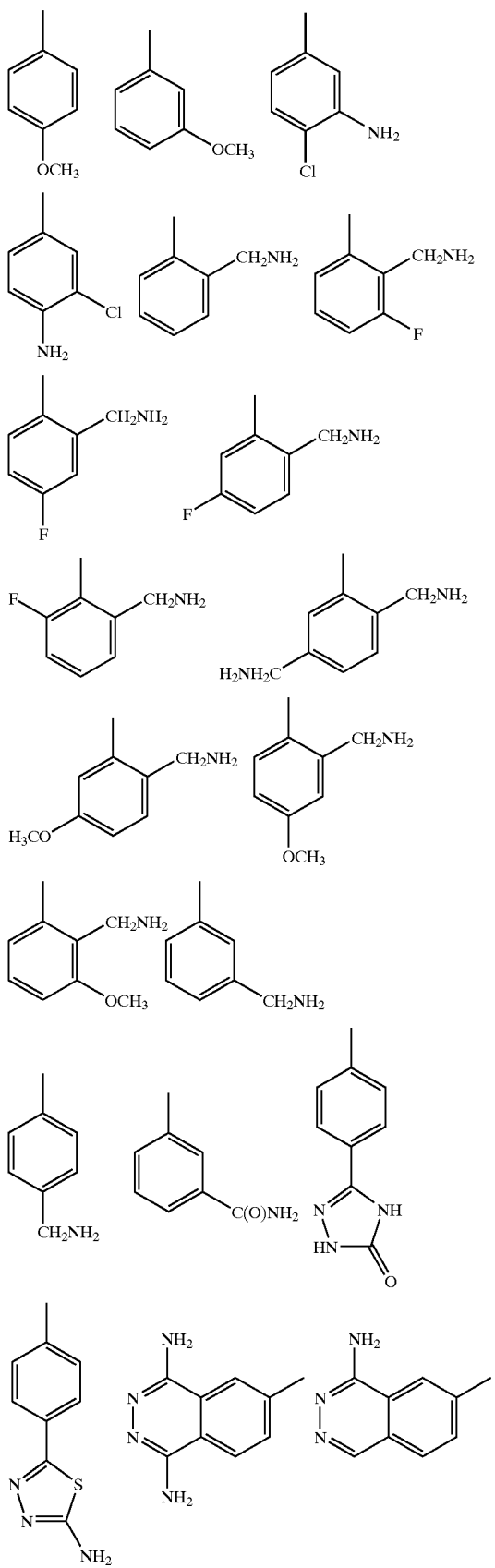

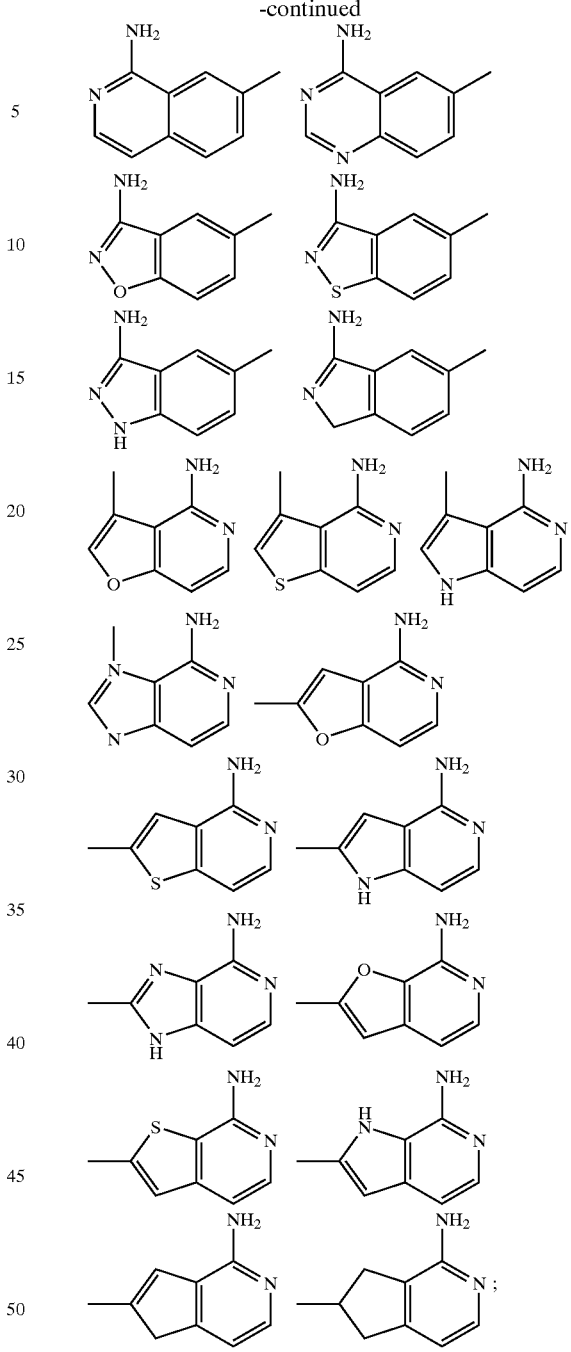

A is 3–5 membered linker substituted with 0–2 $R^4$ and selected from $C_{2-4}$ alkylene, $(CH_2)_uO(CH_2)_u$, $(CH_2)_uNH(CH_2)_u$, $(CH_2)_uC(O)(CH_2)_u$, $(CH_2)_uC(O)O(CH_2)_u$, $(CH_2)_u OC(O)(CH_2)_u$, $(CH_2)_uC(O)NH(CH_2)_u$, $(CH_2)_u NHC(O)(CH_2)_u$, $(CH_2)_uS(O)_p(CH_2)_u$, $(CH_2)_uSO_2NH(CH_2)_u$, and $(CH_2)_uNHSO_2(CH_2)_u$, provided that A forms other than a N—O or N—S bond;

$A^1$ is 3–5 membered linker substituted with 0–2 $R^4$ and selected from $C_{2-4}$ alkylene, $(CH_2)_uO(CH_2)_u$, $(CH_2)_uNH(CH_2)_u$, $(CH_2)_uC(O)(CH_2)_u$, $(CH_2)_uC(O)O(CH_2)_u$, $(CH_2)_u OC(O)(CH_2)_u$, $(CH_2)_uC(O)NH(CH_2)_u$, $(CH_2)_u NHC(O)(CH_2)_u$, $(CH_2)_uS(O)_p(CH_2)_u$, $(CH_2)_uSO_2NH(CH_2)_u$, and $(CH_2)_uNHSO_2(CH_2)_u$, provided that $A^1$ forms other than a N—O or N—S bond;

alternatively, the $CH_2$—$A^1$ group is replaced by a group selected from C=CH—NH and C=CH—O;

B is selected from: H, Y, X—Y;

X is selected from $C_{1-4}$ alkylene, —C(O)—, —C(=NR)—, —$CR^2(NR^2R^{2a})$—, —$C(O)CR^2R^{2a}$—, —$CR^2R^{2a}C(O)$, —$C(O)NR^2$—, —$NR^2C(O)$—, —$C(O)NR^2CR^2R^{2a}$—, —$NR^2C(O)CR^2R^{2a}$—, —$CR^2R^{2a}C(O)NR^2$—, —$CR^2R^{2a}NR^2C(O)$—, —$NR^2C(O)NR^2$—, —$NR^2$—, —$NR^2CR^2R^{2a}$—, —$CR^2R^{2a}NR^2$—, O, —$CR^2R^{2a}O$—, and —$OCR^2R^{2a}$—;

Y is $NR^2R^{2a}$, provided that X—Y do not form a N—N or O—N bond;

alternatively, Y is selected from one of the following carbocyclic and heterocyclic systems which are substituted with 0–2 $R^{4a}$; cyclopropyl, cyclopentyl, cyclohexyl, phenyl, piperidinyl, piperazinyl, pyridyl, pyrimidyl, furanyl, morpholinyl, thiophenyl, pyrrolyl, pyrrolidinyl, oxazolyl, isoxazolyl, isoxazolinyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;

alternatively, Y is selected from the following bicyclic heteroaryl ring systems:

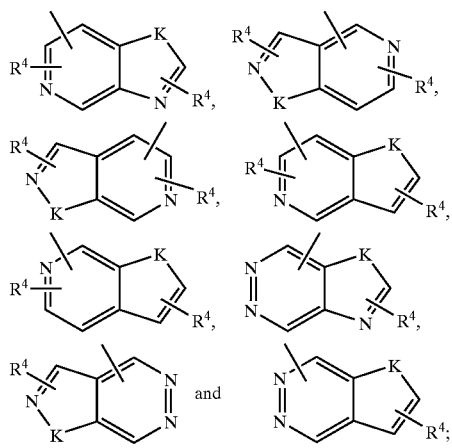

K is selected from O, S, NH, and N; and,
s is 0.

[3] In a more preferred embodiment, the present invention provides a novel compound, wherein the compound is selected from the group:

G is selected from the group:

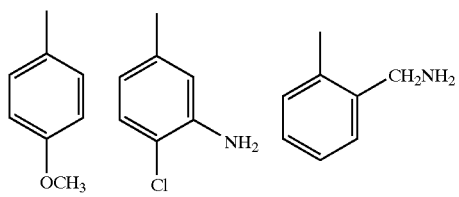

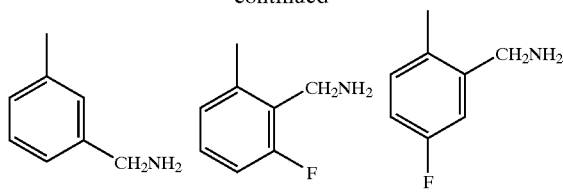

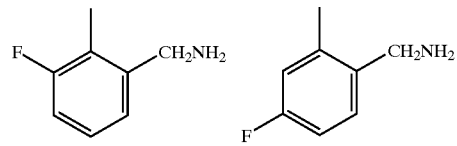

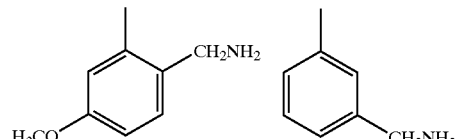

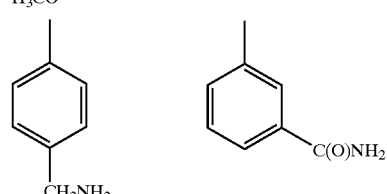

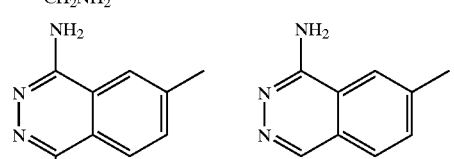

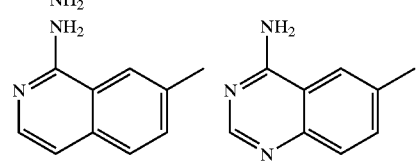

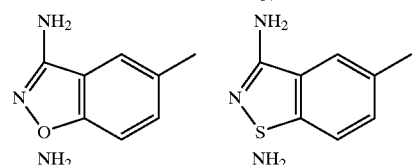

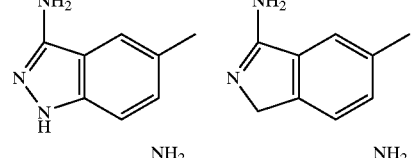

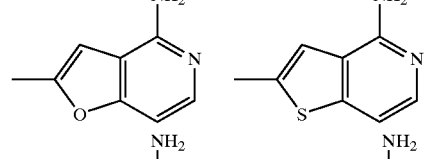

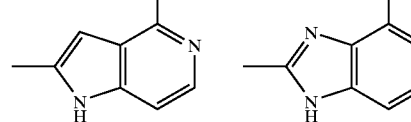

-continued

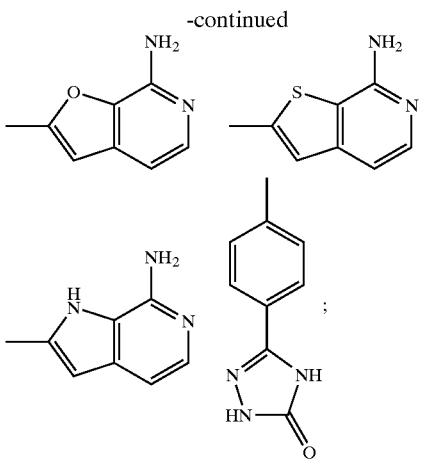

A is 3–5 membered linker substituted with 0–2 $R^4$ and selected from $C_{2-4}$ alkylene, $(CH_2)_uO(CH_2)_u$, $(CH_2)_uNH(CH_2)_u$, $(CH_2)_uC(O)(CH_2)_u$, $(CH_2)_uC(O)O(CH_2)_u$, $(CH_2)_u OC(O)(CH_2)_u$, $(CH_2)_uC(O)NH(CH_2)_u$, $(CH_2)_u NHC(O)(CH_2)_u$, $(CH_2)_uSO_2NH(CH_2)_u$, and $(CH_2)_uNHSO_2(CH_2)_u$, provided that A forms other than a N—O or N—S bond;

$A^1$ is 3–5 membered linker substituted with 0–2 $R^4$ and selected from $C_{2-4}$ alkylene, $(CH_2)_uO(CH_2)_u$, $(CH_2)_uNH(CH_2)_u$, $(CH_2)_uC(O)(CH_2)_u$, $(CH_2)_uC(O)NH(CH_2)_u$, $(CH_2)_uNHC(O)(CH_2)_u$, $(CH_2)_uSO_2NH(CH_2)_u$, and $(CH_2)_u NHSO_2(CH_2)_u$, provided that $A^1$ forms other than a N—O or N—S bond; and alternatively, the $CH_2$—$A^1$ group is replaced by a group selected from C═CH—NH and C═CH—O.

[4] In an even more preferred embodiment, the present invention provides a novel compound, wherein:

G is selected from:

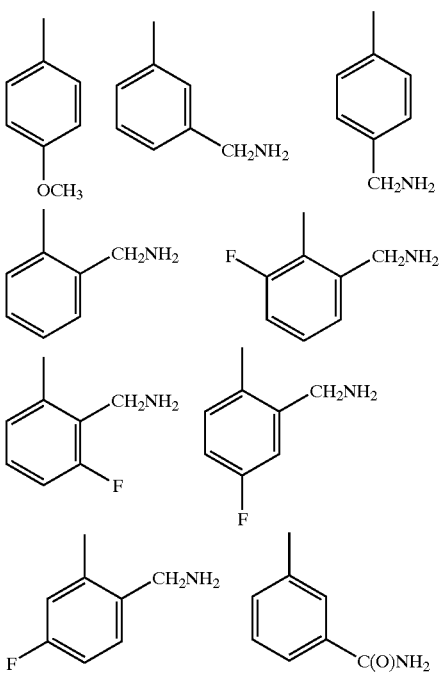

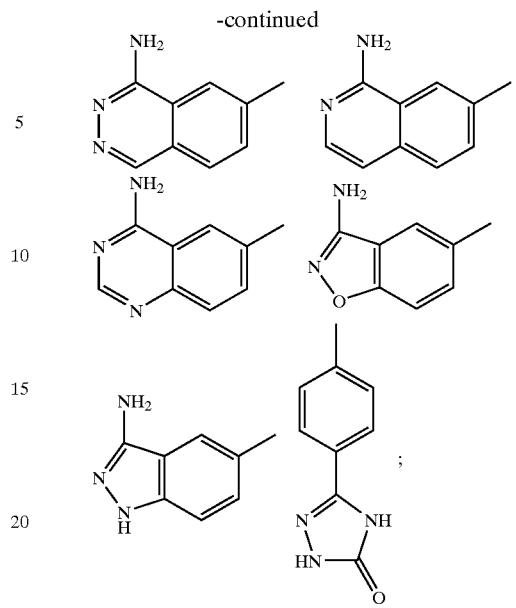

A is 3–5 membered linker substituted with 0–2 $R^4$ and selected from $C_{2-4}$ alkylene, $(CH_2)_uO(CH_2)_u$, $(CH_2)_uNH(CH_2)_u$, $(CH_2)_uC(O)(CH_2)_u$, $(CH_2)_uC(O)O(CH_2)_u$, and $(CH_2)_uOC(O)(CH_2)_u$, provided that A forms other than a N—O or N—S bond;

$A^1$ is 3–5 membered linker substituted with 0–2 $R^4$ and selected from $C_{2-4}$ alkylene, $(CH_2)_uO(CH_2)_u$, $(CH_2)_uNH(CH_2)_u$, $(CH_2)_uC(O)(CH_2)_u$, $(CH_2)_uC(O)NH(CH_2)_u$, $(CH_2)_uNHC(O)(CH_2)_u$, $(CH_2)_uSO_2NH(CH_2)_u$, and $(CH_2)_u NHSO_2(CH_2)_u$, provided that $A^1$ forms other than a N—O or N—S bond; and alternatively, the $CH_2$—$A^1$ group is replaced by a group selected from C═CH—NH and C═CH—O.

[5] In a still more preferred embodiment, the present invention provides a novel compound, wherein;

B is selected from X—Y, phenyl, pyrrolidino, morpholino, 1,2,3-triazolyl, and imidazolyl, and is substituted with 0–1 $R^{4a}$;

$R^2$, at each occurrence, is selected from H, $CH_3$, $CH_2CH_3$, cyclopropylmethyl, cyclobutyl, and cyclopentyl;

$R^{2a}$, at each occurrence, is H or $CH_3$;

alternatively, $R^2$ and $R^{2a}$, together with the atom to which they are attached, combine to form pyrrolidine substituted with 0–2 $R^{4b}$;

$R^4$, at each occurrence, is selected from OH, $(CH_2)_rOR^2$, halo, $C_{1-4}$ alkyl, $(CH_2)_rNR^2R^{2a}$, and $(CF_2)_rCF_3$;

$R^{4a}$ is selected from $C_{1-4}$ alkyl, $CF_3$, $(CH_2)_rNR^2R^{2a}$, $S(O)_p R^5$, $SO_2NR^2R^{2a}$, and 1-$CF_3$-tetrazol-2-yl;

$R^{4b}$, at each occurrence, is selected from H. $CH_3$, and OH;

$R^5$, at each occurrence, is selected from $CF_3$, $C_{1-6}$ alkyl, phenyl, and benzyl;

A is 3–5 membered linker substituted with 0–2 $R^4$ and selected from $C_{2-4}$ alkylene, $(CH_2)_uO(CH_2)_u$, $(CH_2)_uNH(CH_2)_u$, and $(CH_2)_uC(O)(CH_2)_u$, provided that A forms other than a N—O or N—S bond;

$A^1$ is 3–5 membered linker substituted with 0–2 $R^4$ and selected from $C_{2-4}$ alkylene, $(CH_2)_uO(CH_2)_u$, $(CH_2)_uNH(CH_2)_u$, $(CH_2)_uC(O)(CH_2)_u$, $(CH_2)_uC(O)NH(CH_2)_u$, $(CH_2)_uNHC(O)(CH_2)_u$, $(CH_2)_uSO_2NH(CH_2)_u$, and $(CH_2)_u NHSO_2(CH_2)_u$, provided that $A^1$ forms other than a N—O or N—S bond; and alternatively, the CH₂—A¹ group is replaced by a group selected from C=CH—NH and C=CH—O.
X is CH₂ or C(O);
Y is selected from pyrrolidino and morpholino; and,
r, at each occurrence, is selected from 0, 1, and 2.

[6] In a further preferred embodiment, the present invention provides a novel compound, wherein;

B is selected from the group: 2-(aminosulfonyl)phenyl, 2-(methylaminosulfonyl)phenyl, 1-pyrrolidinocarbonyl, 2-(methylsulfonyl)phenyl, 2-(N,N-dimethylaminomethyl)phenyl, 2-(N-pyrrolidinylmethyl)phenyl, 1-methyl-2-imidazolyl, 2-methyl-1-imidazolyl, 2-(dimethylaminomethyl)-1-imidazolyl, 2-(N-(cyclopropylmethyl)aminomethyl)phenyl, 2-(N-(cyclobutyl)aminomethyl)phenyl, 2-(N-(cyclopentyl)aminomethyl)phenyl, and 2-(N-(3-hydroxypyrrolidinyl)methyl)phenyl.

[7] In an even further preferred embodiment, the present invention provides a novel compound selected from:

1-[[1-[3-(Aminomethyl)phenyl]-3-(trifluoromethyl)-1H-pyrazol-5-yl]carbonyl]-5-[2-(aminosulfonyl)phenyl]-2,3-dihydro-1H-indole;
1-[[1-[3-(Aminoiminomethyl)phenyl]-3-(trifluoromethyl)-1H-pyrazol-5-yl]carbonyl]-5-[2-(aminosulfonyl)phenyl]-2,3-dihydro-1H-indole;
1-[[1-[3-Cyano-4-fluorophenyl]-3(trifluoromethyl)-1H-pyrazol-5-yl]carbonyl]-5-[2(aminosulfonyl)phenyl]-2,3-dihydro-1H-indole;
1-[[1-(3-Amino-1,2-benzisoxazol-5-yl)-3-(trifluoromethyl-1H-pyrazol-5-yl]carbonyl]-5-[2-(aminosulfonyl)phenyl]-2,3-dihydro-1H-indole;
1-[[1-(3-Amino-1,2-benzisoxazol-5-yl)-3-(trifluoromethyl)-1H-pyrazol-5-yl]carbonyl]-2,3-dihydro-5-[2-(methylsulfonyl)phenyl]-1H-indole;
1-[[1-(3-Amino-1,2-benzisoxazol-5-yl)-3-(trifluoromethyl)-1H-pyrazol-5-yl]carbonyl]-2,3-dihydro-5-[2-(1-pyrrolidinylmethyl)phenyl]-1H-indole;
1-[[1-(3-Amino-1,2-benzisoxazol-5-yl)-3-(trifluoromethyl)-1H-pyrazol-5-yl]carbonyl]-2,3-dihydro-5-[3-(1-pyrrolidinylmethyl)phenyl]-1H-indole;
1-[[1-(3-Amino-1,2-benzisoxazol-5-yl)-3-(trifluoromethyl)-1H-pyrazol-5-yl]carbonyl]-2,3-dihydro-5-[(2'-dimethylaminomethyl)imidazol-1-yl]-indoline;
1-[[1-(3-Amino-1,2-benzisoxazol-5-yl)-3-(trifluoromethyl)-1H-pyrazol-5-yl]carbonyl]-2,3,4,5-tetrahydro-7-[2-(aminosulfonyl)phenyl]-benzazepine;
1-[[1-(3-Amino-1,2-benzisoxazol-5-yl)-3-(trifluoromethyl)-1H-pyrazol-5-yl]carbonyl]-2,3-dihydro-6-[2-(methylsulfonyl)phenyl]-1H-quinolin-4-one;
1-[[1-(3-Amino-1,2-benzisoxazol-5-yl)-3-(trifluoromethyl)-1H-pyrazol-5-yl]carbonyl]-2,3-dihydro-6-[2-(methylsulfonyl)phenyl]-1H-quinoline;
4-[[1-(3-Amino-1,2-benzisoxazol-5-yl)-3-(trifluoromethyl)-1H-pyrazol-5-yl]carbonyl]-2,3-dihydro-7-[2-(methylsulfonyl)phenyl]-2H-1,4-benzoxazine;
1-[[1-(3-Amino-1,2-benzisoxazol-5-yl)-3-(trifluoromethyl)-1H-pyrazol-5-yl]carbonyl]-4-[2-(methylsulfonyl)phenyl]-3-indole;
5-[2-(aminosulfonyl)phenyl]-2,3-dihydro-1-[[1-(4-methoxyphenyl-3-(trifluoromethyl)-1H-pyrazol-5-yl]carbonyl]-1H-indole;
5-[2-(aminosulfonyl)phenyl]-1-[[1-(4-methoxyphenyl)-3-(trifluoromethyl)-1H-pyrazol-5-yl]carbonyl]-1H-indole;
1-[[1-(3-amino-1,2-benzisoxazol-5-yl)-3-(trifluoromethyl)-1H-pyrazol-5-yl]carbonyl]-6-[2-(aminosulfonyl)phenyl]-2,3-dihydro-4(1H)-quinolinone;
1-[[1-[3-(aminomethyl)phenyl]-3-(trifluoromethyl)-1H-pyrazol-5-yl]carbonyl]-2,3-dihydro-5-(1-pyrrolidinylcarbonyl)-1H-indole;
1-[[1-(3-amino-1,2-benzisoxazol-5-yl)-3-(trifluoromethyl)-1H-pyrazol-5-yl]carbonyl]-6-[2-(aminosulfonyl)phenyl]-1,2,3,4-tetrahydroquinoxaline;
1-[[1-(3-amino-1,2-benzisoxazol-5-yl)-3-(trifluoromethyl)-1H-pyrazol-5-yl]carbonyl]-7-[2-(aminosulfonyl)phenyl]-2,3,4,5-tetrahydro-1H-1-benzazepine;
1-[[1-(3-amino-1,2-benzisoxazol-5-yl)-3-(trifluoromethyl)-1H-pyrazol-5-yl]carbonyl]-7-[2-(aminosulfonyl)phenyl]-2,3,4,5-tetrahydro-1H-1,5-benzodiazepine;
1-[[1-(3-amino-1,2-benzisoxazol-5-yl)-3-(trifluoromethyl)-1H-pyrazol-5-yl]carbonyl]-7-[2-(aminosulfonyl)phenyl]-2,3,4,5-tetrahydro-1H-1,4-benzodiazepine;
5-[[1-(3-amino-1,2-benzisoxazol-5-yl)-3-(trifluoromethyl)-1H-pyrazol-5-yl]carbonyl]-8-[2-(aminosulfonyl)phenyl]-1,3,4,5-tetrahydro-2H-1,5-benzodiazepin-2-one;
5-[[1-(3-amino-1,2-benzisoxazol-5-yl)-3-(trifluoromethyl)-1H-pyrazol-5-yl]carbonyl]-8-[2-(aminosulfonyl)phenyl]-1,3,4,5-tetrahydro-2H-1,5-benzodiazepin-2-one;
1-[[1-[3-(aminoiminomethyl)phenyl]-3-(trifluoromethyl)-1H-pyrazol-5-yl]carbonyl]-5-[2-(aminosulfonyl)phenyl]-2,3-dihydro-1H-indole;
[1-(3-amino-1,2-benzisoxazol-5-yl)-3-(trifluoromethyl)-1H-pyrazol-5-yl][6-[2-[(dimethylamino)methyl]phenyl]-2,3-dihydro-1-methyl-1H-indol-3-yl]methanone;
5-[[1-(3-amino-1,2-benzisoxazol-5-yl)-3-(trifluoromethyl)-1H-pyrazol-5-yl]carbonyl]-8-[2-(aminosulfonyl)phenyl]-2,3,4,5-tetrahydro-1,5-benzoxazepine;
1-[[1-[3-(aminoiminomethyl)phenyl]-3-(trifluoromethyl)-1H-pyrazol-5-yl]carbonyl]-2,3-dihydro-5-[2-(methylsulfonyl)phenyl]-1H-indole;
[1-(3-amino-1,2-benzisoxazol-5-yl)-3-(trifluoromethyl)-1H-pyrazol-5-yl][6-[2-[(dimethylamino)methyl]phenyl]-2,3-dihydro-1H-indol-3-yl]methanone;
1-[[1-(3-amino-1,2-benzisoxazol-5-yl)-3-(trifluoromethyl)-1H-pyrazol-5-yl]carbonyl]-7-[2-(aminosulfonyl)phenyl]-1,2,3,4-tetrahydro-5H-1,4-benzodiazepin-5-one;
1-[[1-[3-(aminoiminomethyl)phenyl]-3-(trifluoromethyl)-1H-pyrazol-5-yl]carbonyl]-2,3-dihydro-5-[2-(1-pyrrolidinylmethyl)phenyl]-1H-indole;
[1-(3-amino-1,2-benzisoxazol-5-yl)-3-(trifluoromethyl)-1H-pyrazol-5-yl][2,3-dihydro-6-[2-(methylsulfonyl)phenyl]-1H-indol-3-yl]methanone;
1-[[1-(3-amino-1,2-benzisoxazol-5-yl)-3-(trifluoromethyl)-1H-pyrazol-5-yl]carbonyl]-7-[2-(aminosulfonyl)phenyl]-1,2,3,5-tetrahydro-4,1-benzoxazepine;
1-[[1-[3-(aminoiminomethyl)phenyl]-3-(trifluoromethyl)-1H-pyrazol-5-yl]carbonyl]-5-[2-[(dimethylamino)methyl]phenyl]-2,3-dihydro-1H-indole;
1-[[1-(1-amino-7-isoquinolinyl)-3-(trifluoromethyl)-1H-pyrazol-5-yl]carbonyl]-5-[2-[(dimethylamino)methyl]phenyl]-2,3-dihydro-1H-indole;
[1-(3-amino-1,2-benzisoxazol-5-yl)-3-(trifluoromethyl)-1H-pyrazol-5-yl][6-[2-[(dimethylamino)methyl]phenyl]-1H-indol-3-yl]methanone;
[1-(3-amino-1,2-benzisoxazol-5-yl)-3-(trifluoromethyl)-1H-pyrazol-5-yl][6-[2-[(dimethylamino)methyl]phenyl]-1-methyl-1H-indol-3-yl]methanone; and,
[1-(3-amino-1,2-benzisoxazol-5-yl)-3-(trifluoromethyl)-1H-pyrazol-5-yl][6-[2-[(dimethylamino)methyl]phenyl]-3-benzofuranyl]methanone;
or a pharmaceutically acceptable salt form thereof.

[8] In another embodiment, the present invention provides novel pharmaceutical compositions, comprising: a pharmaceutically acceptable carrier and a therapeutically effective amount of a compound of the present invention or a pharmaceutically acceptable salt form thereof.

[9] In another embodiment, the present invention provides a novel method for treating or preventing a thromboembolic disorder, comprising: administering to a patient in need thereof a therapeutically effective amount of a compound of the present invention or a pharmaceutically acceptable salt form thereof.

[10] In another embodiment, the present invention provides novel bicyclic compounds as described above for use in therapy.

[11] In another embodiment, the present invention provides the use of novel bicyclic compounds as described above for the manufacture of a medicament for the treatment of a thromboembolic disorder.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention.

The term "substituted," as used herein, means that any one or more hydrogens on the designated atom is replaced with a selection from the indicated group, provided that the designated atom's normal valency is not exceeded, and that the substitution results in a stable compound. When a substitent is keto (i.e., =O), then 2 hydrogens on the atom are replaced. Keto substituents are not present on aromatic moieties.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., $R^6$) occurs more than one time in any constituent or formula for a compound, its definition at each occurrence is independent of its definition at every other occurrence. Thus, for example, if a group is shown to be substituted with 0–2 $R^6$, then said group may optionally be substituted with up to two $R^6$ groups and $R^6$ at each occurrence is selected independently from the definition of $R^6$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" is intended to include both branched and straight-chain saturated aliphatic hydrocarbon groups having the specified number of carbon atoms. $C_{1-6}$ alkyl, is intended to include $C_1$, $C_2$, $C_3$, $C_4$, $C_5$, and $C_6$ alkyl groups. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. $C_{1-6}$ alkoxy, is intended to include $C_1$, $C_2$, $C_3$, $C_4$, $C_5$, and $C_6$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. $C_{3-7}$ cycloalkyl, is intended to include $C_3$, $C_4$, $C_5$, $C_6$, and $C_7$ cycloalkyl groups. Alkenyl" is intended to include hydrocarbon chains of either a straight or branched configuration and one or more unsaturated carbon-carbon bonds which may occur in any stable point along the chain, such as ethenyl and propenyl. $C_{2-10}$ alkenyl, is intended to include $C_2$, $C_3$, $C_4$, $C_5$, and $C_6$ alkenyl groups. "Alkynyl" is intended to include hydrocarbon chains of either a straight or branched configuration and one or more triple carbon-carbon bonds which may occur in any stable point along the chain, such as ethynyl and propynyl. $C_{2-6}$ alkynyl, is intended to include $C_2$, $C_3$, $C_4$, $C_5$, and $C_6$ alkynyl groups.

"Halo" or "halogen" as used herein refers to fluoro, chloro, bromo, and iodo; and "counterion" is used to represent a small, negatively charged species such as chloride, bromide, hydroxide, acetate, and sulfate.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane, [2.2.2] bicyclooctane, fluorenyl, phenyl, naphthyl, indanyl, adamantyl, and tetrahydronaphthyl.

As used herein, the term "heterocycle" or "heterocyclic system" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" or "heteroaryl" is intended to mean a stable 5, 6, or 7-membered monocyclic or bicyclic or 7, 8, 9, or 10-membered bicyclic heterocyclic aromatic ring which consists of carbon atoms and 1, 2, 3, or 4 heterotams independently selected from the group consisting of N, NH, O and S. It is to be noted that total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc. . . ) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers which release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention. Preferred prodrugs are amidine prodrugs wherein D is $C(=NR^7)NH_2$ or its tautomer $C(=NH)NHR^7$ and $R^7$ is selected from OH, $C_{1-4}$ alkoxy, $C_{6-10}$ aryloxy, $C_{1-4}$ alkoxycarbonyl, $C_{6-10}$ aryloxycarbonyl, $C_{6-10}$ arylmethylcarbonyl, $C_{1-4}$ alkylcarbonyloxy $C_{1-4}$ alkoxycarbonyl, and $C_{6-10}$ arylcarbonyloxy $C_{1-4}$ alkoxycarbonyl. More preferred prodrugs are where $R^7$ is OH, methoxy, ethoxy, benzyloxycarbonyl, methoxycarbonyl, and methylcarbonyloxymethoxycarbonyl.

"Stable compound" and "stable structure" are meant to indicate a compound that is sufficiently robust to survive isolation to a useful degree of purity from a reaction mixture, and formulation into an efficacious therapeutic agent.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e., =O) group, then 2 hydrogens on the atom are replaced.

"Therapeutically effective amount" is intended to include an amount of a compound of the present invention or an amount of the combination of compounds claimed effective to inhibit factor Xa. The combination of compounds is preferably a synergistic combination. Synergy, as described for example by Chou and Talalay, *Adv. Enzyme Regul.* 1984, 22, 27–55, occurs when the effect (in this case, inhibition of factor Xa) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased antiviral effect, or some other beneficial effect of the combination compared with the individual components.

SYNTHESIS

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley and Sons, 1991). All references cited herein are hereby incorporated in their entirety herein by reference.

Scheme 1

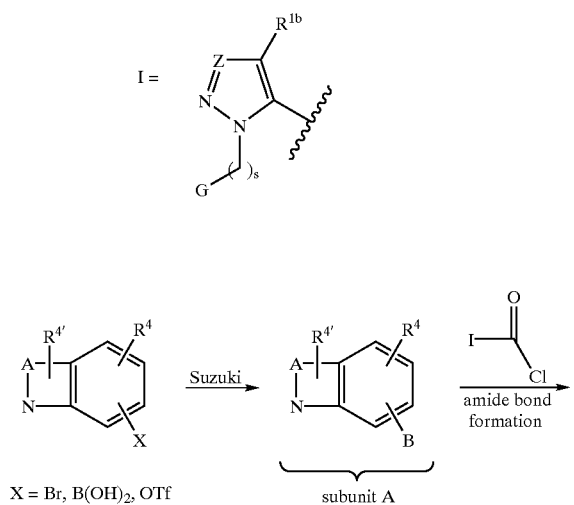

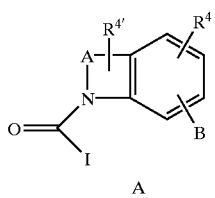

A general procedure for making compounds of type A is Described in Scheme 1. A preferred method for making an amide bond is treatment of the acid chloride of compounds of formula I with the sodium or potassium salt of subunit A in a solvent such as tetrahydrofuran or methylene chloride, followed by further manipulations as outlined in WO97/23212, WO98/28282, WO98/28269, WO98/57937, WO98/57951, and PCT/US98/26427, the contents of which are incorporated herein by reference, should lead to compounds of the present invention.

Scheme 2

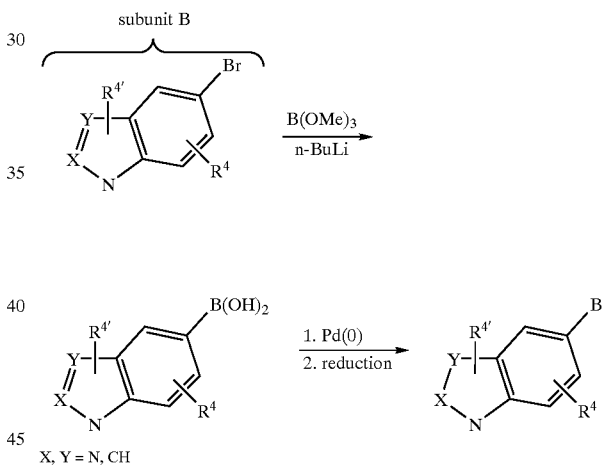

Preparation of subunit B can be done by means of the Suzuku reaction and is shown generically in Scheme 2. The generation of boronic acid from the corresponding bromide proceeds via halogen-metal exchange of the bromine with n-BuLi, followed by the quenching of the reaction mixture with triisopropylborate and acidic hydrolysis. The Suzuki reaction proceeds according to standard protocols, followed, when necessary, by reduction of the heterocyclic ring double bond. The subunit B can be already linked to the rest of the molecule, before the Suzuki reaction.

General and specific Schemes describing synthesis of subunit B of this invention are outlined in Schemes 3–12.

Scheme 3

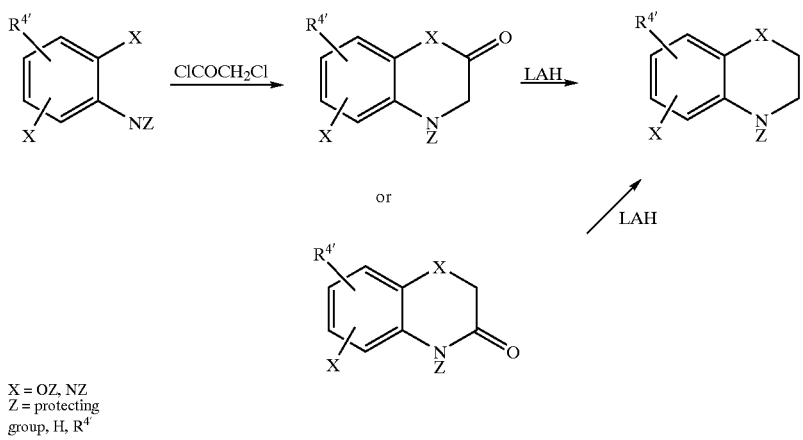

X = OZ, NZ
Z = protecting group, H, R$^{4'}$

Preparation of the compounds in this Scheme commences by the treatment of the appropriately substituted aniline with chloroacetyl chloride in the presence of the mild base in chloroform (see Huang et. al., *Synthesis* 1984, 851). The regioselectivity of the addition is dependent upon the choice of protecting groups. Reduction with LAH of either regioisomer produces the desired products.

Scheme 3a

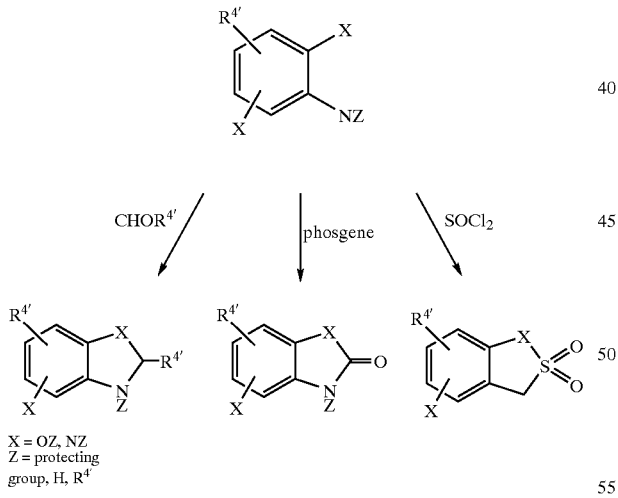

X = OZ, NZ
Z = protecting group, H, R$^{4'}$

Synthesis of various fused 5-ring heterocycles can be accomplished as outlined in Scheme 3a. An appropriately substituted aniline can be reacted with the appropriate reagents outlined in the scheme according to the methods known to those in the art to give the desired products.

Scheme 4

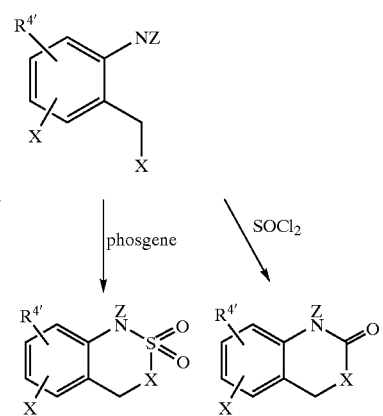

Synthesis of various 6-ring fused heterocycles shown in Scheme 4 follows the protocols outlined in Scheme 3a.

Scheme 5

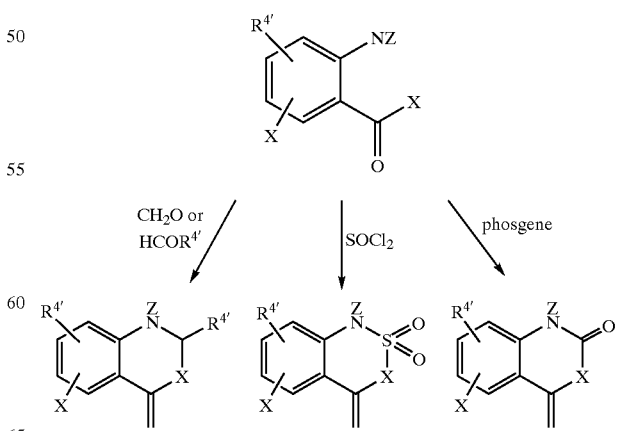

23

Synthesis of 6-ring fused heterocycles shown in Scheme 5 are similar to the methods desribed in Scheme 3a.

Scheme 6

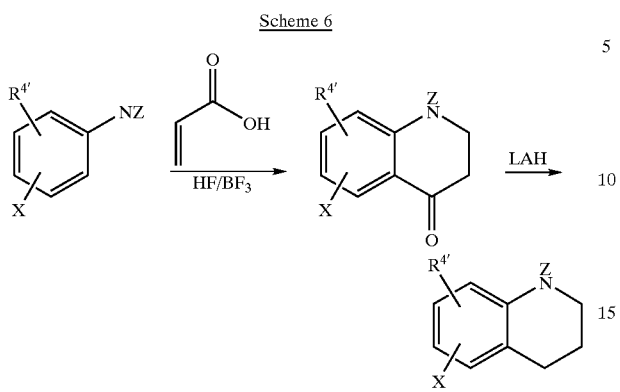

Synthesis of compounds described in Scheme 6 can be accomplished by reacting an appropriately substituted aniline with the acrylic acid, followed by Friedel-Crafts reaction in the presence of HF and $BF_3$ under pressure according to the protocol in WO94/412,075, followed by the reduction with LAH to afford the desired compounds.

Scheme 7

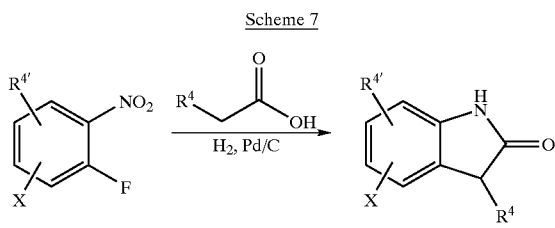

In Scheme 7, an appropriately substituted p-nitro-fluorobenzene can be reduced with hydrogen over Pd/C in the presence of derivatized acetic acid to effect closure to a desired benzolactam.

Scheme 8

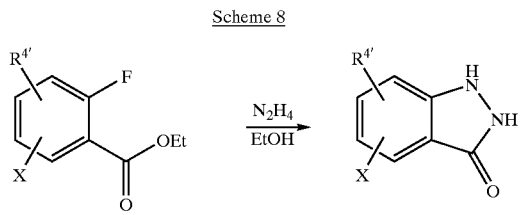

In Scheme 8, an appropriately substituted p-carboethoxy-fluorobenzene can react with hydrazine in ethanol to effect cyclization to a desired benzoazalactam.

Scheme 9

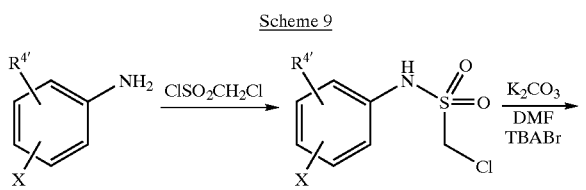

24

-continued

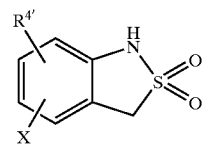

Synthesis of compounds shown in Scheme 9 can be accomplished according to the procedure by Wojciechowski et. al., *Synthesis* 1992, 6, 571. Treatment of an appropriately substituted aniline with chloromethylsulfonyl chloride can be followed by the closure to the sulfonamide ring under basic conditions in DMF in the presence of tert-butyl ammonia bromide to afford the desired compounds.

Scheme 10

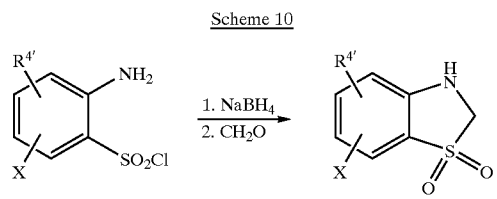

Preparation of compounds in Scheme 10 can proceed via reductive amination of the substituted o-amino-benzosulfonyl chloride in the presence of formaldehyde to afford the desired compound.

Scheme 11

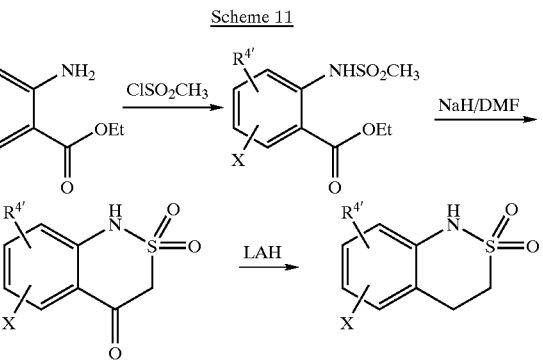

Compounds in Scheme 11 can be obtained following the protocol by Lombardino et. al., *J. Heterocycl. Chem* 1979, 9. Treatment of the intermediate sulfonamide, obtained by conventional methods, with sodium hydride in DMF effects ring closure. Subsequent reduction with LAH produces the desired compound.

Scheme 12

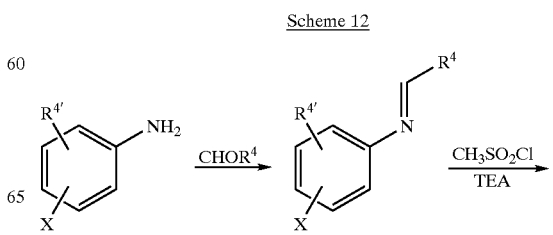

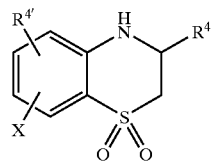

Compounds in Scheme 12 can be obtained by the methodology of Rai et. al. (*Chem. Ind., London* 1979, 26) by treatment of an intermediate substituted imine, obtained by the conventional methods, with methylsulfonyl chloride in THF.

Scheme 13

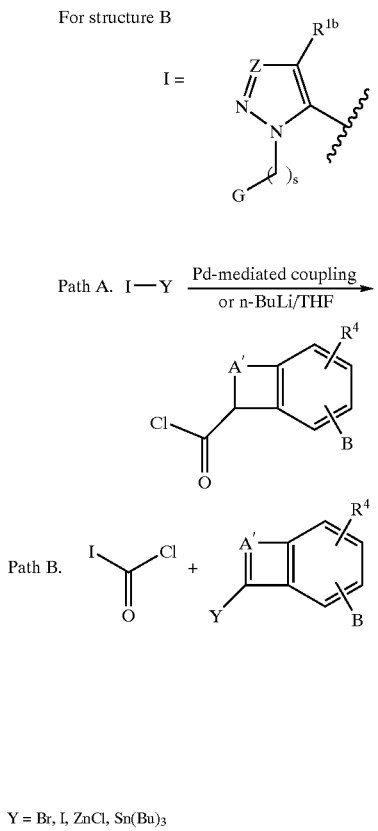

Y = Br, I, ZnCl, Sn(Bu)₃

General procedures for making the carbon-linked compounds of type B are presented in Scheme 13. Cross coupling reactions of this type are well known to those of skill in the art (see Negishi, *Tetr. Lett.* 1980, 24, 5181 or Sakamoto et. al., *Heterocycles* 1992, 2, 813 for palladium mediated coupling and Baxter et. al., *J. Med. Chem.* 1993, 36, 2739 or Pavlik et. al., *J. Heterocycl. Chem.* 1992, 1357 for n-BuLi reactions). Path A or B can be selected dependent on the ease of the synthesis of the right hand subunit. After the coupling reaction is complete the further manipulations, to obtain the final compounds of interest, are done according to WO97/23212, WO98/28282, WO98/28269, WO98/57937, WO98/57951, and PCT/US98/26427, the contents of which are incorporated herein by reference. General preparations of the intermediates for the cross coupling reactions are outlined in the following Schemes.

Scheme 14

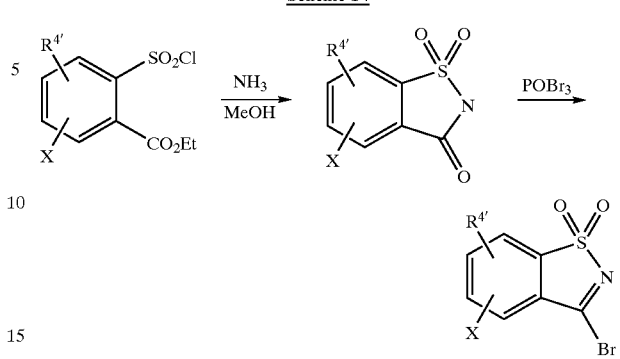

Intermediates useful for making compounds of the present invention can be prepared as shown in Scheme 14. An appropriately substituted phenylsulfonyl chloride can be treated with ammonia in methanol to afford an intermediate, which can be converted to the bromo-derivative after reacting with $POBr_3$. This compound undergoes a cross coupling reaction as outlined in Scheme 13, Path B.

Scheme 15

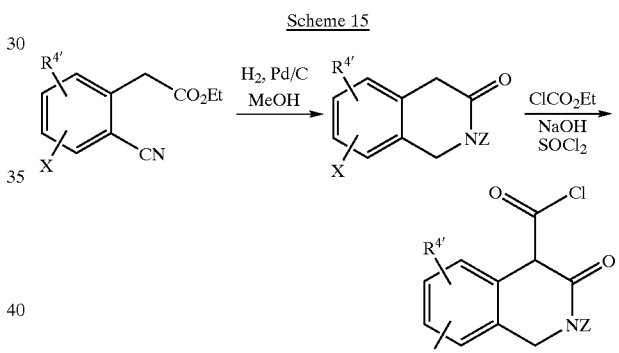

The compounds described in Scheme 15 can be prepared by reduction and subsequent cyclization of an appropriately substituted benzonitrile, followed by treatment with ethyl chloroformate in the presence of a strong base such as LDA. The intermediate ester can be hydrolyzed to the acid with NaOH in THF and water and converted to the acid chloride upon refluxing with thionyl chloride in a solvent such as methylene chloride or tetrahydrofuran. The target compounds then can be obtained via Path A, Scheme 13.

Scheme 16

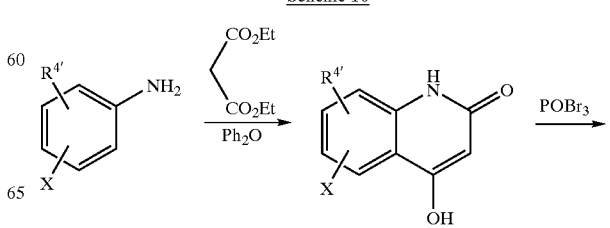

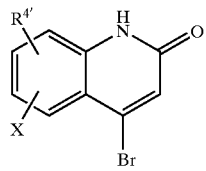

The compounds described in Scheme 16 can be obtained by the methodology of Yamaguchi et. al., *J. Heterocycl. Chem.* 1990, 27, 999. An appropriately substituted aniline can be reacted with diethylmalonate in diphenyl ether, followed by the teatment with $POBr_3$ to afford the bromide. The desired compounds then can be prepared according to Path B, Scheme 13.

Scheme 17

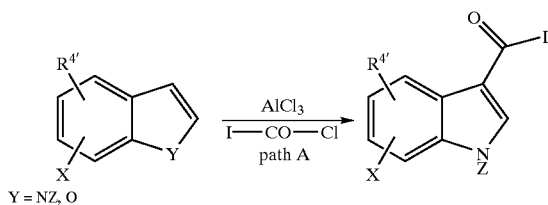

Y = NZ, O

The compounds of this invention can be obtained by the Friedel-Crafts reaction between an appropriately substituted indole or benzofuran and an acid chloride of the compounds of formula I in the presence of $AlCl_3$ as described by Murakami et. al., *Chem. Pharm. Bull.* 1988, 36, 2023 and Kwiecien et. al., *J. Heterocycl. Chem.* 1997, 34, 1587.

Scheme 18

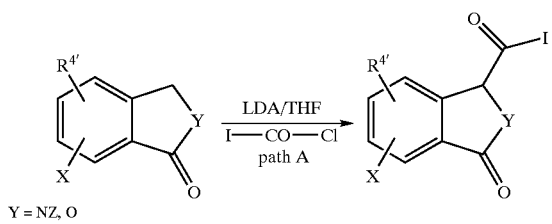

Y = NZ, O

As shown in Scheme 18, treatment of an appropriately susbtituted benzolactam or lactone, obtained by the methods known to those of skill in the art, with a strong base such as LDA, followed by addition of an acid chloride of formula I can affords the desired compounds.

Scheme 19

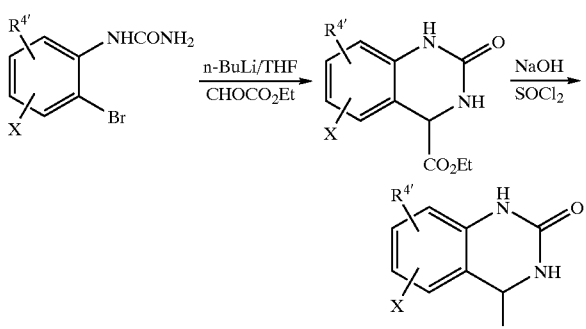

Preparation of compounds of Scheme 19 can proceed via halogen-metal exchange of a substituted benzourea and quenching the anion with ethyl glyoxylate to produce the cyclization product. Conversion of the ester to the acid chloride under standard conditions (Scheme 15) and further manipulation via path A, Scheme 13 leads to the desired products.

Scheme 20

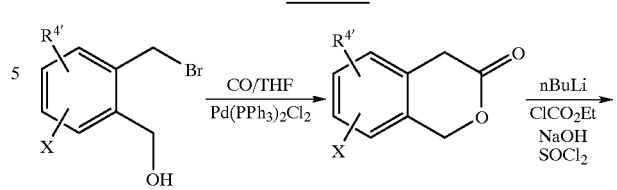

As shown in Scheme 20, intermediate benzolactones can be prepared from readily available starting materials upon treatment with carbon monoxide in THF in the presence of a catalytic amount of Pd(0). Further elaboration to the corresponding acid chloride follows the procedure outlined in Scheme 15.

Scheme 21

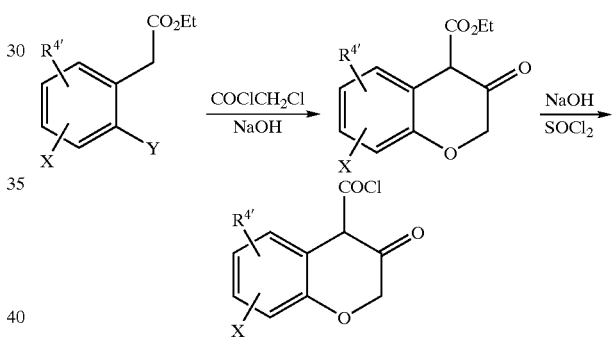

Y = OH, $NH_2$

Synthesis of the compounds shown in Scheme 21 can be accomplished according to the protocols described in Schemes 3 and 15.

Scheme 22

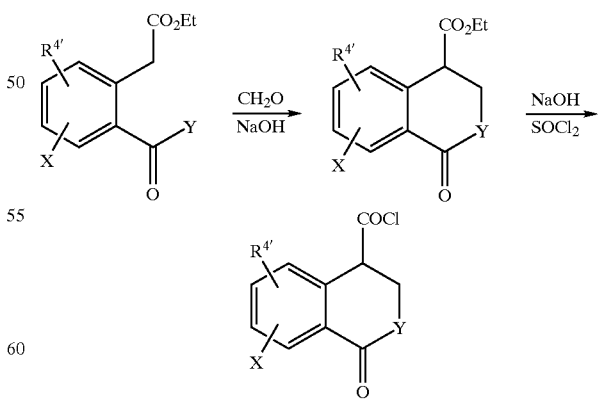

Y = OH, $NH_2$

In the case of compounds shown in Scheme 22, the desired benzolactams and lactones can be generated from available starting materials in a basic media with formaldehyde and an appropriate solvent. Conversion to the corresponding acid chloride can be achieved as desribed in Scheme 15.

chloride from the corresponding ester can be similar to the procedure of Scheme 15.

Scheme 23

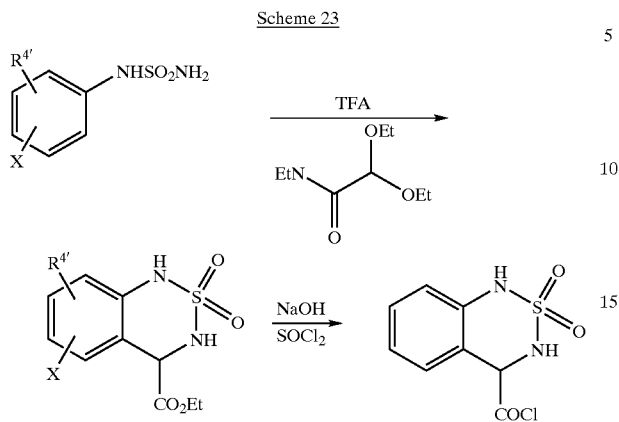

Scheme 24

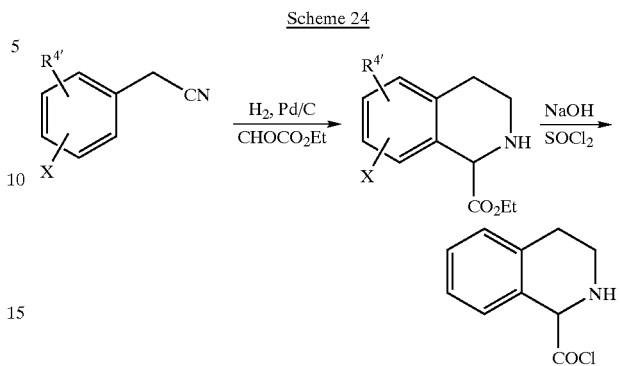

Preparation of the cyclic benzosulfonyl ureas shown in Scheme 23 can follow methodology described by Lee et. al., *J. Org. Chem.* 1990, 25, 6098. Generation of the acid Preparation of compounds outlined in Scheme 24 can proceed from readily available benzylic nitrites. Reduction with hydrogen over Pd/C and subsequent ring closure upon treatment with ethyl glyoxylate can provide an intermediate ester, that can be converted to an acid chloride following Scheme 15.

Scheme 25

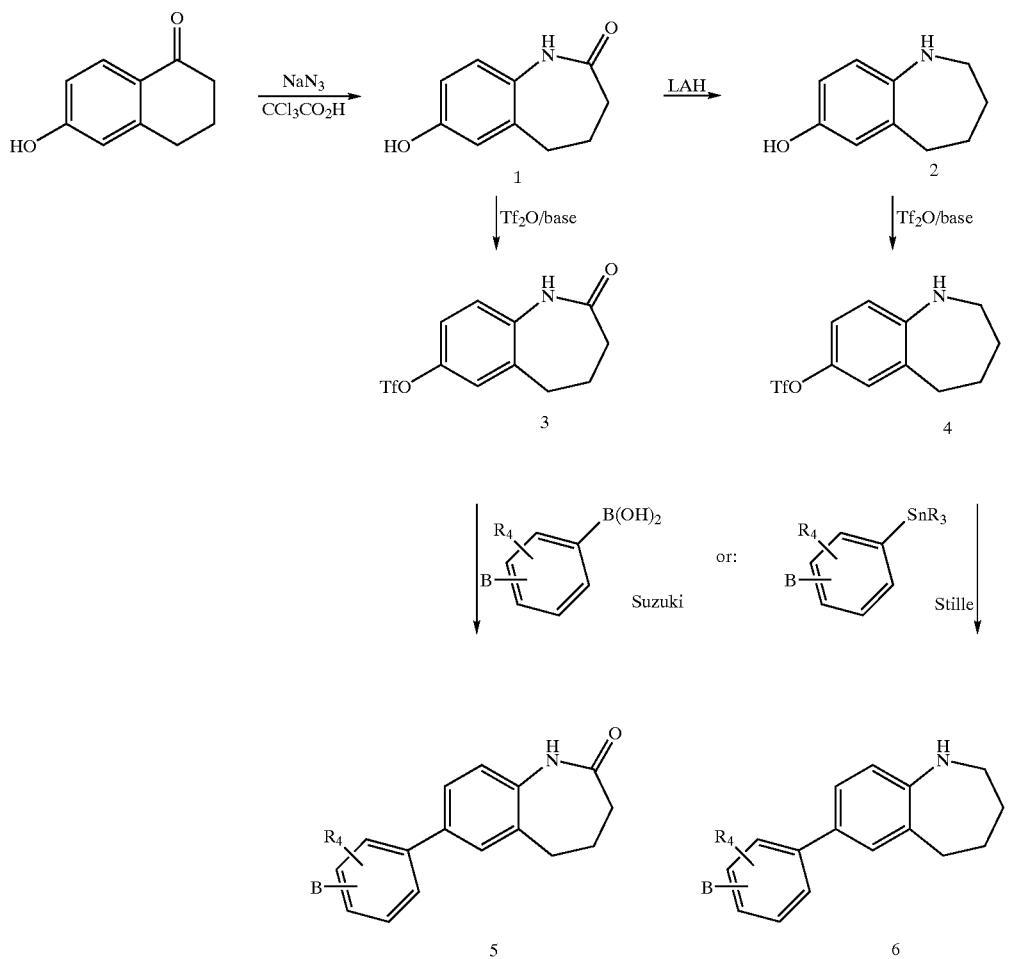

Compounds of formula A where A is —(CH$_2$)$_2$— and —CO(CH$_2$)$_3$— can be prepared by Schmidt rearrangement of 6-hydroxy-tetralone (Scheme 1). Treatment of 6-hydroxy-tetralone with sodium azide-trichloroacetic acid can afford hydroxybenzazepine 1, which can be reduced by LiAlH$_4$ to benzazepine 2 (see Valderrama et al. *Syn. Comm.* 1992, 22(4), 629–639). The hydroxy group of 1 and 2 can be then converted to triflate 3 and 4, which can undergo cross coupling with organoboron or organotin compounds (see a review by Ritter, *Synthesis*, "Synthetic Transformations of vinyl and aryl Triflates", 1993, 735–762) to give compounds 5 and 6.

Compounds of formula A where A is —(CH=CH)$_2$—, —CH$_2$CH=CHCH$_2$—, —CH=CH(CH$_2$)$_2$—, and —(CH$_2$)$_2$CH=CH— can be prepared by literature methods (see *Tetr. Lett.* 1985, 26(24), 2827–2830; *Bull. Soc. Chim. Fr.* 1992, 130(2), 143–145; *Tetr. Lett.* 1985, 26(5), 685–688 *Synthesis* 1985, 6–7, 612–619; and *Aust. J. Chem.* 1986, 39(3), 529–539).

Scheme 26

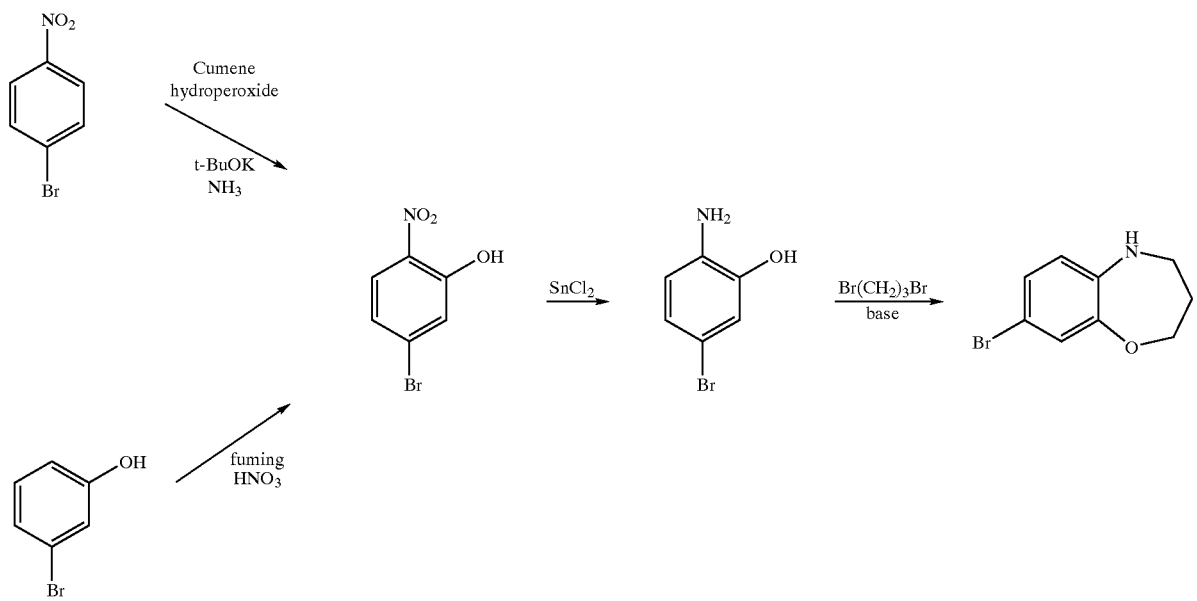

Compounds of formula A where A is —(CH$_2$)$_3$O— can be prepared as shown in Scheme 26 from 2-amino-5-bromophenol, which can be prepared from the methods either by Makosza (*J. Org. Chem.* 1998, 63(13), 4199–4208) or Hanzlik (*J. Org. Chem.* 1990, 55(9), 2763–2742).

Scheme 27

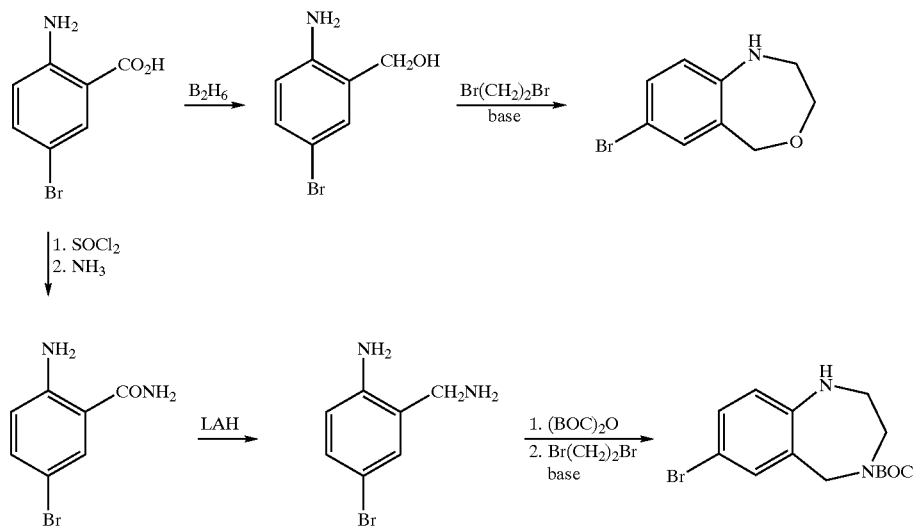

Compounds of formula A where A is —(CH$_2$)$_2$OCH$_2$— and —(CH$_2$)$_2$NCH$_2$— can be prepared from 2-amino-5-brombenzoic acid as shown in Scheme 27.

Scheme 28

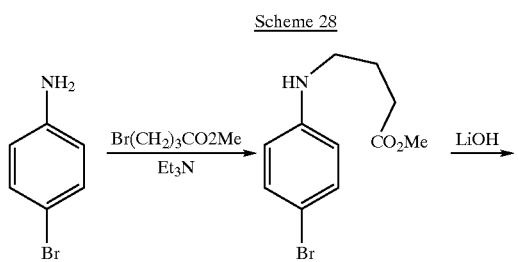

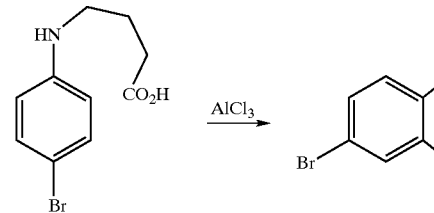

Compounds of formula A where A is —(CH$_2$)$_3$CO— can be prepared from 4-bromoaniline as shown in Scheme 28.

Scheme 29

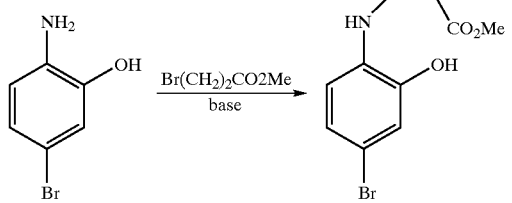

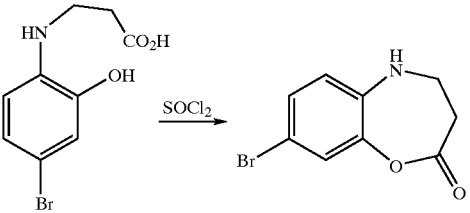

Compounds of formula A where A is —(CH$_2$)$_2$CO— can be prepared from 4-bromoaniline as shown in Scheme 29.

Scheme 30

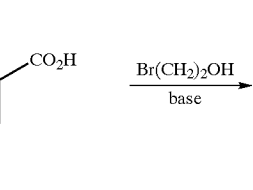

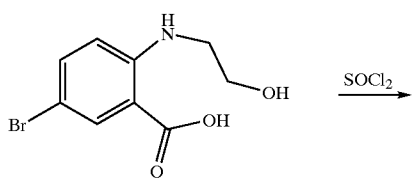

Compounds of formula A where A is —(CH$_2$)$_2$OCO— can be prepared from 4-bromoaniline as shown in Scheme 30.

Scheme 31

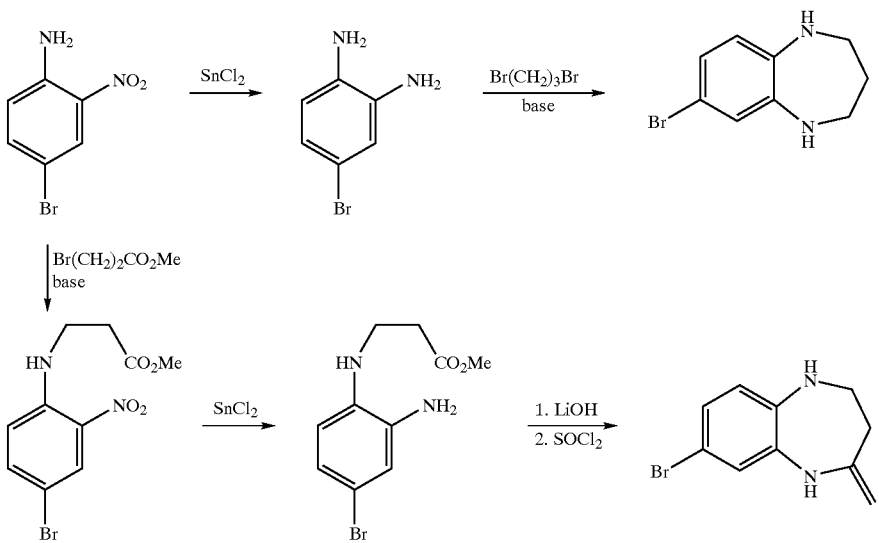

Compounds of formula A where A is —(CH$_2$)$_3$N— and —(CH$_2$)$_2$CON— can be prepared from 4-bromo-2-nitroaniline as shown in Scheme 31.

Scheme 32

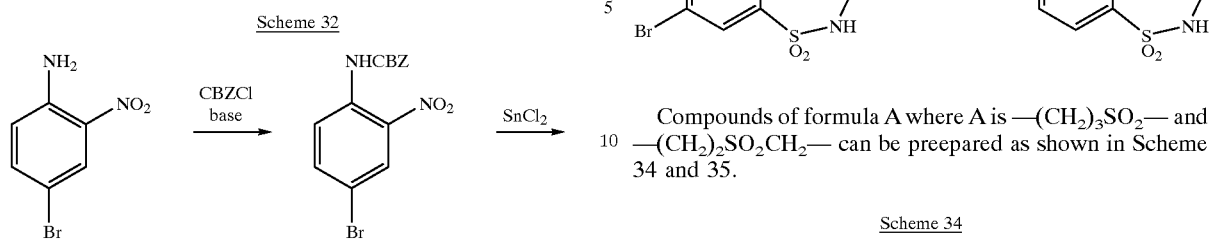

Compounds of formula A where A is —(CH$_2$)$_2$SO$_2$N— and —(CH$_2$)$_2$NSO$_2$— can be prepared as shown in Scheme 32 and 33 respectively.

Scheme 33

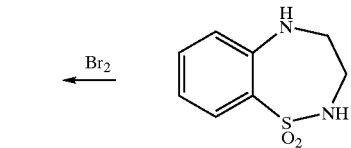

Compounds of formula A where A is —(CH$_2$)$_3$SO$_2$— and —(CH$_2$)$_2$SO$_2$CH$_2$— can be preepared as shown in Scheme 34 and 35.

Scheme 34

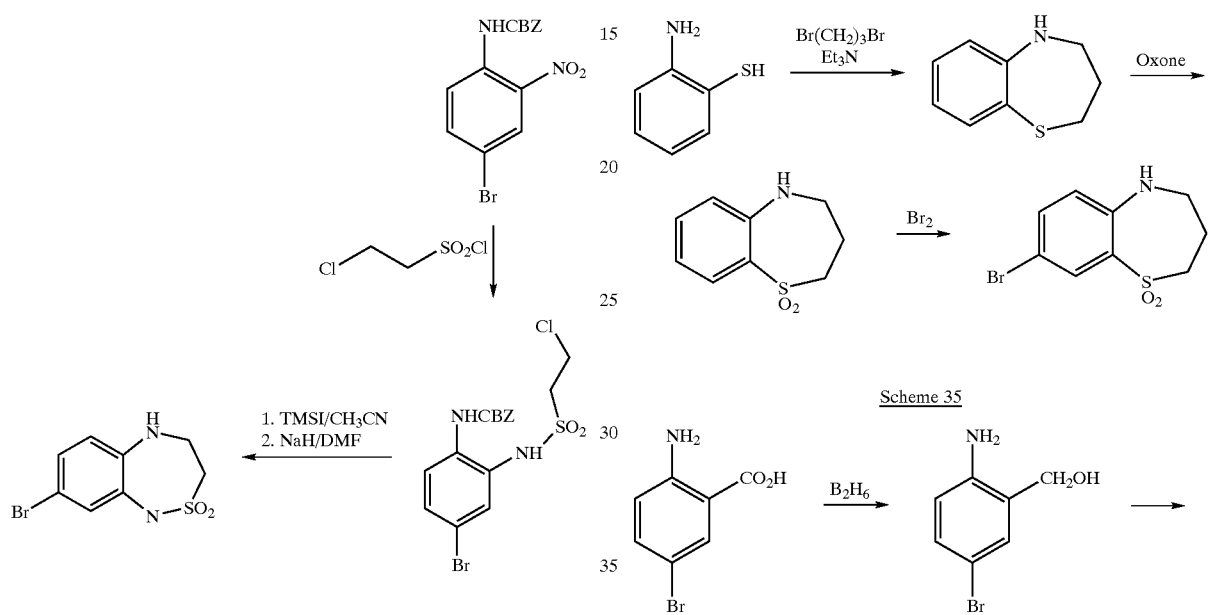

Scheme 35

Scheme 36

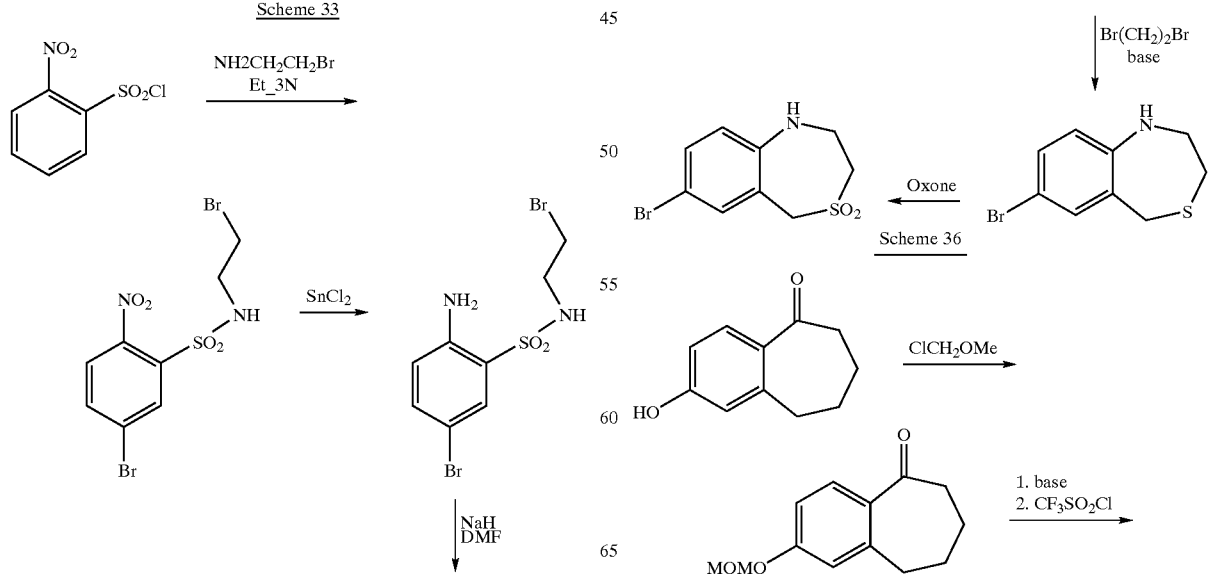

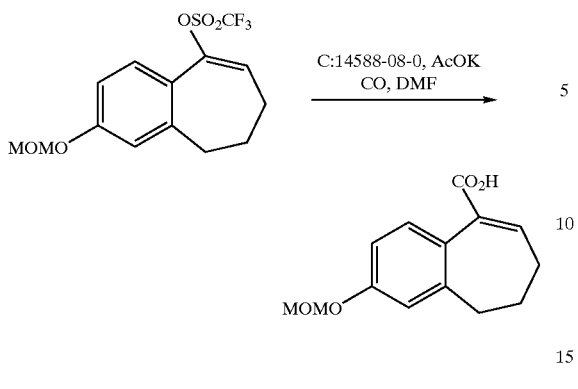

Compounds of formula B where $A^1$ is —CH=CH(CH$_2$)$_3$— can be prepared as shown in Scheme 36. The hydroxy group of benzosuberone (see *India. Org. Prep. Proced. Int.* 1992, 24(1), 27–32) can be protected with the MOM group and then the ketone group can be converted to enol trifluoromethylsulfonate, which can then be converted to the carboxylic acid (see *Tetra. Lett.* 1992, 33(27), 3939–3942).

Preferred compounds of the present invention are compounds of formulas A1-A2 and B1-B4 show below:

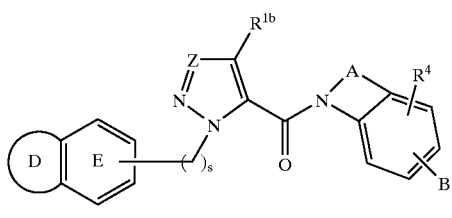

A1

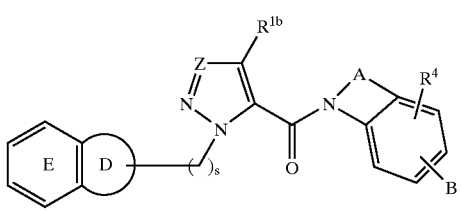

A2

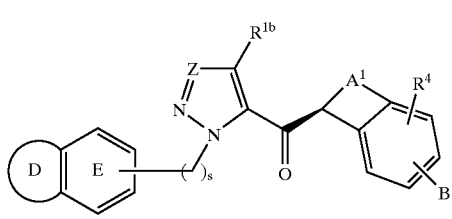

B1

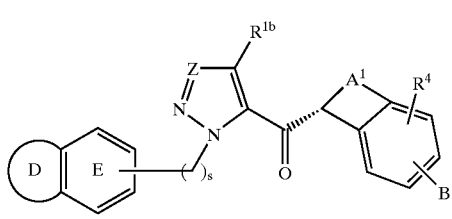

B2

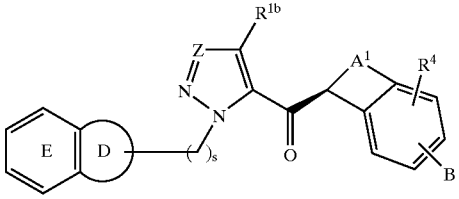

B3

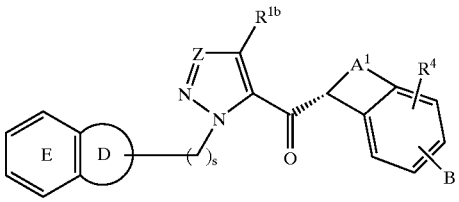

B4 or pharmaceutically acceptable salt forms thereof.

UTILITY

The compounds of this invention are useful as anticoagulants for the treatment or prevention of thromboembolic disorders in mammals. The term "thromboembolic disorders" as used herein includes arterial or venous cardiovascular or cerebrovascular thromboembolic disorders, including, for example, unstable angina, first or recurrent myocardial infarction, ischemic sudden death, transient ischemic attack, stroke, atherosclerosis, venous thrombosis, deep vein thrombosis, thrombophlebitis, arterial embolism, coronary and cerebral arterial thrombosis, cerebral embolism, kidney embolisms, and pulmonary embolisms. The anticoagulant effect of compounds of the present invention is believed to be due to inhibition of factor Xa or thrombin.

The effectiveness of compounds of the present invention as inhibitors of factor Xa was determined using purified human factor Xa and synthetic substrate. The rate of factor Xa hydrolysis of chromogenic substrate S2222 (Kabi Pharmacia, Franklin, Ohio) was measured both in the absence and presence of compounds of the present invention. Hydrolysis of the substrate resulted in the release of pNA, which was monitored spectrophotometrically by measuring the increase in absorbance at 405 nM. A decrease in the rate of absorbance change at 405 nm in the presence of inhibitor is indicative of enzyme inhibition. The results of this assay are expressed as inhibitory constant, $K_i$.

Factor Xa determinations were made in 0.10 M sodium phosphate buffer, pH 7.5, containing 0.20 M NaCl, and 0.5% PEG 8000. The Michaelis constant, $K_m$, for substrate hydrolysis was determined at 25° C. using the method of Lineweaver and Burk. Values of $K_i$ were determined by allowing 0.2–0.5 nM human factor Xa (Enzyme Research Laboratories, South Bend, Ind.) to react with the substrate (0.20 mM–1 mM) in the presence of inhibitor. Reactions were allowed to go for 30 minutes and the velocities (rate of absorbance change vs time) were measured in the time frame of 25–30 minutes. The following relationship was used to calculate $K_i$ values:

$$(v_o - v_s)/v_s = I/(K_i(1 + S/K_m))$$

where:
$v_o$ is the velocity of the control in the absence of inhibitor;
$v_s$ is the velocity in the presence of inhibitor;
I is the concentration of inhibitor;

$K_i$ is the dissociation constant of the enzyme:inhibitor complex;

S is the concentration of substrate;

$K_m$ is the Michaelis constant.

Using the methodology described above, a number of compounds of the present invention were found to exhibit a $K_i$ of $\leq 10 \mu M$, thereby confirming the utility of the compounds of the present invention as effective Xa inhibitors.

Compounds tested in the above assay are considered to be active if they exhibit a $K_i$ of $\leq 10 \mu M$. Preferred compounds of the present invention hava $K_i$'s of $\leq 1 \mu M$. More preferred compounds of the present invention hava $K_i$'s of $\leq 0.1 \mu M$. Even more preferred compounds of the present invention hava $K_i$'s of $\leq 0.01 \mu M$. Still more preferred compounds of the present invention hava $K_i$'s of $\leq 0.001 \mu M$.

The antithrombotic effect of compounds of the present invention can be demonstrated in a rabbit arterio-venous (AV) shunt thrombosis model. In this model, rabbits weighing 2–3 kg anesthetized with a mixture of xylazine (10 mg/kg i.m.) and ketamine (50 mg/kg i.m.) are used. A saline-filled AV shunt device is connected between the femoral arterial and the femoral venous cannulae. The AV shunt device consists of a piece of 6-cm tygon tubing which contains a piece of silk thread. Blood will flow from the femoral artery via the AV-shunt into the femoral vein. The exposure of flowing blood to a silk thread will induce the formation of a significant thrombus. After forty minutes, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The ID50 values (dose which produces 50% inhibition of thrombus formation) are estimated by linear regression.

The compounds of the present invention may also be useful as inhibitors of serine proteases, notably human thrombin, plasma kallikrein and plasmin. Because of their inhibitory action, these compounds are indicated for use in the prevention or treatment of physiological reactions, blood coagulation and inflammation, catalyzed by the aforesaid class of enzymes. Specifically, the compounds have utility as drugs for the treatment of diseases arising from elevated thrombin activity such as myocardial infarction, and as reagents used as anticoagulants in the processing of blood to plasma for diagnostic and other commercial purposes.

Some compounds of the present invention were shown to be direct acting inhibitors of the serine protease thrombin by their ability to inhibit the cleavage of small molecule substrates by thrombin in a purified system. In vitro inhibition constants were determined by the method described by Kettner et al. in *J. Biol. Chem.* 265, 18289–18297 (1990), herein incorporated by reference. In these assays, thrombin-mediated hydrolysis of the chromogenic substrate S2238 (Helena Laboratories, Beaumont, Tex.) was monitored spectrophotometrically. Addition of an inhibitor to the assay mixture results in decreased absorbance and is indicative of thrombin inhibition. Human thrombin (Enzyme Research Laboratories, Inc., South Bend, Ind.) at a concentration of 0.2 nM in 0.10 M sodium phosphate buffer, pH 7.5, 0.20 M NaCl, and 0.5% PEG 6000, was incubated with various substrate concentrations ranging from 0.20 to 0.02 mM. After 25 to 30 minutes of incubation, thrombin activity was assayed by monitoring the rate of increase in absorbance at 405 nm which arises owing to substrate hydrolysis. Inhibition constants were derived from reciprocal plots of the reaction velocity as a function of substrate concentration using the standard method of Lineweaver and Burk. Using the methodology described above, some compounds of this invention were evaluated and found to exhibit a $K_i$ of less than $10 \mu m$, thereby confirming the utility of the compounds of the present invention as effective thrombin inhibitors.

The compounds of the present invention can be administered alone or in combination with one or more additional therapeutic agents. These include other anticoagulant or coagulation inhibitory agents, anti-platelet or platelet inhibitory agents, thrombin inhibitors, or thrombolytic or fibrinolytic agents.

The compounds are administered to a mammal in a therapeutically effective amount. By "therapeutically effective amount" it is meant an amount of a compound of the present invention that, when administered alone or in combination with an additional therapeutic agent to a mammal, is effective to prevent or ameliorate the thromboembolic disease condition or the progression of the disease.

By "administered in combination" or "combination therapy" it is meant that the compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect. Other anticoagulant agents (or coagulation inhibitory agents) that may be used in combination with the compounds of this invention include warfarin and heparin, as well as other factor Xa inhibitors such as those described in the publications identified above under Background of the Invention.

The term anti-platelet agents (or platelet inhibitory agents), as used herein, denotes agents that inhibit platelet function such as by inhibiting the aggregation, adhesion or granular secretion of platelets. Such agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam, including pharmaceutically acceptable salts or prodrugs thereof. Of the NSAIDS, aspirin (acetylsalicyclic acid or ASA), and piroxicam are preferred. Other suitable anti-platelet agents include ticlopidine, including pharmaceutically acceptable salts or prodrugs thereof. Ticlopidine is also a preferred compound since it is known to be gentle on the gastro-intestinal tract in use. Still other suitable platelet inhibitory agents include IIb/IIIa antagonists, thromboxane-A2-receptor antagonists and thromboxane-A2-synthetase inhibitors, as well as pharmaceutically acceptable salts or prodrugs thereof.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/ or serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin and argatroban, including pharmaceutically acceptable salts and prodrugs thereof. Boroarginine derivatives and boropeptides include N-acetyl and peptide derivatives of boronic acid, such as C-terminal a-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin. Boropeptide thrombin inhibitors include compounds described in Kettner et al., U.S. Pat. No. 5,187,157 and EP 293 881 A2, the disclosures of which are hereby incorporated herein by reference. Other suitable boroarginine derivatives and boropeptide thrombin inhibitors include those disclosed in WO92/07869 and EP 471,651 A2, the disclosures of which are hereby incorporated herein by reference.

The term thrombolytics (or fibrinolytic) agents (or thrombolytics or fibrinolytics), as used herein, denotes agents that lyse blood clots (thrombi). Such agents include tissue plasminogen activator, anistreplase, urokinase or streptokinase, including pharmaceutically acceptable salts or prodrugs thereof. The term anistreplase, as used herein, refers to anisoylated plasminogen streptokinase activator complex, as described, for example, in EP 028,489, the disclosure of which is hereby incorporated herein by reference herein. The term urokinase, as used herein, is intended to denote both dual and single chain urokinase, the latter also being referred to herein as prourokinase.

Administration of the compounds of the present invention in combination with such additional therapeutic agent, may afford an efficacy advantage over the compounds and agents alone, and may do so while permitting the use of lower doses of each. A lower dosage minimizes the potential of side effects, thereby providing an increased margin of safety.

The compounds of the present invention are also useful as standard or reference compounds, for example as a quality standard or control, in tests or assays involving the inhibition of factor Xa. Such compounds may be provided in a commercial kit, for example, for use in pharmaceutical research involving factor Xa. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving factor Xa. For example, the presence of factor Xa in an unknown sample could be determined by addition of chromogenic substrate S2222 to a series of solutions containing test sample and optionally one of the compounds of the present invention. If production of pNA is observed in the solutions containing test sample, but not in the presence of a compound of the present invention, then one would conclude factor Xa was present.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where the compounds of this invention are combined with other anticoagulant agents, for example, a daily dosage may be about 0.1 to 100 milligrams of the compound of the present invetion and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where the compounds of the present invetion are administered in combination with an anti-platelet agent, by way of general guidance, typically a daily dosage may be about 0.01 to 25 milligrams of the compound of the present invention and about 50 to 150 milligrams of the anti-platelet agent, preferably about 0.1 to 1 milligrams of the compound of the present invention and about 1 to 3 milligrams of antiplatelet agents, per kilogram of patient body weight.

Where the compounds of the present invetion are administered in combination with thrombolytic agent, typically a daily dosage may be about 0.1 to 1 milligrams of the compound of the present invention, per kilogram of patient body weight and, in the case of the thrombolytic agents, the usual dosage of the thrombolyic agent when administered alone may be reduced by about 70–80% when administered with a compound of the present invetion.

Where two or more of the foregoing second therapeutic agents are administered with the compound of the present invention, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-

EXAMPLES

Example 1

2-(2,3-Dihydro-1H-indol-5-yl)-N-(1,1-dimethylethyl)benzenesulfonamide

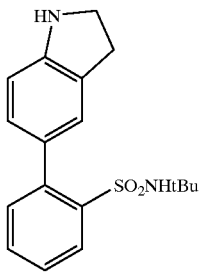

A solution of 5-indoleboronic acid (2.9 g, 18 mmol), prepared according to the procedure of Yang (*Heterocycles* 1992, 34, 1169) and 2-bromobenzyl-tert-butylsulfonyl amide (2.5 g, 18 mmol) in a mixture of ethylene glycol dimethyl ether (20 mL) and aqueous sodium carbonate (10 mL) was deoxygenated by a rapid stream of nitrogen applied to the system for 20 min, then treated with Pd(0) at once. The reaction was refluxed for 18 h, cooled down, filtered through Celite® and washed with THF (20 mL). The filtrate was evaporated to dryness, taken up in water and extracted with EtOAc (3×). The EtOAc extracts were dried over sodium sulfate and concentrated. The crude residue was purified by flash chromatography (hexane/EtOAc, 1:3) to afford 2-(1H-indol-5-yl)-N-(1,1-dimethylethyl)benzenesulfonamide (0.7 g, 12%).

The product (0.29 g, 0.9 mmol) was disolved in acetic acid and treated with sodium cyanoborohydride (54 mg, 0.9 mmol). The reaction mixture was stirred for 4 h, concentrated and purified through a plug of silica gel (hexane/EtOAc, 1:1) to afford the title product (232 mg, 77%). LRMS (ES+): 331.1 (M+H)+.

Example 2

2,3-Dihydro-5-[2-(methylthio)phenyl]-1H-indole

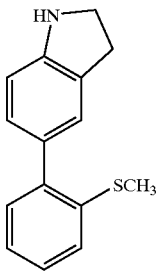

A solution of 5-indoleboronic acid (2.0 g, 12 mmol) and 2-bromothioanisole (1.6 mL, 12 mmol) in a mixture of ethylene glycol dimethyl ether (20 mL) and aqueous sodium carbonate (10 mL) was deoxygenated by a rapid stream of nitrogen applied to the system for 20 min, then treated with Pd(0) at once. The reaction was refluxed for 18 h, cooled down, filtered through Celite® and washed with THF (20 mL). The filtrate evaporated to dryness, taken up in water and extracted with EtOAc (3×). The EtOAc extracts were dried over sodium sulfate and concentrated. The crude residue was purified by flash chromatography (hexane/EtOAc, 1:3) to afford 5-[2-(methylthio)phenyl]-1H-indole (1.5 g, 52%).

The product (0.35 g, 1.5 mmol) was dissolved in acetic acid and treated with sodium cyanoborohydride (94 mg, 1.5 mmol). The reaction mixture was stirred for 4 h, concentrated and purified through a plug of silica gel (hexane/EtOAc, 1:1) to afford the desired product (170 mg, 46%). LRMS (ES+): 331.1 (M+H)+.

Example 3

2,3-Dihydro-5-[2-(1-pyrrolidinylmethyl)phenyl]-1H-indole

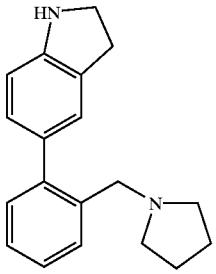

A mixture of N-BOC-indole (2.0 g, 6.7 mmol) and 2-formyl benzene boronic acid (1 g, 6.7 mmol) was diluted with THF (20 mL) and 2M sodium carbonate (10 mL), then deoxygenated by a rapid stream of nitrogen applied to the system for 20 min, followed by treatment with Pd(0). The reaction was refluxed for 18 h, cooled down, filtered through Celite® and washed with THF (20 mL). The filtrate evaporated to dryness, taken up in water, and extracted with EtOAc (3×). The EtOAc extracts were dried over sodium sulfate and concentrated. The crude residue (1 g, 1.5 mmol) was treated with sodium borohydride (0.14 g, 1.5 mmol) and pyrrolidine (0.3 mL, 1.5 mmol). The reaction mixture was stirred for 18 h, diluted with ice water and extracted with EtOAc. Ethyl acetate extracts were dried over sodium sulfate and concentrated. The crude residue was purified by flash chromatography (hexane/EtOAc, 1:3) to afford an intermediate indole (0.27 g), that was treated with TFA (10 mL) and sodium cyanoborohydride (43 mg, 0.7 mmol). The reaction mixture was stirred for 4 h, concentrated and purified through a plug of silica gel (hexane/EtOAc, 1:1) to afford the desired product (0.25 g, 29% over last 2 steps). LRMS (ES+): 279.2 (M+H)+.

Example 4

1-[[1-[3-Cyanophenyl]-3-(trifluoromethyl)-1H-pyrazol-5-yl]carbonyl]-5-[2-(aminosulfonyl)phenyl]-2,3-dihydro-1H-indole

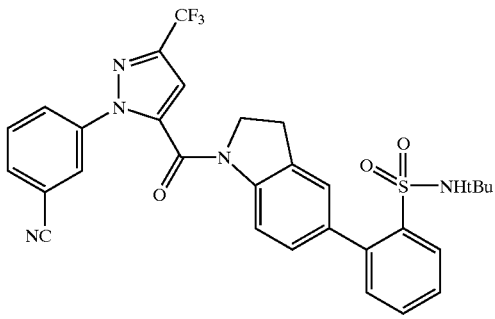

To the solution of 3-(trifluoromethyl)-1-(3-cyanophenyl)-1H-pyrazolecarboxylic acid (0.2 g, 0.6 mmol) in dry acetonitrile (10 mL) was added thionyl chloride (0.37 g, 1.8 mmol). The reaction mixture was warmed up to 50° C. for 1 h. The solvent and excess thionyl chloride were removed under reduced pressure and dried on a vacuum pump over 18 h. This residue was dissolved in THF and treated with a mixture of 2-(2,3-dihydro-1H-indol-5-yl)-N-(1,1-dimethylethyl)benzenesulfonamide from Example 1 (0.3 g, 0.8 mmol) in THF (5 mL) and NaH (72 mg, 1.6 mmol). The reaction mixture was allowed to stir at ambient temperature for 0.5 h, then quenched with water and extracted with EtOAc (3×). Ethyl acetate extracts were dried over sodium sulfate and concentrated. The crude residue was purified by flash chromatography (hexane/EtOAc, 1:3) to afford the title product (0.38 g, 92%). LRMS (ES+): 593.2 (M+H)+.

Example 5

1-[[1-[3-(Aminomethyl)phenyl]-3-(trifluoromethyl)-1H-pyrazol-5-yl]carbonyl]-5-[2-(aminosulfonyl)phenyl]-2,3-dihydro-1H-indole

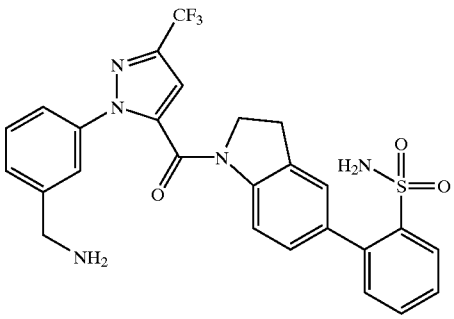

1-[[1-[3-Cyanophenyl]-3(trifluoromethyl)-1H-pyrazol-5-yl]carbonyl]-5-[2-(aminosulfonyl)phenyl]-2,3-dihydro-1H-indole (0.2 g, 0.34 mmol), prepared according to Example 4, was reduced under an atmosphere of hydrogen gas (55 psi) in methanol (5 mL) and trifluoroacetic acid in the presence of 10% palladium on carbon catalyst for 18 h at ambient temperature. The reaction mixture was filtered through a pad of Celite® and washed with methanol (3×). This product was treated with trifluoroacetic acid (1 mL) at 80° C. over 1 h, then purified by HPLC utilizing gradient elution with a mixture of water:acetonitrile with 0.05% of trifluoroacetic acid on a reverse phase C18 (60 angstrom) column to give the title product (28 mg, 15%). LRMS (ES+): 598.2 (M+H)+.

Example 6

1-[[1-[3-(Aminoiminomethyl)phenyl]-3-(trifluoromethyl)-1H-pyrazol-5-yl]carbonyl]-5-[2-(aminosulfonyl)phenyl]-2,3-dihydro-1H-indole

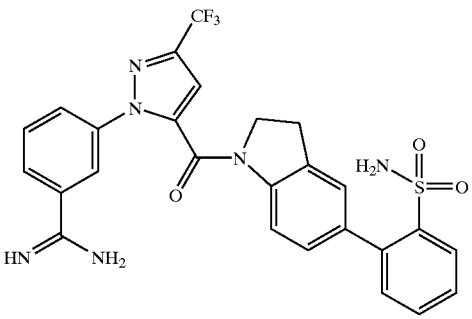

1-[[1-[3-Cyanophenyl]-3(trifluoromethyl)-1H-pyrazol-5-yl]carbonyl]-5-[2(aminosulfonyl)phenyl]-2,3-dihydro-1H-indole (0.2 g, 0.34 mmol), prepared according to Example 4, was placed in a mixture of chloroform and methanol (1:1, 10 mL), cooled to 0° C. and a stream of HCl gas was passed through the solution for 15 min. The resultant mixture was sealed and let to stand for 18 h at ambient temperature, then concentrated, diluted with methanol (5 mL), and treated with ammonium carbonate (1 g, excess). The resultant mixture was sealed and allowed to stand over 18 h at ambient temperature, then concentrated. The residue was purified by HPLC utilizing gradient elution with a mixture of water:acetonitrile with 0.05% of trifluoroacetic acid on a reverse phase C18 (60 angstrom) column to give the title product (30 mg, 16%). LRMS (ES+): 555.1 (M+H)+.

Example 7

1-[[1-[3-Cyano-4-fluorophenyl]-3(trifluoromethyl)-1H-pyrazol-5-yl]carbonyl]-5-[2(aminosulfonyl)phenyl]-2,3-dihydro-1H-indole

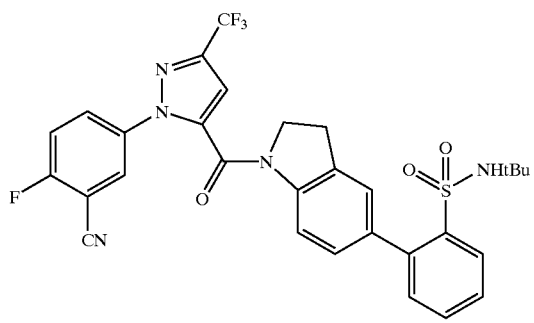

1-[[1-[3-Cyano-4-fluorophenyl]-3(trifluoromethyl)-1H-pyrazol-5-yl]carbonyl]-5-[2(aminosulfonyl)phenyl]-2,3-dihydro-1H-indole was prepared according to Example 4, LRMS (ES+): 610.1 (M+H)+.

Example 8

1-[[1-(3-Amino-1,2-benzisoxazol-5-yl)-3-(trifluoromethyl-1H-pyrazol-5-yl]carbonyl]-5-[2-(aminosulfonyl)phenyl]-2,3-dihydro-1H-indole

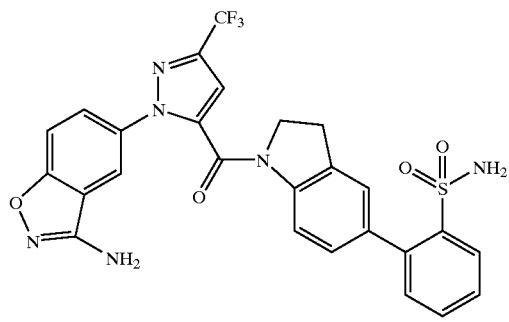

To a solution of acetone oxime (0.13 g, 1.8 mmol) in DMF (6 mL) was added 1-[[1-[3-cyano-4-fluorophenyl]-3(trifluoromethyl)-1H-pyrazol-5-yl]carbonyl]-5-[2(aminosulfonyl)phenyl]-2,3-dihydro-1H-indole (0.35 g, 0.57 mmol), prepared according to Example 7, in DMF (2 mL). The reaction was stirred at room temperature for 5 h, then partitioned between HCl (5%) and EtOAc, washed with water and brine, dried over sodium sulfate and concentrated. The crude residue was purified by flash chromatography (hexane/EtOAc, 1:3) to afford an intermediate (0.34 g, 89%). This product was dissolved in ethanol (5 mL) and HCl (20%, 5 mL). The reaction mixture was stirred at 80° C. for 3 h, cooled down and filtered. The precipitate was purified by HPLC utilizing gradient elution with a mixture of water:acetonitrile with 0.05% of trifluoroacetic acid on a reverse phase C18 (60 angstrom) column to give (42 mg, 13%). LRMS (ES+): 568.2 (M+H)+.

Example 9

1-[[1-(3-Amino-1,2-benzisoxazol-5-yl)-3-(trifluoromethyl)-1H-pyrazol-5-yl]carbonyl]-2,3-dihydro-5-[2-(methylsulfonyl)phenyl]-1H-indole

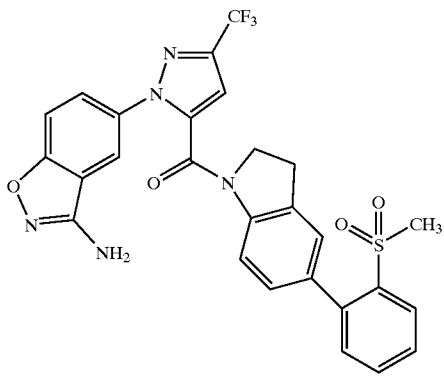

1-[[1-(3-Amino-1,2-benzisoxazol-5-yl)-3-(trifluoromethyl)-1H-pyrazol-5-yl]carbonyl]-2,3-dihydro-5-[2-(methylsulfonyl)phenyl]-1H-indole was prepared according to Example 8, followed by MCPBA oxidation (MCPBA (2 eq.), methylene chloride, ambient temperature, 20 h), LRMS (ES+): 567.6 (M+H)+.

Example 10

1-[[1-(3-Amino-1,2-benzisoxazol-5-yl)-3-(trifluoromethyl)-1H-pyrazol-5-yl]carbonyl]-2,3-dihydro-5-[2-(1-pyrrolidinylmethyl)phenyl]-1H-indole

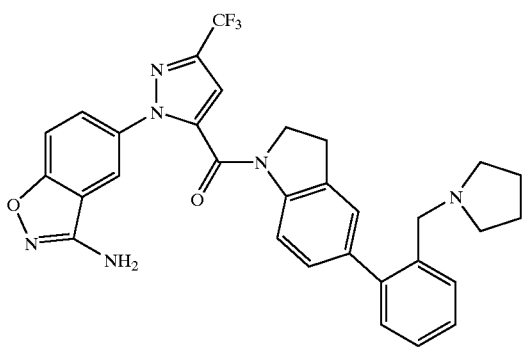

1-[[1-(3-Amino-1,2-benzisoxazol-5-yl)-3-(trifluoromethyl)-1H-pyrazol-5-yl]carbonyl]-2,3-dihydro-5-[2-(1-pyrrolidinylmethyl)phenyl]-1H-indole was prepared according to Example 8, LRMS (ES+): 568.5(M+H)+.

Example 11

1-[[1-(3-Amino-1,2-benzisoxazol-5-yl)-3-(trifluoromethyl)-1H-pyrazol-5-yl]carbonyl]-2,3-dihydro-5-[3-(1-pyrrolidinylmethyl)phenyl]-1H-indole

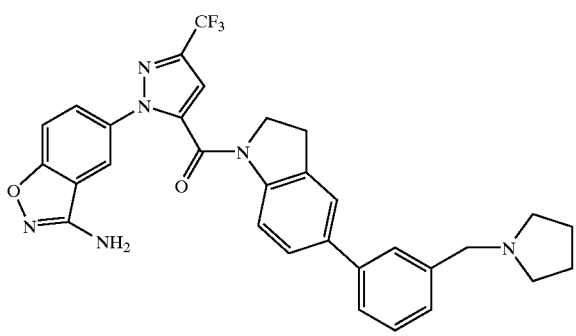

1-[[1-(3-Amino-1,2-benzisoxazol-5-yl)-3-(trifluoromethyl)-1H-pyrazol-5-yl]carbonyl]-2,3-dihydro-5-[3-(1-pyrrolidinylmethyl)phenyl]-1H-indole was prepared according to Examples 3 and 8, LRMS (ES+): 568.5(M+H)$^+$.

Example 12

1-[[1-(3-Amino-1,2-benzisoxazol-5-yl)-3-(trifluoromethyl)-1H-pyrazol-5-yl]carbonyl]-2,3-dihydro-5-[(2'-dimethylaminomethyl)imidazol-1-yl]-indoline

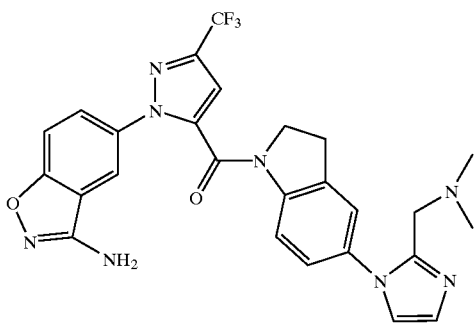

5-Bromoindoline (3.90 g, 19.7 mmol), (2'-dimethylaminomethyl)imidazole (2.95 g, 23.6 mmol), potassium carbonate (2.99 g, 21.7 mmol), 1,10-phenanthroline (177 mg, 5 mol %), and copper (I) iodide (187 mg, 5 mol %) were added together with 20 mL of DMSO. The mixture was degassed and then heated at 128° C. under N$_2$ for 16 h. The mixture was cooled and then poured into water. It was extracted with EtOAc, washed with brine, dried over MgSO$_4$, and concentrated. The crude mixture purified by chromatography (eluted with EtOAc then 10% MeOH n CH$_2$Cl$_2$) to give 0.90 g of 5-[(2'-dimethylaminomethyl)imidazol-1-yl]indoline (45%). MS (ES+): 243.2, M+H.

The title product was then prepared according to Examples 1, 4, and 8, LRMS (ES+): 537.5(M+H)$^+$.

Example 13

1-[[1-(3-Amino-1,2-benzisoxazol-5-yl)-3-(trifluoromethyl)-1H-pyrazol-5-yl]carbonyl]-2,3,4,5-tetrahydro-7-[2-(aminosulfonyl)phenyl]-benzazepine

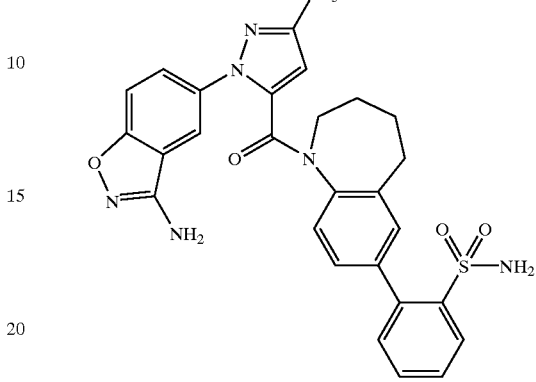

2-Amino-5-bromobenzoic acid (24.7 g, 11.4 mol) was dissolved in 350 mL of ethanol and 2, and 5 mL of concentrated H$_2$SO$_4$ was added. The mixture was refluxed under N$_2$ for 12 h. The solvent was removed and the residue was added with EtOAc. The mixture was extracted with 1N NaOH. The organic solution was washed with brine, dried over MgSO$_4$. It was concentrated and chromatographed with CH$_2$Cl$_2$ to give 3.19 g of 2-amino-5-bromobenzoic acid, ethyl ester. MS (AP+): 243.9, 246, M+H.

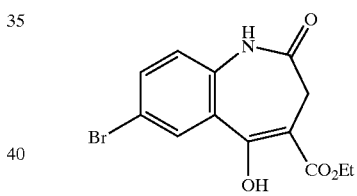

The above solid (3.18 g, 13.0 mmol) was dissolved in 50 mL of CH$_2$Cl$_2$. Triethylamine (1.91 mL, 13.7 mmol) was added followed by ethyl 4-chloro-4-oxobutyrate (1.86 mL, 13.1 mmol). The mixture was stirred at rt under N$_2$ for 12 h. It was then diluted with CH$_2$Cl$_2$ and washed with H$_2$O, 1N HCl, 1N NaOH, and brine. The organic mixture was dried over MgSO$_4$, concentrated, and chromatographed with CH$_2$Cl$_2$ to give 3.20 g of benzoic acid, 5-bromo-2-[(4-dioxo-4-propoxybutyl)amino]-ethyl ester. MS (AP+): 372, 379, M+H.

To a suspension of KH (4.00 g, 34.9 mmol) in 20 mL of toluene at 0° C. was added a solution of the above amide (2.17 g, 5.83 mmol) in 20 mL of toluene and 20 mL of DMF. After H$_2$ evolution stopped, the reaction mixture was heated at 70° C. for 3 h. The mixture was cooled to rt and 5 mL of glacial acetic acid was added followed by 20 mL of H$_2$O. The precipitate formed was filtered and air dried to give 0.93 g of the desired product.

The above solid (0.93 g, 2.85 mmol) was combined with H$_2$O (0.16 mL, 8.89 mmol) and DMSO (8 mL). The mixture was heated at 150° C. for 3 h under N$_2$. The mixture was poured into water and extracted with EtOAc. The organic solution was washed with brine, dried over MgSO$_4$, concentrated, and chromatographed with 0–50% EtOAc in hexane to give 0.44 g of 7-bromo-3,4-dihydro-1H-1-benzazepine-2,5-dione. MS (AP+): 295, 297, M+H.

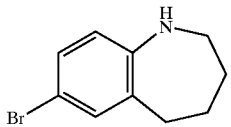

To a slurry of LAH (0.14 g, 3.69 mmol) in 10 mL of THF was added AlCl₃ (0.46 g, 3.45 mmol) in two portions. The mixture was stirred at rt for 15 minutes and a solution of 7-bromo-3,4-dihydro-1H-1-benzazepine-2,5-dione (0.22 g, 0.87 mmol) in 10 mL of THF was added dropwwase. The mixture was then heated at 60° C. for 12 h. The reaction was cooled and quenched. It was extracted with EtOAc. The organic solution was washed with brine, dried over MgSO₄, concentrated, and chromatographed with 20–100% EtOAc in hexane to give 0.07 g of 7-bromo-2,3,4,5-tetrahydro-1H-1-benzazepine. MS (AP+): 267, 269, M+H.

The title product was then prepared according to Examples 2 and 8. LRMS (ES+): 595.6 (M+H)⁺.

Example 14

1-[[1-(3-Amino-1,2-benzisoxazol-5-yl)-3-(trifluoromethyl)-1H-pyrazol-5-yl]carbonyl]-2,3-dihydro-6-[2-(methylsulfonyl)phenyl]-1H-quinolin-4-one

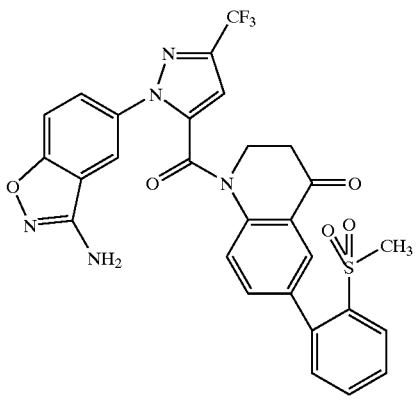

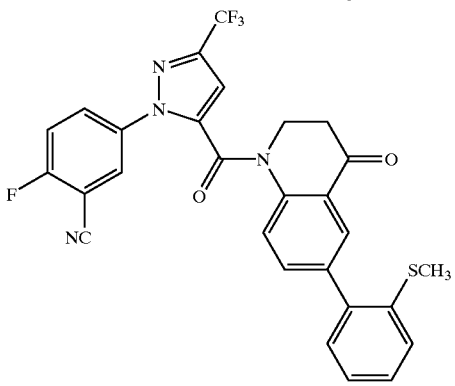

1-[[1-[3-Cyano-4-fluorophenyl]-3(trifluoromethyl)-1H-pyrazol-5-yl]carbonyl]-6-bromo-[2,3-dihydro-1H-quinolin-4-one] was prepared according to Example 4, LRMS (ES+): 494.1 (M+H)⁺. 1-[[1-[3-Cyano-4-fluorophenyl]-3(trifluoromethyl)-1H-pyrazol-5-yl]carbonyl]-2,3-dihydro-6-[2-(methylthio)phenyl]-1H-quinolin-4-one was then prepared according to Example 2, LRMS (ES+): 537.1 (M+H)⁺. The title product was then prepared according to Example 9, LRMS (ES+): 582.1 (M+H)⁺.

Example 15

1-[[1-(3-Amino-1,2-benzisoxazol-5-yl)-3-(trifluoromethyl)-1H-pyrazol-5-yl]carbonyl]-2,3-dihydro-6-[2-(methylsulfonyl)phenyl]-1H-quinoline

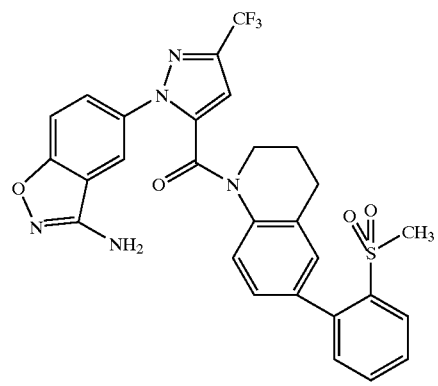

A solution of 6-bromo-2,3-dihydro-1H-quinolin-3-one (0.05 g, 0.219 mmol) in THF (20 mL) and aqueous sodium carbonate (5 mL) was treated with aluminum trichloride (0.116 g, 0.9 mmol) and lithium aluminum hydride (33 mg, 0.9 mmol) The reaction was refluxed for 18 h. and cooled down. The filtrate evaporated to dryness, taken up in water and extracted with EtOAc (3×). Ethyl acetate extracts were dried over sodium sulfate and concentrated. The crude residue was purified by flash chromatography (hexane/EtOAc, 1:3) to afford 6-bromo-2,3-dihydro-1H-quinoline (0.040 g, 87%). LRMS (ES+): 211.3 (M+H)⁺.

The title product was then prepared according to Example 14, LRMS (ES+): 568.2 (M+H)⁺.

Example 16

4-[[1-(3-Amino-1,2-benzisoxazol-5-yl)-3-(trifluoromethyl)-1H-pyrazol-5-yl]carbonyl]-2,3-dihydro-7-[2-(methylsulfonyl)phenyl]-2H-1,4-benzoxazine

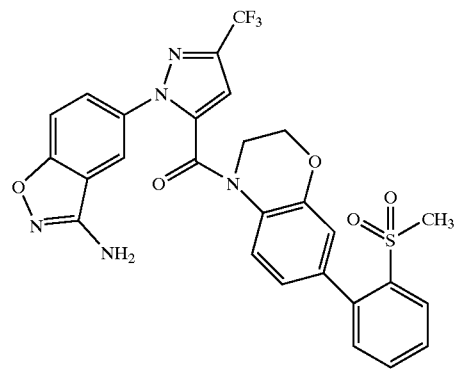

-continued

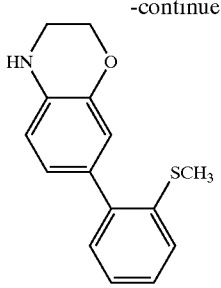

A solution of 7-bromo-1,4-benzoxazin-3-one (0.5 g, 2.2 mmol) and thioanisole-2-boronic acid (0.74 g, 2.2 mmol) in a mixture of ethylene glycol dimethyl ether (20 mL) and aqueous sodium carbonate (10 mL) was deoxygenated by a rapid stream of nitrogen applied to the system for 20 min, then treated with Pd(0) at once. The reaction was refluxed for 18 h, cooled down, filtered through Celite® and washed with THF (20 mL). The filtrate evaporated to dryness, taken up in water and extracted with EtOAc (3x). Ethyl acetate extracts were dried over sodium sulfate and concentrated. The crude residue was purified by flash chromatography (hexane/EtOAc, 1:3) to afford 2,3-dihydro-7-[2-(methylthio)phenyl]-1,4-benzoxazin-3-one (0.43 g, 72%). The product (0.2 g, 0.37 mmol) was dissolved in THP and treated with lithium aluminum hydride(56 mg, 0.8 mmol). The reaction mixture was refluxed for 1 h, concentrated and purified by a plug of silica gel (hexane/EtOAc, 1:1) to afford 2,3-dihydro-7-[2-(methylthio)phenyl]-1,4-benzoxazine (135 g, 71%). LRMS (ES+): 258.4 (M+H)$^+$.

The title product was then prepared according to Example 14, LRMS (ES+): 570.2 (M+H)$^+$.

Example 17

3-[[1-(3-Amino-1,2-benzisoxazol-5-yl)-3-(trifluoromethyl)-1H-pyrazol-5-yl]carbonyl]-4-[2-(methylsulfonyl)phenyl]indole

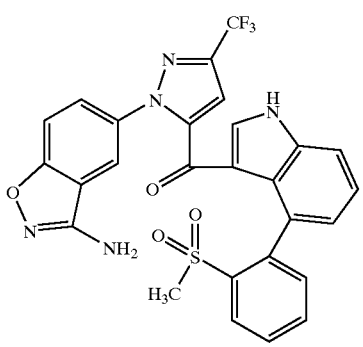

To the solution of 3-(trifluoromethyl)-1-(3-cyano-4-fluorophenyl)-1H-pyrazolecarboxylic

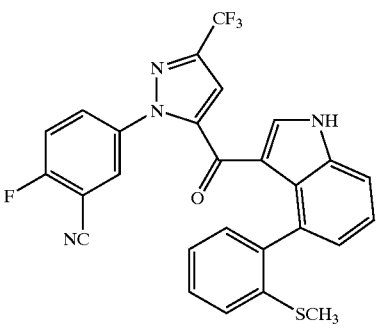

acid (0.3 g, 0.9 mmol) in dry acetonitrile (10 mL) was added thionyl chloride (0.74 g, 3.6 mmol). The reaction mixture was warmed up to 50° C. for 1 h. The solvent and excess thionyl chloride were removed under reduced pressure. The resulting material was dried on a vacuum pump for 18 h. This residue was dissolved in THF and treated with a mixture of 4-[2-(methylthio)phenyl]indole (prepared according to Example 2) (0.3 g, 0.8 mmol) in methylene chloride (5 mL) and aluminum trichloride (135 mg, 1.1 mmol). The reaction mixture was allowed to stir at ambient temperature for 5 h, then quenched with water and extracted with EtOAc (3x). EtOAc extracts were dried over sodium sulfate and concentrated. The crude residue was purified by flash chromatography (hexane/EtOAc, 1:3) to afford 1-[[1-[3-cyano-4-fluorophenyl]-3(trifluoromethyl)-1H-pyrazol-5-yl]carbonyl]-4-[2-(methylthio)phenyl]-3-indole (0.17 g, 34%). LRMS (ES+): 521.2 (M+H)$^+$.

The title product was then prepared according to

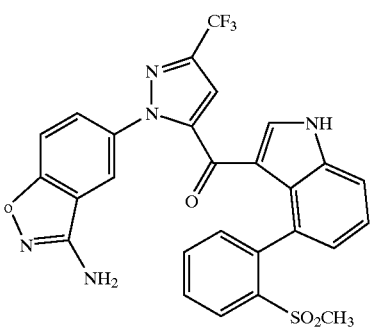

Example 9, LRMS (ES+): 501.4 (M+H)$^+$.

The following tables contain representative examples of the present invention. Each entry in each table is intended to be paired with each formulae at the start of the table. For example, in Tables 1 and 2, example 1 is intended to be paired with each of the formulae.

The following nomenclature is intended for group A in the following tables.

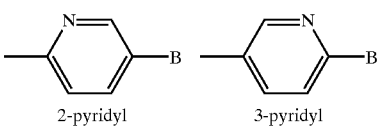

2-pyridyl      3-pyridyl

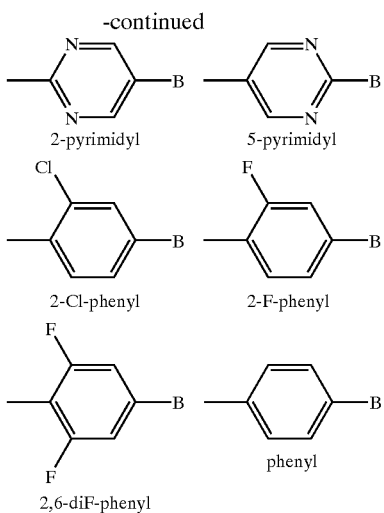
TABLE 1
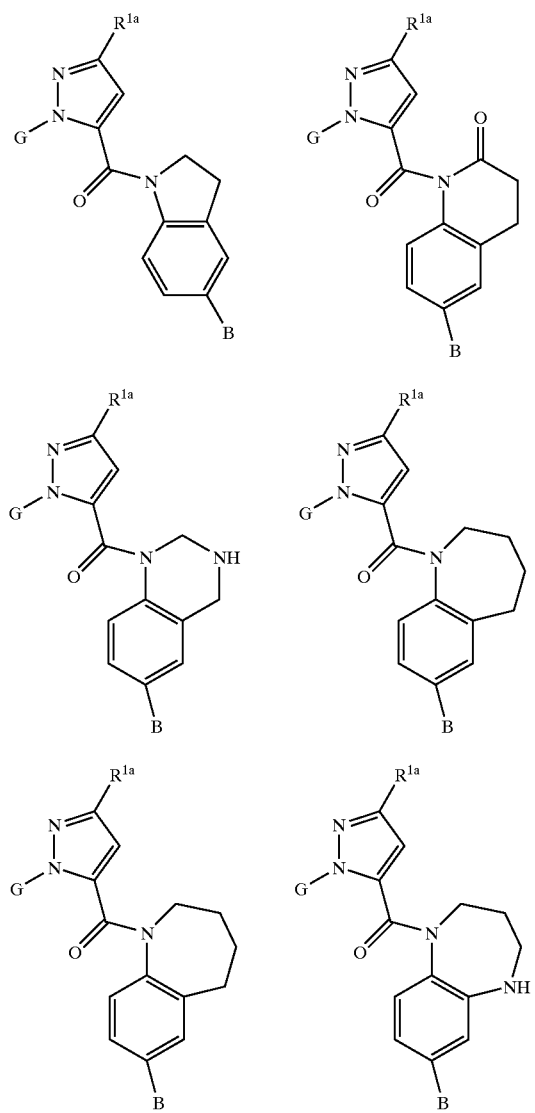
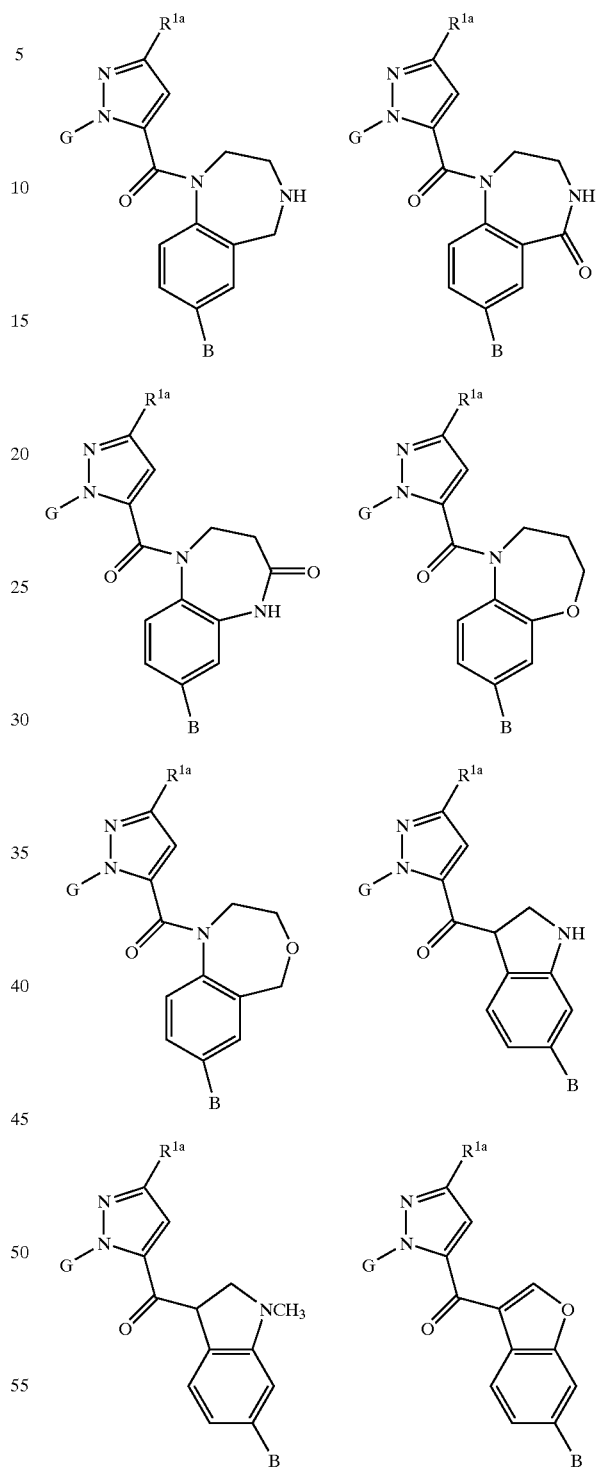
G is selected from:
4-(methoxy)phenyl;
2-(aminomethyl)phenyl;
3-(aminomethyl)phenyl;
2-(aminomethyl)-3-fluorophenyl;
2-(aminomethyl)-4-fluorophenyl;
2-(aminomethyl)-5-fluorophenyl;
2-(aminomethyl)-6-fluorophenyl;
3-amino-phthalazin-5-yl;

TABLE 1-continued 3-amino-phthalazin-6-yl;
1-aminoisoquinolin-7-yl;
4-aminoquinazol-6-yl;
3-aminobenzisoxazol-5-yl; and,
3-aminoisobenzazol-5-yl;

| Ex # | R¹ᵃ | B |
|---|---|---|
| 1. | CH3 | 2-(aminosulfonyl)phenyl |
| 2. | CH3 | 2-(methylaminosulfonyl)phenyl |
| 3. | CH3 | 1-pyrrolidinocarbonyl |
| 4. | CH3 | 2-(methylsulfonyl)phenyl |
| 5. | CH3 | 2-(N,N-dimethylaminomethyl)phenyl |
| 6. | CH3 | 2-(N-pyrrolidinylmethyl)phenyl |
| 7. | CH3 | 1-methyl-2-imidazolyl |
| 8. | CH3 | 2-methyl-1-imidazolyl |
| 9. | CH3 | 2-(dimethylaminomethyl)-1-imidazolyl |
| 10. | CH3 | 2-(N-(cyclopropyl-methyl)aminomethyl)phenyl |
| 11. | CH3 | 2-(N-(cyclobutyl)-aminomethyl)phenyl |
| 12. | CH3 | 2-(N-(cyclopentyl)-aminomethyl)phenyl |
| 13. | CH3 | 2-(N-(3-hydroxypyrrolidinyl)-methyl)phenyl |
| 14. | CH3 | 2-(isopropylaminomethyl)phenyl |
| 15. | CH3 | 4-azabenzimidazol-1-yl |
| 16. | CH3 | 5-azabenzimidazol-1-yl |
| 17. | CH3 | 6-azabenzimidazol-1-yl |
| 18. | CH3 | 7-azabenzimidazol-1-yl |
| 19. | CH2CH3 | 2-(aminosulfonyl)phenyl |
| 20. | CH2CH3 | 2-(methylaminosulfonyl)phenyl |
| 21. | CH2CH3 | 1-pyrrolidinocarbonyl |
| 22. | CH2CH3 | 2-(methylsulfonyl)phenyl |
| 23. | CH2CH3 | 2-(N,N-dimethylaminomethyl)phenyl |
| 24. | CH2CH3 | 2-(N-pyrrolidinylmethyl)phenyl |
| 25. | CH2CH3 | 1-methyl-2-imidazolyl |
| 26. | CH2CH3 | 2-methyl-1-imidazolyl |
| 27. | CH2CH3 | 2-(dimethylaminomethyl)-1-imidazolyl |
| 28. | CH2CH3 | 2-(N-(cyclopropyl-methyl)aminomethyl)phenyl |
| 29. | CH2CH3 | 2-(N-(cyclobutyl)-aminomethyl)phenyl |
| 30. | CH2CH3 | 2-(N-(cyclopentyl)-aminomethyl)phenyl |
| 31. | CH2CH3 | 2-(N-(3-hydroxypyrrolidinyl)-methyl)phenyl |
| 32. | CH2CH3 | 2-(isopropylaminomethyl)phenyl |
| 33. | CH2CH3 | 4-azabenzimidazol-1-yl |
| 34. | CH2CH3 | 5-azabenzimidazol-1-yl |
| 35. | CH2CH3 | 6-azabenzimidazol-1-yl |
| 36. | CH2CH3 | 7-azabenzimidazol-1-yl |
| 37. | CF3 | 2-(aminosulfonyl)phenyl |
| 38. | CF3 | 2-(methylaminosulfonyl)phenyl |
| 39. | CF3 | 1-pyrrolidinocarbonyl |
| 40. | CF3 | 2-(methylsulfonyl)phenyl |
| 41. | CF3 | 2-(N,N-dimethylaminomethyl)phenyl |
| 42. | CF3 | 2-(N-pyrrolidinylmethyl)phenyl |
| 43. | CF3 | 1-methyl-2-imidazolyl |
| 44. | CF3 | 2-methyl-1-imidazolyl |
| 45. | CF3 | 2-(dimethylaminomethyl)-1-imidazolyl |
| 46. | CF3 | 2-(N-(cyclopropyl-methyl)aminomethyl)phenyl |
| 47. | CF3 | 2-(N-(cyclobutyl)-aminomethyl)phenyl |
| 48. | CF3 | 2-(N-(cyclopentyl)-aminomethyl)phenyl |
| 49. | CF3 | 2-(N-(3-hydroxypyrrolidinyl)-methyl)phenyl |
| 50. | CF3 | 2-(isopropylaminomethyl)phenyl |
| 51. | CF3 | 4-azabenzimidazol-1-yl |
| 52. | CF3 | 5-azabenzimidazol-1-yl |
| 53. | CF3 | 6-azabenzimidazol-1-yl |
| 54. | CF3 | 7-azabenzimidazol-1-yl |
| 55. | SCH3 | 2-(aminosulfonyl)phenyl |
| 56. | SCH3 | 2-(methylaminosulfonyl)phenyl |
| 57. | SCH3 | 1-pyrrolidinocarbonyl |
| 58. | SCH3 | 2-(methylsulfonyl)phenyl |
| 59. | SCH3 | 2-(N,N-dimethylaminomethyl)phenyl |
| 60. | SCH3 | 2-(N-pyrrolidinylmethyl)phenyl |
| 61. | SCH3 | 1-methyl-2-imidazolyl |
| 62. | SCH3 | 2-methyl-1-imidazolyl |
| 63. | SCH3 | 2-(dimethylaminomethyl)-1-imidazolyl |
| 64. | SCH3 | 2-(N-(cyclopropyl-methyl)aminomethyl)phenyl |
| 65. | SCH3 | 2-(N-(cyclobutyl)-aminomethyl)phenyl |
| 66. | SCH3 | 2-(N-(cyclopentyl)-aminomethyl)phenyl |
| 67. | SCH3 | 2-(N-(3-hydroxypyrrolidinyl)-methyl)phenyl |
| 68. | SCH3 | 2-(isopropylaminomethyl)phenyl |
| 69. | SCH3 | 4-azabenzimidazol-1-yl |
| 70. | SCH3 | 5-azabenzimidazol-1-yl |
| 71. | SCH3 | 6-azabenzimidazol-1-yl |
| 72. | SCH3 | 7-azabenzimidazol-1-yl |
| 73. | SOCH3 | 2-(aminosulfonyl)phenyl |
| 74. | SOCH3 | 2-(methylaminosulfonyl)phenyl |
| 75. | SOCH3 | 1-pyrrolidinocarbonyl |
| 76. | SOCH3 | 2-(methylsulfonyl)phenyl |
| 77. | SOCH3 | 2-(N,N-dimethylaminomethyl)phenyl |
| 78. | SOCH3 | 2-(N-pyrrolidinylmethyl)phenyl |
| 79. | SOCH3 | 1-methyl-2-imidazolyl |
| 80. | SOCH3 | 2-methyl-1-imidazolyl |
| 81. | SOCH3 | 2-(dimethylaminomethyl)-1-imidazolyl |
| 82. | SOCH3 | 2-(N-(cyclopropyl-methyl)aminomethyl)phenyl |
| 83. | SOCH3 | 2-(N-(cyclobutyl)-aminomethyl)phenyl |
| 84. | SOCH3 | 2-(N-(cyclopentyl)-aminomethyl)phenyl |
| 85. | SOCH3 | 2-(N-(3-hydroxypyrrolidinyl)-methyl)phenyl |
| 86. | SOCH3 | 2-(isopropylaminomethyl)phenyl |
| 87. | SOCH3 | 4-azabenzimidazol-1-yl |
| 88. | SOCH3 | 5-azabenzimidazol-1-yl |
| 89. | SOCH3 | 6-azabenzimidazol-1-yl |
| 90. | SOCH3 | 7-azabenzimidazol-1-yl |
| 91. | SO2CH3 | 2-(aminosulfonyl)phenyl |
| 92. | SO2CH3 | 2-(methylaminosulfonyl)phenyl |
| 93. | SO2CH3 | 1-pyrrolidinocarbonyl |
| 94. | SO2CH3 | 2-(methylsulfonyl)phenyl |
| 95. | SO2CH3 | 2-(N,N-dimethylaminomethyl)phenyl |
| 96. | SO2CH3 | 2-(N-pyrrolidinylmethyl)phenyl |
| 97. | SO2CH3 | 1-methyl-2-imidazolyl |
| 98. | SO2CH3 | 2-methyl-1-imidazolyl |
| 99. | SO2CH3 | 2-(dimethylaminomethyl)-1-imidazolyl |
| 100. | SO2CH3 | 2-(N-(cyclopropyl-methyl)aminomethyl)phenyl |
| 101. | SO2CH3 | 2-(N-(cyclobutyl)-aminomethyl)phenyl |
| 102. | SO2CH3 | 2-(N-(cyclopentyl)-aminomethyl)phenyl |
| 103. | SO2CH3 | 2-(N-(3-hydroxypyrrolidinyl)-methyl)phenyl |
| 104. | SO2CH3 | 2-(isopropylaminomethyl)phenyl |
| 105. | SO2CH3 | 4-azabenzimidazol-1-yl |
| 106. | SO2CH3 | 5-azabenzimidazol-1-yl |
| 107. | SO2CH3 | 6-azabenzimidazol-1-yl |
| 108. | SO2CH3 | 7-azabenzimidazol-1-yl |
| 109. | Cl | 2-(aminosulfonyl)phenyl |
| 110. | Cl | 2-(methylaminosulfonyl)phenyl |
| 111. | Cl | 1-pyrrolidinocarbonyl |
| 112. | Cl | 2-(methylsulfonyl)phenyl |
| 113. | Cl | 2-(N,N-dimethylaminomethyl)phenyl |
| 114. | Cl | 2-(N-pyrrolidinylmethyl)phenyl |
| 115. | Cl | 1-methyl-2-imidazolyl |
| 116. | Cl | 2-methyl-1-imidazolyl |
| 117. | Cl | 2-(dimethylaminomethyl)-1-imidazolyl |
| 118. | Cl | 2-(N-(cyclopropyl-methyl)aminomethyl)phenyl |
| 119. | Cl | 2-(N-(cyclobutyl)-aminomethyl)phenyl |
| 120. | Cl | 2-(N-(cyclopentyl)-aminomethyl)phenyl |
| 121. | Cl | 2-(N-(3-hydroxypyrrolidinyl)-methyl)phenyl |
| 122. | Cl | 2-(isopropylaminomethyl)phenyl |
| 123. | Cl | 4-azabenzimidazol-1-yl |
| 124. | Cl | 5-azabenzimidazol-1-yl |
| 125. | Cl | 6-azabenzimidazol-1-yl |
| 126. | Cl | 7-azabenzimidazol-1-yl |
| 127. | F | 2-(aminosulfonyl)phenyl |
| 128. | F | 2-(methylaminosulfonyl)phenyl |
| 129. | F | 1-pyrrolidinocarbonyl |
| 130. | F | 2-(methylsulfonyl)phenyl |
| 131. | F | 2-(N,N-dimethylaminomethyl)phenyl |
| 132. | F | 2-(N-pyrrolidinylmethyl)phenyl |
| 133. | F | 1-methyl-2-imidazolyl |
| 134. | F | 2-methyl-1-imidazolyl |
| 135. | F | 2-(dimethylaminomethyl)-1-imidazolyl |
| 136. | F | 2-(N-(cyclopropyl-methyl)aminomethyl)phenyl |
| 137. | F | 2-(N-(cyclobutyl)-aminomethyl)phenyl |
| 138. | F | 2-(N-(cyclopentyl)-aminomethyl)phenyl |
| 139. | F | 2-(N-(3-hydroxypyrrolidinyl)-methyl)phenyl |
| 140. | F | 2-(isopropylaminomethyl)phenyl |
| 141. | F | 4-azabenzimidazol-1-yl |
| 142. | F | 5-azabenzimidazol-1-yl |
| 143. | F | 6-azabenzimidazol-1-yl |
| 144. | F | 7-azabenzimidazol-1-yl |
| 145. | CO2CH3 | 2-(N-pyrrolidinylmethyl)phenyl |
| 146. | CO2CH3 | 1-methyl-2-imidazolyl |
| 147. | CO2CH3 | 2-methyl-1-imidazolyl |
| 148. | CO2CH3 | 2-(dimethylaminomethyl)-1-imidazolyl |
| 149. | CO2CH3 | 2-(N-(cyclopropyl-methyl)aminomethyl)phenyl |
| 150. | CO2CH3 | 2-(N-(cyclobutyl)-aminomethyl)phenyl |
| 151. | CO2CH3 | 2-(N-(cyclopentyl)-aminomethyl)phenyl |

TABLE 1-continued

| | | |
|---|---|---|
| 152. | CO2CH3 | 2-(N-(3-hydroxypyrrolidinyl)-methyl)phenyl |
| 153. | CO2CH3 | 2-(isopropylaminomethyl)phenyl |
| 154. | CO2CH3 | 4-azabenzimidazol-1-yl |
| 155. | CO2CH3 | 5-azabenzimidazol-1-yl |
| 156. | CO2CH3 | 6-azabenzimidazol-1-yl |
| 157. | CO2CH3 | 7-azabenzimidazol-1-yl |
| 158. | CH2OCH3 | 2-(aminosulfonyl)phenyl |
| 159. | CH2OCH3 | 2-(methylaminosulfonyl)phenyl |
| 160. | CH2OCH3 | 1-pyrrolidinocarbonyl |
| 161. | CH2OCH3 | 2-(methylsulfonyl)phenyl |
| 162. | CH2OCH3 | 2-(N,N-dimethylaminomethyl)phenyl |
| 163. | CH2OCH3 | 2-(N-pyrrolidinylmethyl)phenyl |
| 164. | CH2OCH3 | 1-methyl-2-imidazolyl |
| 165. | CH2OCH3 | 2-methyl-1-imidazolyl |
| 166. | CH2OCH3 | 2-(dimethylaminomethyl)-1-imidazolyl |
| 167. | CH2OCH3 | 2-(N-(cyclopropyl-methyl)aminomethyl)phenyl |
| 168. | CH2OCH3 | 2-(N-(cyclobutyl)-aminomethyl)phenyl |
| 169. | CH2OCH3 | 2-(N-(cyclopentyl)-aminomethyl)phenyl |
| 170. | CH2OCH3 | 2-(N-(3-hydroxypyrrolidinyl)-methyl)phenyl |
| 171. | CH2OCH3 | 2-(isopropylaminomethyl)phenyl |
| 172. | CH2OCH3 | 4-azabenzimidazol-1-yl |
| 173. | CH2OCH3 | 5-azabenzimidazol-1-yl |
| 174. | CH2OCH3 | 6-azabenzimidazol-1-yl |
| 175. | CH2OCH3 | 7-azabenzimidazol-1-yl |
| 176. | CONH2 | 2-(aminosulfonyl)phenyl |
| 177. | CONH2 | 2-(methylaminosulfonyl)phenyl |
| 178. | CONH2 | 1-pyrrolidinocarbonyl |
| 179. | CONH2 | 2-(methylsulfonyl)phenyl |
| 180. | CONH2 | 2-(N,N-dimethylaminomethyl)phenyl |
| 181. | CONH2 | 2-(N-pyrrolidinylmethyl)phenyl |
| 182. | CONH2 | 1-methyl-2-imidazolyl |
| 183. | CONH2 | 2-methyl-1-imidazolyl |
| 184. | CONH2 | 2-(dimethylaminomethyl)-1-imidazolyl |
| 185. | CONH2 | 2-(N-(cyclopropyl-methyl)aminomethyl)phenyl |
| 186. | CONH2 | 2-(N-(cyclobutyl)-aminomethyl)phenyl |
| 187. | CONH2 | 2-(N-(cyclopentyl)-aminomethyl)phenyl |
| 188. | CONH2 | 2-(N-(3-hydroxypyrrolidinyl)-methyl)phenyl |
| 189. | CONH2 | 2-(isopropylaminomethyl)phenyl |
| 190. | CONH2 | 4-azabenzimidazol-1-yl |
| 191. | CONH2 | 5-azabenzimidazol-1-yl |
| 192. | CONH2 | 6-azabenzimidazol-1-yl |
| 193. | CONH2 | 7-azabenzimidazol-1-yl |
| 194. | CN | 2-(aminosulfonyl)phenyl |
| 195. | CN | 2-(methylaminosulfonyl)phenyl |
| 196. | CN | 1-pyrrolidinocarbonyl |
| 197. | CN | 2-(methylsulfonyl)phenyl |
| 198. | CN | 2-(N,N-dimethylaminomethyl)phenyl |
| 199. | CN | 2-(N-pyrrolidinylmethyl)phenyl |
| 200. | CN | 1-methyl-2-imidazolyl |
| 201. | CN | 2-methyl-1-imidazolyl |
| 202. | CN | 2-(dimethylaminomethyl)-1-imidazolyl |
| 203. | CN | 2-(N-(cyclopropyl-methyl)aminomethyl)phenyl |
| 204. | CN | 2-(N-(cyclobutyl)-aminomethyl)phenyl |
| 205. | CN | 2-(N-(cyclopentyl)-aminomethyl)phenyl |
| 206. | CN | 2-(N-(3-hydroxypyrrolidinyl)-methyl)phenyl |
| 207. | CN | 2-(isopropylaminomethyl)phenyl |
| 208. | CN | 4-azabenzimidazol-1-yl |
| 209. | CN | 5-azabenzimidazol-1-yl |
| 210. | CN | 6-azabenzimidazol-1-yl |
| 211. | CN | 7-azabenzimidazol-1-yl |
| 212. | CH2NH2 | 2-(N-pyrrolidinylmethyl)phenyl |
| 213. | CH2NH2 | 1-methyl-2-imidazolyl |
| 214. | CH2NH2 | 2-methyl-1-imidazolyl |
| 215. | CH2NH2 | 2-(dimethylaminomethyl)-1-imidazolyl |
| 216. | CH2NH2 | 2-(N-(cyclopropyl-methyl)aminomethyl)phenyl |
| 217. | CH2NH2 | 2-(N-(cyclobutyl)-aminomethyl)phenyl |
| 218. | CH2NH2 | 2-(N-(cyclopentyl)-aminomethyl)phenyl |
| 219. | CH2NH2 | 2-(N-(3-hydroxypyrrolidinyl)-methyl)phenyl |
| 220. | CH2NH2 | 2-(isopropylaminomethyl)phenyl |
| 221. | CH2NH2 | 4-azabenzimidazol-1-yl |
| 222. | CH2NH2 | 5-azabenzimidazol-1-yl |
| 223. | CH2NH2 | 6-azabenzimidazol-1-yl |
| 224. | CH2NH2 | 7-azabenzimidazol-1-yl |
| 225. | CH2NHSO2CH3 | 2-(aminosulfonyl)phenyl |
| 226. | CH2NHSO2CH3 | 2-(methylaminosulfonyl)phenyl |
| 227. | CH2NHSO2CH3 | 1-pyrrolidinocarbonyl |
| 228. | CH2NHSO2CH3 | 2-(methylsulfonyl)phenyl |
| 229. | CH2NHSO2CH3 | 2-(N,N-dimethylaminomethyl)phenyl |
| 230. | CH2NHSO2CH3 | 2-(N-pyrrolidinylmethyl)phenyl |

TABLE 1-continued

| | | |
|---|---|---|
| 231. | CH2NHSO2CH3 | 1-methyl-2-imidazolyl |
| 232. | CH2NHSO2CH3 | 2-methyl-1-imidazolyl |
| 233. | CH2NHSO2CH3 | 2-(dimethylaminomethyl)-1-imidazolyl |
| 234. | CH2NHSO2CH3 | 2-(N-(cyclopropyl-methyl)aminomethyl)phenyl |
| 235. | CH2NHSO2CH3 | 2-(N-(cyclobutyl)-aminomethyl)phenyl |
| 236. | CH2NHSO2CH3 | 2-(N-(cyclopentyl)-aminomethyl)phenyl |
| 237. | CH2NHSO2CH3 | 2-(N-(3-hydroxypyrrolidinyl)-methyl)phenyl |
| 238. | CH2NHSO2CH3 | 2-(isopropylaminomethyl)phenyl |
| 239. | CH2NHSO2CH3 | 4-azabenzimidazol-1-yl |
| 240. | CH2NHSO2CH3 | 5-azabenzimidazol-1-yl |
| 241. | CH2NHSO2CH3 | 6-azabenzimidazol-1-yl |
| 242. | CH2NHSO2CH3 | 7-azabenzimidazol-1-yl |

TABLE 2

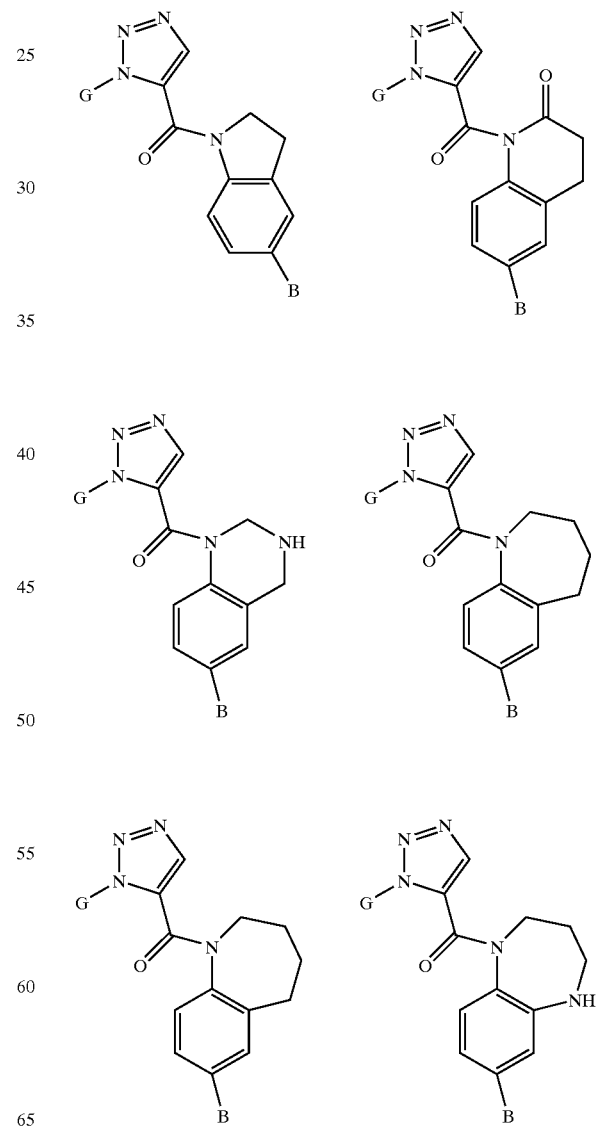

TABLE 2-continued

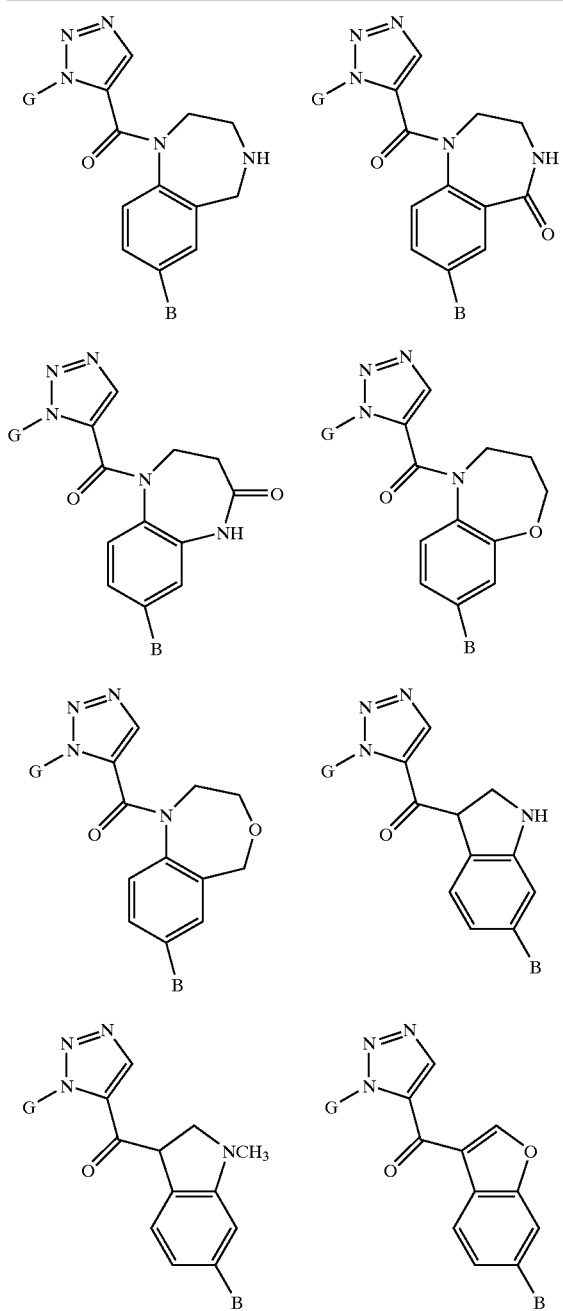

G is selected from:
4-(methoxy)phenyl;
2-(aminomethyl)phenyl;
3-(aminomethyl)phenyl;
2-(aminomethyl)-3-fluorophenyl;
2-(aminomethyl)-4-fluorophenyl;
2-(aminomethyl)-5-fluorophenyl;
2-(aminomethyl)-6-fluorophenyl;
3-amino-phthalazin-5-yl;
3-amino-phthalazin-6-yl;
1-aminoisoquinolin-7-yl;
4-aminoquinazol-6-yl;
3-aminobenzisoxazol-5-yl; and,
3-aminoisobenzazol-5-yl;
Ex #   B TABLE 2-continued

| | |
|---|---|
| 1. | 2-(aminosulfonyl)phenyl |
| 2. | 2-(methylaminosulfonyl)phenyl |
| 3. | 1-pyrrolidinocarbonyl |
| 4. | 2-(methylsulfonyl)phenyl |
| 5. | 2-(N,N-dimethylaminomethyl)phenyl |
| 6. | 2-(N-pyrrolidinylmethyl)phenyl |
| 7. | 1-methyl-2-imidazolyl |
| 8. | 2-methyl-1-imidazolyl |
| 9. | 2-(dimethylaminomethyl)-1-imidazolyl |
| 10. | 2-(N-(cyclopropyl-methyl)aminomethyl)phenyl |
| 11. | 2-(N-(cyclobutyl)-aminomethyl)phenyl |
| 12. | 2-(N-(cyclopentyl)-aminomethyl)phenyl |
| 13. | 2-(N-(3-hydroxypyrrolidinyl)-methyl)phenyl |
| 14. | 2-(isopropylaminomethyl)phenyl |
| 15. | 4-azabenzimidazol-1-yl |
| 16. | 5-azabenzimidazol-1-yl |
| 17. | 6-azabenzimidazol-1-yl |
| 18. | 7-azabenzimidazol-1-yl |

Obviously, numerous modifications and variations of the present invention are possible in light of the above teachings. It is therefore to be understood that within the scope of the appended claims, the invention may be practiced otherwise that as specifically described herein.

What is claimed is:

1. A compound of formula B:

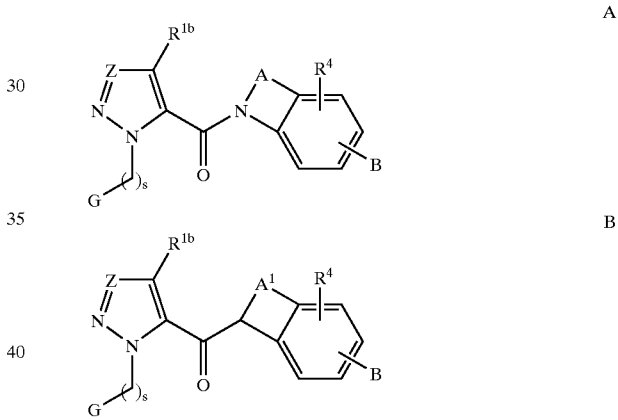

or a stereoisomer or pharmaceutically acceptable salt thereof;

G is a group of formula I or II:

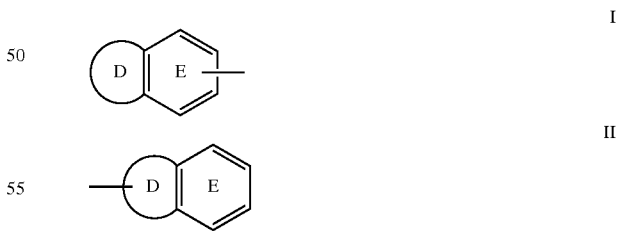

ring D is selected from $-(CH_2)_3-$, $-(CH_2)_4-$, $-CH_2N=CH-$, $-CH_2CH_2N=CH-$, and a 5–6 membered aromatic system containing from 0–2 heteroatoms selected from the group N, O, and S;

ring D, when present, is substituted with 0–2 R, provided that when ring D is unsubstituted, it contains at least one heteroatom;

E is selected from phenyl, pyridyl, pyrimidyl, pyrazinyl, and pyridazinyl, substituted with 0–1 R;

R is selected from Cl, F, Br, I, OH, $C_{1-3}$ alkoxy, $NH_2$, $NH(C_{1-3}$ alkyl), $N(C_{1-3}$ alkyl$)_2$, $CH_2NH_2$, $CH_2NH(C_{1-3}$ alkyl), $CH_2N(C_{1-3}$ alkyl$)_2$, $CH_2CH_2NH_2$, $CH_2CH_2NH(C_{1-3}$ alkyl), and $CH_2CH_2N(C_{1-3}$ alkyl$)_2$;

alternatively, ring D is absent;

when ring D is absent, ring E is selected from phenyl, pyridyl, pyrimidyl, pyrazinyl, and pyridazinyl, and ring E is substituted with $R^a$ and $R^b$;

$R^a$ is selected from H, F, Cl, Br, I, $SR^3$, $CO_2R^3$, $NO_2$, $(CH_2)_tOR^3$, $C_{1-4}$ alkyl, $OCF_3$, $CF_3$, $C(O)NR^7R^8$, and $(CR^8R^9)_tNR^7R^8$;

$R^b$ is selected from F, Cl, Br, I, OH, $C_{1-3}$ alkoxy, CN, $C(=NR^8)NR^7R^9$, $NHC(=NR^8)NR^7R^9$, $NR^8CH(=NR^7)$, $C(O)NR^7R^8$, $(CR^8R^9)_tNR^7R^8$, SH, $C_{1-3}$ alkyl-S, $S(O)R^{3b}$, $S(O)_2R^{3a}$, $S(O)_2NR^2R^{2a}$, $OCF_3$, and a 5–6 membered heteroaromatic system containing from 1–4 heteroatoms selected from the group N, O, and S and substituted with $R^c$;

alternatively, $R^a$ and $R^b$ combine to form methylenedioxy or ethylenedioxy;

$R^c$ is selected from OH, SH, $C_{1-3}$ alkoxy, $C_{1-3}$ thioalkoxy, $NH_2$, $NH(C_{1-3}$ alkyl), $N(C_{1-3}$ alkyl$)_2$, $CH_2NH_2$, $CH_2NH(C_{1-3}$ alkyl), $CH_2N(C_{1-3}$ alkyl$)_2$, $CH_2CH_2NH_2$, $CH_2CH_2NH(C_{1-3}$ alkyl), and $CH_2CH_2N(C_{1-3}$ alkyl$)_2$;

Z is N or $CR^{1a}$;

$R^{1a}$ is absent or selected from $—(CH_2)_r—R^{1c}$, $—CH=CH—R^{1c}$, $NCH_2R^{1d}$, $OCH_2R^{1d}$, $SCH_2R^{1d}$, $NH(CH_2)_2(CH_2)_rR^{1c}$, $O(CH_2)_2(CH_2)_rR^{1c}$, and $S(CH_2)_2(CH_2)_rR^{1c}$;

$R^{1b}$ is absent or selected from $—(CH_2)_r—R^{1c}$, $—CH=CH—R^{1c}$, $NCH_2R^{1d}$, $OCH_2R^{1d}$, $SCH_2R^{1d}$, $NH(CH_2)_2(CH_2)_rR^{1c}$, $O(CH_2)_2(CH_2)_rR^{1c}$, and $S(CH_2)_2(CH_2)_rR^{1c}$;

alternatively, $R^{1a}$ and $R^{1b}$, when both are present, together with the atoms to which they are attached form a 5–8 membered saturated, partially saturated or unsaturated ring substituted with 0–2 $R^4$ and which contains from 0–2 heteroatoms selected from the group consisting of N, O, and S;

$R^{1c}$ is selected from H, $C_{1-3}$ alkyl, F, Cl, Br, I, —CN, —CHO, $(CF_2)_rCF_3$, $(CH_2)_rOR^2$, $NR^2R^{2a}$, $C(O)R^{2c}$, $OC(O)R^2$, $(CF_2)_rCO_2R^{2c}$, $S(O)_pR^{2b}$, $NR^2(CH_2)_rOR^2$, $CH(=NR^{2c})NR^2R^{2a}$, $NR^2C(O)R^{2b}$, $NR^2C(O)NHR^{2b}$, $NR^2C(O)_2R^{2a}$, $OC(O)NR^{2a}R^{2b}$, $C(O)NR^2R^{2a}$, $C(O)NR^2(CH_2)_rOR^2$, $SO_2NR^2R^{2a}$, $NR^2SO_2R^{2b}$, $C_{3-6}$ carbocyclic residue substituted with 0–2 $R^4$, and 5–10 membered heterocyclic system containing from 1–4 heteroatoms selected from the group consisting of N, O, and S substituted with 0–2 $R^4$;

$R^{1d}$ is selected from H, $CH(CH_2OR^2)_2$, $C(O)R^{2c}$, $C(O)NR^2R^{2a}$, $S(O)R^{2b}$, $S(O)_2R^{2b}$, and $SO_2NR^2R^{2a}$;

$R^2$, at each occurrence, is selected from H, $CF_3$, $C_{1-6}$ alkyl, benzyl, $C_{3-6}$ carbocyclic residue substituted with 0–2 $R^{4b}$, a $C_{3-6}$ carbocyclic-$CH_2$— residue substituted with 0–2 $R^{4b}$, and 5–6 membered heterocyclic system containing from 1–4 heteroatoms selected from the group consisting of N, O, and S substituted with 0–2 $R^{4b}$;

$R^{2a}$, at each occurrence, is selected from H, $CF_3$, $C_{1-6}$ alkyl, benzyl, $C_{3-6}$ carbocyclic residue substituted with 0–2 $R^{4b}$, and 5–6 membered heterocyclic system containing from 1–4 heteroatoms selected from the group consisting of N, O, and S substituted with 0–2 $R^{4b}$;

$R^{2b}$, at each occurrence, is selected from $CF_3$, $C_{1-4}$ alkoxy, $C_{1-6}$ alkyl, benzyl, $C_{3-6}$ carbocyclic residue substituted with 0–2 $R^{4b}$, and 5–6 membered heterocyclic system containing from 1–4 heteroatoms selected from the group consisting of N, O, and S substituted with 0–2 $R^{4b}$;

$R^{2c}$, at each occurrence, is selected from $CF_3$, OH, $C_{1-4}$ alkoxy, $C_{1-6}$ alkyl, benzyl, $C_{3-6}$ carbocyclic residue substituted with 0–2 $R^{4b}$, and 5–6 membered heterocyclic system containing from 1–4 heteroatoms selected from the group consisting of N, O, and S substituted with 0–2 $R^{4b}$;

alternatively, $R^2$ and $R^{2a}$, together with the atom to which they are attached, combine to form a 5 or 6 membered saturated, partially saturated or unsaturated ring substituted with 0–2 $R^{4b}$ and containing from 0–1 additional heteroatoms selected from the group consisting of N, O, and S;

$R^3$, at each occurrence, is selected from H, $C_{1-4}$ alkyl, and phenyl;

$R^{3a}$, at each occurrence, is selected from H, $C_{1-4}$ alkyl, and phenyl;

$R^{3b}$, at each occurrence, is selected from H, $C_{1-4}$ alkyl, and phenyl;

$R^{3c}$, at each occurrence, is selected from $C_{1-4}$ alkyl, and phenyl;

$A^1$ is 2–5 membered linker substituted with 0–2 $R^4$ and selected from $C_{2-4}$ alkylene, $C_{2-4}$ alkenylene, $(CH_2)_uO(CH_2)_u$, $(CH_2)_uNH(CH_2)_u$, $(CH_2)_uC(O)(CH_2)_u$, $(CH_2)_uC(O)O(CH_2)_u$, $(CH_2)_uOC(O)(CH_2)_u$, $(CH_2)_uC(O)NH(CH_2)_u$, $(CH_2)_uNHC(O)(CH_2)_u$, $(CH_2)_uS(O)_p(CH_2)_u$, $(CH_2)_uSO_2NH(CH_2)_u$, and $(CH_2)_uNHSO_2(CH_2)_u$, provided that $A^1$ forms other than a N—O or N—S bond;

alternatively, the $CH_2$—$A^1$ group is replaced by a group selected from C=CH—NH, C=CH—O, and C=CH—S;

B is selected from:

X—Y, $NR^2R^{2a}$, $C(=NR^2)NR^2R^{2a}$, $NR^2C(=NR^2)NR^2R^{2a}$, $C_{3-10}$ carbocyclic residue substituted with 0–2 $R^{4a}$, and 5–10 membered heterocyclic system containing from 1–4 heteroatoms selected from the group consisting of N, O, and S substituted with 0–2 $R^{4a}$;

X is selected from $C_{1-4}$ alkylene, $—CR^2(CR^2R^{2b})(CH_2)_t—$, —C(O)—, $—C(=NR^{1d})—$, $—CR^2(NR^{1d}R^2)—$, $—CR^2(OR^2)—$, $—CR^2(SR^2)—$, $—C(O)CR^2R^{2a}—$, $—CR^2R^{2a}C(O)$, $—S(O)_p—$, $—S(O)_pCR^2R^{2a}—$, $—CR^2R^{2a}S(O)_p—$, $—S(O)_2NR^2—$, $—NR^2S(O)_2—$, $—NR^2S(O)_2CR^2R^{2a}—$, $—CR^2R^{2a}S(O)_2NR^2—$, $—NR^2S(O)_2NR^2—$, $—C(O)NR^2—$, $—NR^2C(O)—$, $—C(O)NR^2CR^2R^{2a}—$, $—NR^2C(O)CR^2R^{2a}—$, $—CR^2R^{2a}C(O)NR^2—$, $—CR^2R^{2a}NR^2C(O)—$, $—NR^2C(O)O—$, —OC(O)$NR^2—$, $—NR^2C(O)NR^2—$, $—NR^2$, $—NR^2CR^2R^{2a}—$, $—CR^2R^{2a}NR^2—$, O, $—CR^2R^{2a}O—$, and $—OCR^2R^{2a}—$;

Y is selected from:
  $(CH_2)_rNR^2R^{2a}$, provided that X—Y do not form a N—N, O—N, or S—N bond,
  $C_{3-10}$ carbocyclic residue substituted with 0–2 $R^{4a}$, and
  5–10 membered heterocyclic system containing from 1–4 heteroatoms selected from the group consisting of N, O, and S substituted with 0–2 $R^{4a}$;

$R^4$, at each occurrence, is selected from H, =O, $(CH_2)_rOR^2$, F, Cl, Br, I, $C_{1-4}$ alkyl, —CN, $NO_2$, $(CH_2)_rNR^2R^{2a}$, $(CH_2)_rC(O)R^{2c}$, $NR^2C(O)R^{2b}$, $C(O)NR^2R^{2a}$, NR²C(O)NR²R²ᵃ, CH(=NR²)NR²R²ᵃ, CH(=NS(O)₂ R⁵)NR²R²ᵃ, NHC(=NR²)NR²R²ᵃ, C(O)NHC(=NR²) NR²R²ᵃ, SO₂NR²R²ᵃ, NR²SO₂NR²R²ᵃ, NR²SO₂— C₁₋₄ alkyl, NR²SO₂R⁵, S(O)ₚR⁵, (CF₂)ᵣCF₃, NCH₂R¹ᵈ, OCH₂R¹ᵈ, SCH₂R¹ᵈ, N(CH₂)₂(CH₂)ₜ R¹ᶜ, O(CH₂)₂(CH₂)ᵣR¹ᶜ, and S(CH₂)₂(CH₂)ᵣR¹ᶜ;

R⁴ᵃ, at each occurrence, is selected from H, =O, (CH₂)ᵣ OR², (CH₂)ᵣ—F, (CH₂)ᵣ—Br, (CH₂)ᵣ—Cl, Cl, Br, F, I, C₁₋₄ alkyl, —CN, NO₂, (CH₂)ᵣNR²R²ᵃ, (CH₂)ᵣC(O) R²ᶜ, NR²C(O)R²ᵇ, C(O)NR²R²ᵃ, C(O)NH(CH₂)₂ NR²R²ᵃ, NR²C(O)NR²R²ᵃ, CH(=NR²)NR²R²ᵃ, NHC (=NR²)NR²R²ᵃ, SO₂NR²R²ᵃ, NR²SO₂NR²R²ᵃ, NR²SO₂—C₁₋₄ alkyl, C(O)NHSO₂—C₁₋₄ alkyl, NR²SO₂R⁵, S(O)ₚR⁵, and (CF₂)ᵣCF₃;

alternatively, one R⁴ᵃ is a 5–6 membered aromatic heterocycle containing from 1–4 heteroatoms selected from the group consisting of N, O, and S substituted with 0–1 R⁵;

R⁴ᵇ, at each occurrence, is selected from H, =O, (CH₂)ᵣ OR³, F, Cl, Br, I, C₁₋₄ alkyl, —CN, NO₂, (CH₂)ᵣ NR³R³ᵃ, (CH₂)ᵣC(O)R³, (CH₂)ᵣC(O)OR³ᶜ, NR³C(O) R³ᵃ, C(O)NR³R³ᵃ, NR³C(O)NR³R³ᵃ, CH(=NR³) NR³R³ᵃ, NR³C(=NR³)NR³R³ᵃ, SO₂NR³R³ᵃ, NR³SO₂NR³R³ᵃ, NR³SO₂—C₁₋₄ alkyl, NR³SO₂CF₃, NR³SO₂-phenyl, S(O)ₚCF₃, S(O)ₚ—C₁₋₄ alkyl, S(O)ₚ-phenyl, and (CF₂)ᵣCF₃;

R⁵, at each occurrence, is selected from CF₃, C₁₋₆ alkyl, phenyl substituted with 0–2 R⁶, and benzyl substituted with 0–2 R⁶;

R⁶, at each occurrence, is selected from H, OH, (CH₂)ᵣ OR², halo, C₁₋₄ alkyl, CN, NO₂, (CH₂)ᵣNR²R²ᵃ, (CH₂)ᵣ C(O)R²ᵇ, NR²C(O)R²ᵇ, NR²C(O)NR²R²ᵃ, CH(=NH)NH₂, NHC(=NH)NH₂, SO₂NR²R²ᵃ, NR²SO₂NR²R²ᵃ, and NR²SO₂C₁₋₄ alkyl;

R⁷, at each occurrence, is selected from H, OH, C₁₋₆ alkyl, C₁₋₆ alkylcarbonyl, C₁₋₆ alkoxy, C₁₋₄ alkoxycarbonyl, (CH₂)ₙ-phenyl, C₆₋₁₀ aryloxy, C₆₋₁₀ aryloxycarbonyl, C₆₋₁₀ arylmethylcarbonyl, C₁₋₄ alkylcarbonyloxy C₁₋₄ alkoxycarbonyl, C₆₋₁₀ arylcarbonyloxy C₁₋₄ alkoxycarbonyl, C₁₋₆ alkylaminocarbonyl, phenylaminocarbonyl, and phenyl C₁₋₄ alkoxycarbonyl;

R⁸, at each occurrence, is selected from H, C₁₋₆ alkyl and (CH₂)ₙ-phenyl;

alternatively, R⁷ and R⁸ combine to form a 5 or 6 membered saturated, ring which contains from 0–1 additional heteroatoms selected from the group consisting of N, O, and S;

R⁹, at each occurrence, is selected from H, C₁₋₆ alkyl and (CH₂)ₙ-phenyl;

n, at each occurrence, is selected from 0, 1, 2, and 3;

p, at each occurrence, is selected from 0, 1, and 2;

r, at each occurrence, is selected from 0, 1, 2, and 3;

s, at each occurrence, is selected from 0, 1, and 2;

t, at each occurrence, is selected from 0, 1, 2, and 3; and, u, at each occurrence, is selected from 0, 1, 2, and 3.

2. A compound of formula B:

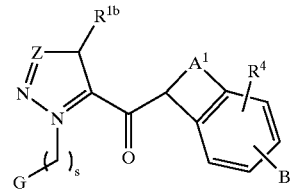

B or a stereoisomer or pharmaceutically acceptable salt thereof; wherein:

G is selected from the group:

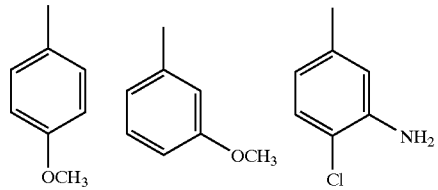

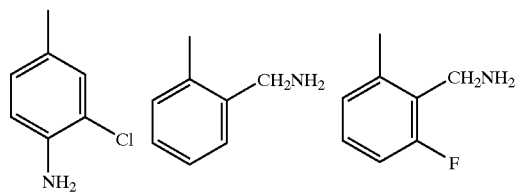

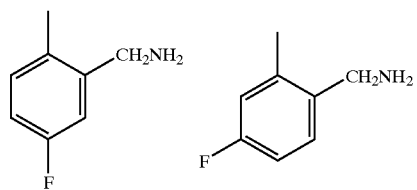

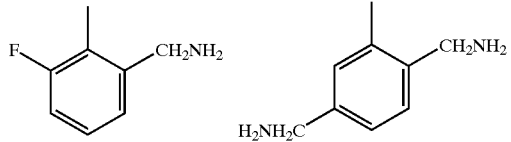

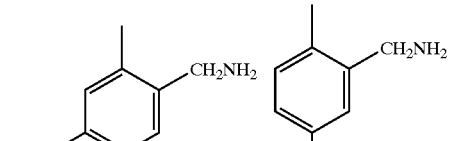

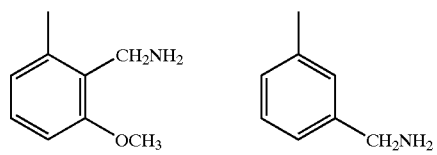

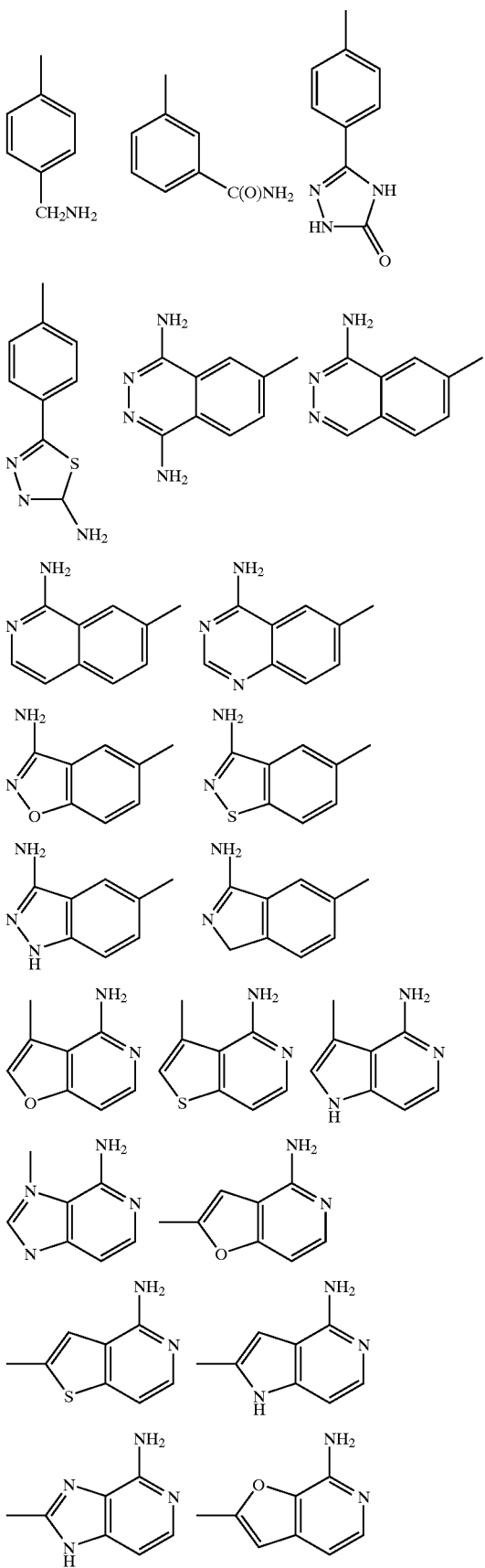

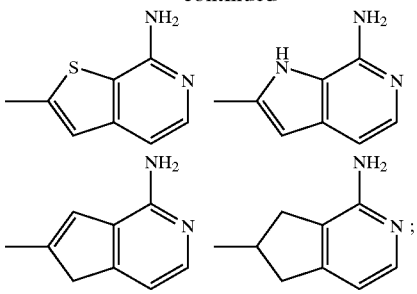

Z is N or CR$^{1a}$;

R$^{1a}$ is absent or selected from —(CH$_2$)$_r$—R$^{1c}$, —CH=CH—R$_{1c}$, NCH$_2$R$^{1d}$, OCH$_2$R$^{1d}$, SCH$_2$R$^{1d}$, NH(CH$_2$)$_2$(CH$_2$)$_2$R$^{1c}$, O(CH$_2$)$_2$(CH$_2$)$_r$R$^{1c}$, and S(CH$_2$)$_2$(CH$_2$,R$^{1c}$;

R$^{1b}$ is absent or selected from —(CH$_2$)$_r$—R$^{1c}$, —CH=CH—R$^{1c}$, NCH$_2$R$^{1d}$, OCH$_2$R$^{1d}$, SCH$_2$R$^{1d}$, NH(CH$_2$)$_2$(CH$_2$)$_r$R$^{1c}$, O(CH$_2$)$_2$(CH$_2$)$_r$R$^{1c}$, and S(CH$_2$)$_2$(CH$_2$)$_r$R$^{1c}$;

alternatively R$^{1a}$ and R$^{1b}$, when both are present, together with the atoms to which they are attached form a 5–8 membered saturated, partially saturated or unsaturated ring substituted with 0–2 R$^4$ and which contains from 0–2 heteroatoms selected from the group consisting of N, O, and S;

R$^{1c}$ is selected from H, C$_{1-3}$ alkyl F, Cl Br, I, —CN, —CHO, (CF$_2$)$_r$CF$_3$, (CH$_2$)$_r$OR$^2$, NR$^2$R$^{2a}$, C(O)R$^{2c}$, OC(O)R$^2$, (CF$_2$)$_r$CO$_2$R$^{2c}$, S(O)$_p$R$^{2b}$, NR$^2$(CH$_2$)$_r$OR$^2$, CH(=NR$^{2c}$)NR$^2$R$^{2a}$, NR$^2$C(O)R$^{2b}$, NR$^2$C(O)NHR$^{2b}$, NR$^2$C(O)$_2$R$^{2a}$, OC(O)NR$^{2a}$R$^{2b}$, C(O)NR$^2$R$^{2a}$, C(O)NR$^2$(CH$_2$)$_r$OR$^2$, SO$_2$NR$^2$R$^{2a}$, NR$^2$SO$_2$R$^{2b}$, C$_{3-6}$ carbocyclic residue substituted with 0–2 R$^4$, and 5–10 membered heterocycle system containing from 1–4 heteroatoms selected from the group consisting of N, O, and S substituted with 0–2 R$^4$;

R$^{1d}$ is selected from H, CH(CH$_2$OR$^2$)$_2$, C(O)R$^{2c}$, C(O)NR$^2$R$^{2a}$, S(O)R$^{2b}$, S(O)$_2$R$^{2b}$, and SO$_2$NR$^2$R$^{2a}$;

R$^2$ at each occurrence, is selected from H, CF$_3$, C$_{1-6}$ alkyl, benzyl, C$_{3-6}$ carbocyclic residue substituted with 0–2 R$^{4b}$, a C$_{3-6}$ carbocyclic —CH$_2$— residue substituted with 0–2 R$^{4b}$, and 5–6 membered heterocyclic system containing from 1–4 heteroatoms selected from the group consisting of N, O, and S substituted with 0–2 R$^{4b}$;

R$^{2a}$, at each occurrence, is selected from H, CF$_3$, C$^{1-6}$ alkyl, benzyl, C$_{3-6}$ carbocyclic residue substituted with 0–2 R$^{4b}$, and 5–6 membered heterocyclic system containing from 1–4 heteroatoms selected from the group consisting of N, O, and S substituted with 0–2 R$^{4b}$;

R$^{2b}$, at each occurrence, is selected from CF$_3$, C$_{1-4}$ alkoxy, C$_{1-6}$ alkyl, benzul C$_{3-6}$ carbocyclic residue substituted with 0–2 R$^{4b}$, and 5–6 membered heterocyclic system containing from 1–4 hetoroatoms selected from the group consisting of N, O, and S pubatltizted with 0–2 R$^{4b}$;

R$^{2c}$, at each occurrence, is selected from CF$_3$, OH, C$_{1-4}$ alkoxy C$_{1-6}$ alkyl, benzyl, C$_{3-6}$ carbocyclic residue substituted with 0–2 R$^{4b}$, and 5–6 membered heterocyclic system containing from 1–4 heteroatoms selected from the group consisting of N, O, and S substituted with 0–2 R$^{4b}$;

alternatively, R² and R²ᵃ, tonether with the atom to which they are attached, combine to form a 5 or 6 membered saturated, partially saturated or unsaturated ring substituted with 0–2 R⁴ᵇ and containing from 0–1 addItional heteroatoms selected from the group consisting of N, O, and S;

R³, at each occurrence. is selected from H, C₁₋₄ alkyl, and phenyl;

R³ᵃ, at each occurrence, is selected from H, C₁₋₄ alkyl, and phenyl; R³ᵇ, at each occurrence, is selected from H, C₁₋₄ alkyl and phenyl;

R³ᶜ, at each occurrence, is selected from C₁₋₄ alkyl, and phenyl;

A₁ is 3–5 membered linker substituted with 0–2 R⁴ and selected from C₂₋₄ alkylene, (CH₂)ᵤO(CH₂)ᵤ, (CH₂)ᵤNH(CH₂)ᵤ, (CH₂)ᵤC(O)(CH₂)ᵤ, (CH₂)ᵤC(O)O(CH₂)ᵤ, (CH₂)ᵤOC(O)(CH₂)ᵤ, (CH₂)ᵤC(O)NH(CH₂)ᵤ, (CH₂)ᵤNHC(O)(CH₂)ᵤ, (CH₂)ᵤS(O)ₚ(CH₂)ᵤ, (CH₂)ᵤSO₂NH(CH₂)ᵤ, and (CH₂)ᵤNHSO₂(CH₂)ᵤ, provided that A¹ forms other than a N—O or N—S bond;

alternatively, the CH₂—A¹ group is replaced by a group selected from C=CH—NH and C=CH—O;

B is selected from: H, Y, X—Y;

X is selected from C₁₋₄ alkylene, —C(O)—, —C(=NR¹ᵈ)—, —CR²(NR²R²ᵃ)—, —C(O)CR²R²ᵃ—, —CR²ᵃC(O), —C(O)NR²—, —NR²C(O)—, —C(O)NR²CR²R²ᵃ—, —NR²C(O)CR²R²ᵃ—, —CR²R²ᵃC(O)NR²—, —CR²R²ᵃNR²C(O)—, —NR²C(O)NR²—, —NR²—, —NR²CR²R²ᵃ—, —CR²R²ᵃNR²—, O, —CR²R²ᵃO—, and —OCR²R²ᵃ—;

Y is NR²R²ᵃ, provided that X—Y do not form a N—N or O—N bond;

alternatively, Y is selected from one of the following carbocyclic and heterocyclic systems which are substituted with 0–2 R⁴ᵃ;

cyclopropyl, cyclopentyl, cyclohexyl, phenyl, piperidinyl, piperazinyl, pyridyl, pyrimidyl, furanyl, morpholinyl, thiophenyl, pyrrolyl, pyrrolidinyl, oxazolyl, isoxazolyl, isoxazolinyl, thiazolyl, isothiazolyl, pyrazolyl, imidazolyl, oxadiazolyl, thiadiazolyl, triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolyl, benzimidazolyl, benzoxazolyl, benzthiazolyl, indazolyl, benzisoxazolyl, benzisothiazolyl, and isoindazolyl;

alternatively, Y is selected from the following bicyclic heteroaryl ring systems:

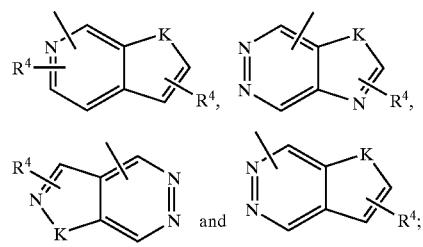

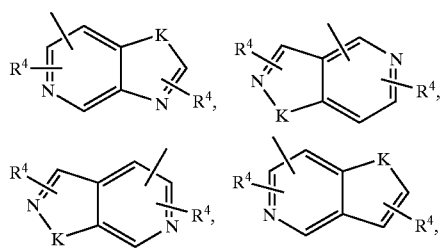

K is selected from O, S, NH, and N;

R₄, at each occurrence, is selected from H, =O, (CH₂)ᵣOR², F, Cl, Br, I, C₁₋₄ alkyl, —CN, NO₂, (CH₂)ᵣNR²R²ᵃ, (CH₂)ᵣC(O)R²ᶜ, NR²C(O)R²ᵇ, C(O)NR²R²ᵃ, NR²C(O)NR²R²ᵃ, CH(=NR²)NR²R²ᵃ, CH(=NS(O)₂R⁵)NR²R²ᵃNHC(=NR²)NR²ᴿ²ᵃ, C(O)NHC(=NR²)NR²R²ᵃ, SO₂NR²R²ᵃ, NR²SO₂NR²R²ᵃ, NR²SO₂—C₁₋₄ alkyl, NR²SO₂R⁵, S(O)ₚR⁵, (CF₂)ᵣCF₃, NCH₂R¹ᵈ, OCH₂R¹ᵈ, SCH₂R¹ᵈ, N(CH₂)₂(CH₂)ᵣR¹ᶜ, O(CH₂)₂(CH₂)ᵣR¹ᶜ, and S(CH₂)₂(CH₂)ᵣR¹ᶜ;

R⁴ᵃ, at each occurrence, is selected from H, =O, (CH₂)ᵣOR², (CH₂)ᵣ—F, (CH₂)ᵣ—Br, (CH₂)ᵣ—Cl, Cl, Br, F, I, C₁₋₄ alkyl, —CN, NO₂, (CH₂)ᵣNR²R²ᵃ, (CH₂)ᵣC(O)R²ᶜ, NR²C(O)R²ᵇ, C(O)NR²R²ᵃ, C(O)NH(CH₂)₂NR²R²ᵃ, NR²C(O)NR²R²ᵃ, CH(=NR²)NR²R²ᵃ, NHC(=NR²)NR²R²ᵃ, SO₂NR²R²ᵃ, NR²SO₂NR²R²ᵃ, NR²SO₂—C₁₋₄ alkyl, C(O)NHSO₂—C₁₋₄ alkyl, NR²SO₂R⁵, S(O)ₚR⁵, and (CF₂)ᵣCF₃;

altertiatively. one R⁴ᵃ is a 5–6 membered aromatic heterocycle containing from 1–4 heteroatoms selected from the group consisting of N, O, and S substituted with 0–1 R⁵;

R⁴ᵇ, at each occurrence, is selected from H, =O, (CH₂)ᵣOR³, F, Cl, Br, I, C₁₋₄ alkyl, —CN, NO₂, (CH₂)ᵣNR³R³ᵃ, (CH₂)ᵣC(O)R³, (CH₂)ᵣC(O)OR³ᶜ, NR³C(O)R³ᵃ, C(O)NR³ᴿ³ᵃ, NR³C(O)NR³R³ᵃ, CH(=NR³)NR³R³ᵃ, NR³C(=NR³)NR³R³ᵃ, SO₂NR³R³ᵃ, NR³SO₂NR³R³ᵃ, NR³SO₂—C₁₋₄ alkyl, NR³SO₂CF₃, NR³SO₂-phenyl, S(O)NR³SO_pCFNR³SO₃, S(O)NR³SO_pC₁₋₄ alkyl, S(O)NR³SO_p-phenyl, and (CF₂)ᵣCF₃;

R⁵, at each occurrence, is selected from CF₃, C₁₋₆ alkyl, phenyl substituted with 0–2 R⁶, and benzyl substituted wIth 0–2 R⁶;

R⁶, at each occurrence, is selected from H, OH, (CH₂)ᵣOR², halo, C₁₋₄ alkyl, CN, NO₂, (CH₂)ᵣNR²R²ᵃ, (CH₂)ᵣ C(O)R²ᵇ, NR²C(O)R²ᵇ, NR²C(O)NR²R²ᵃ, CH(=NH₂, NHC(=NH)NH₂, SO₂NR²R²ᵃ, NR²SO₂NR²R²ᵃ, and NR²SO₂C₁₋₄ alkyl;

p, at each occurrence, is selected from 0,1, and 2;

r, at each occurrence is selected from 0, 1, 2, and 3;

s is 0;

t, at each occurrence, is selected from 0, 1, 2, and 3; and u, at each occurrence, is selected from 0, 1, 2, and 3.

3. A compound according to claim 2, wherein:

G is selected from the group:

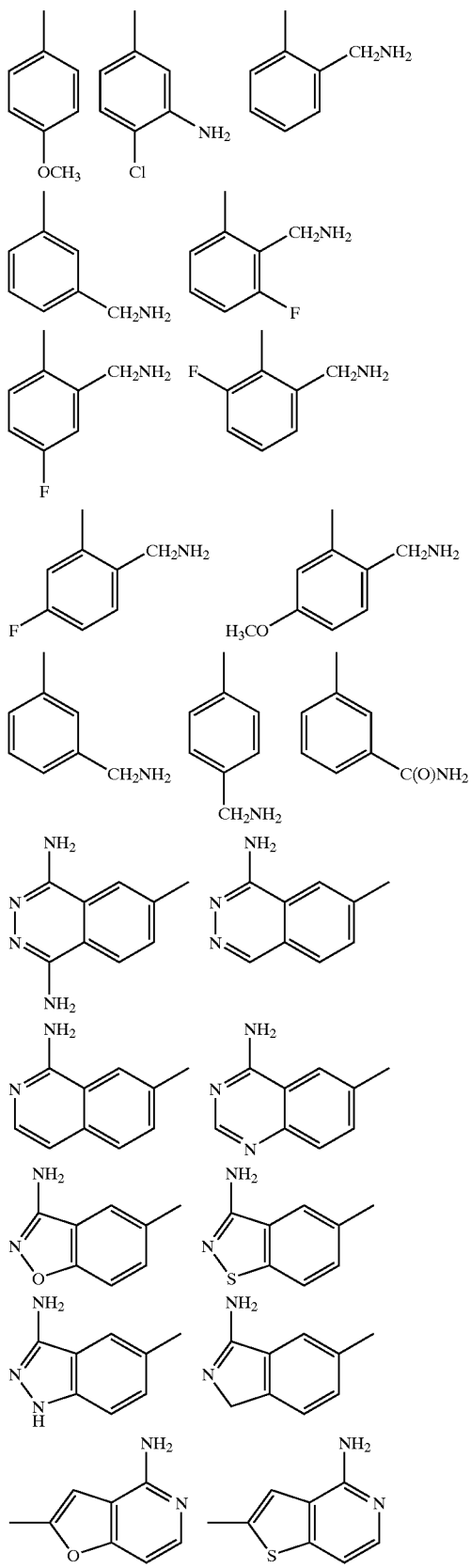

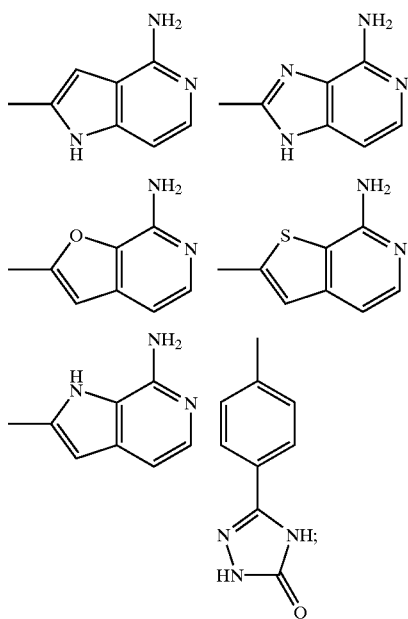

$A^1$ is 3–5 membered linker substituted with 0–2 $R^4$ and selected from $C_{2-4}$ alkylene, $(CH_2)_uO(CH_2)_u$, $(CH_2)_u NH(CH_2)_u$, $(CH_2)_uC(O)(CH_2)_u$, $(CH_2)_uC(O)NH(CH_2)_u$, $(CH_2)_uNHC(O)(CH_2)_u$, $(CH_2)_u SO_2NH(CH_2)_u$, and $(CH_2)_uNHSO_2(CH_2)_u$, provided that $A^1$ forms other than a N—O or N—S bond; and alternatively, the $CH_2$—$A^1$ group is replaced by a group selected from C=CH—NH and C=CH—O.

4. A compound according to claim 3, wherein:

G is selected from:

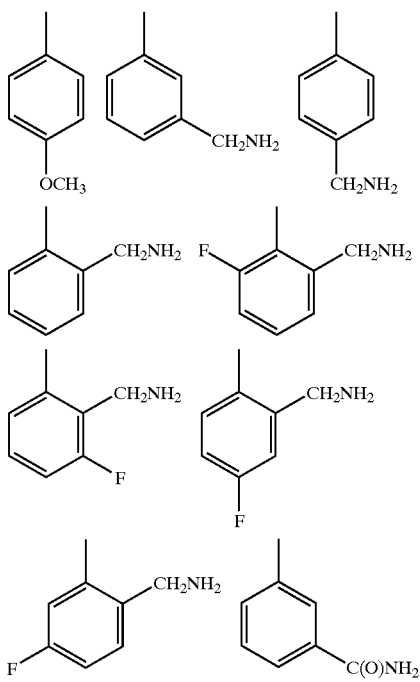

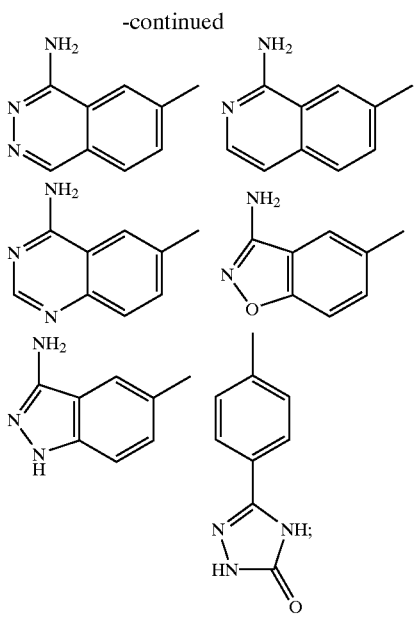

$A^1$ is 3–5 membered linker substituted with 0–2 $R^4$ and selected from $C_{2-4}$ alkylene, $(CH_2)_uO(CH_2)_u$, $(CH_2)_uNH(CH_2)_u$, $(CH_2)_uC(O)(CH_2)_u$, $(CH_2)_uC(O)NH(CH_2)_u$, $(CH_2)_uNHC(O)(CH_2)_u$, $(CH_2)_uSO_2NH(CH_2)_u$, and $(CH_2)_uNHSO_2(CH_2)_u$, provided that $A^1$ forms other than a N—O or N—S bond; and alternatively, the $CH_2$—$A^1$ group is replaced by a group selected from C=CH—NH and C=CH—O.

5. A compound according to claim 4, wherein:

B is selected from X—Y, phenyl, pyrrolidino, morpholino, 1,2,3-triazolyl, and imidazolyl, and is substituted with 0–1 $R^{4a}$;

$R^2$, at each occurrence, is selected from H, $CH_3$, $CH_2CH_3$, cyclopropylmethyl, cyclobutyl, and cyclopentyl;

$R^{2a}$, at each occurrence, is H or $CH_3$;

alternatively, $R^2$ and $R^{2a}$, together with the atom to which they are attached, combine to form pyrrolidine substituted with 0–2 $R^{4b}$;

$R^4$, at each occurrence, is selected from OH, $(CH_2)_rOR^2$, halo, $C_{1-4}$ alkyl, $(CH_2)_rNR^2R^{2a}$, and $(CF_2)_rCF_3$;

$R^{4a}$ is selected from $C_{1-4}$ alkyl, $CF_3$, $(CH_2)_rNR^2R^{2a}$, $S(O)_pR^5$, $SO_2NR^2R^{2a}$, and 1-$CF_3$-tetrazol-2-yl;

$R^{4b}$, at each occurrence, is selected from H, $CH_3$, and OH;

$R^5$, at each occurrence, is selected from $CF_3$, $C_{1-6}$ alkyl, phenyl, and benzyl;

$A^1$ is 3–5 membered linker substituted with 0–2 $R^4$ and selected from $C_{2-4}$ alkylene, $(CH_2)_uO(CH_2)_u$, $(CH_2)_uNH(CH_2)_u$, $(CH_2)_uC(O)(CH_2)_u$, $(CH_2)_uC(O)NH(CH_2)_u$, $(CH_2)_uNHC(O)(CH_2)_u$, $(CH_2)_uSO_2NH(CH_2)_u$, and $(CH_2)_uNHSO_2(CH_2)_u$, provided that $A^1$ forms other than a N—O or N—S bond;

alternatively, the $CH_2$—$A^1$ group is replaced by a group selected from C=CH—NH and C=CH—O.

X is $CH_2$ or C(O);

Y is selected from pyrrolidino and morpholino; and r, at each occurrence, is selected from 0, 1, and 2.

6. A compound according to claim 5, wherein:

B is selected from the group: 2-(aminosulfonyl)phenyl, 2-(methylaminosulfonyl)phenyl, 1-pyrrolidinocarbonyl, 2-(methylsulfonyl)phenyl, 2-(N,N-dimethylaminomethyl)phenyl, 2-(N-pyrrolidinylmethyl)phenyl, 1-methyl-2-imidazolyl, 2-methyl-1-imidazolyl, 2-(dimethylaminomethyl)-1-imidazolyl, 2-(N-(cyclopropylmethyl)aminomethyl) phenyl, 2-(N-(cyclobutyl)aminomethyl)phenyl, 2-(N-(cyclopentyl)aminomethyl)phenyl, and 2-(N-(3-hydroxypyrrolidinyl)methyl)phenyl.

7. A pharmaceutical compositions, comprising: a pharmaceutically acceptable carrier and a therapeutically effective amount of a compound of claim 1 or a pharmaceutically acceptable salt form thereof.

8. A method for treating or preventing a thromboembolic disorder, comprising; administering to a patient in need thereof a therapeutically effective amount of a compound of claim 1 or a phaimaceutically acceptable salt form thereof.

9. A pharmaceutical compositions, comprising: a pharmaceutically acceptable carrier and a therapeutically effective amount of a compound of claim 2 or a pharmaceutically acceptable salt form thereof.

10. A pharmaceutical compositions, comprising: a pharmaceutically acceptable carrier anda therapeutically effective amount of a compound of claim 3 or a pharmaceutically acceptable salt form thereof.

11. A pharmaceutical compositions, comprising: a pharmaceutically acceptable carrier and a therapeutically effective amount of a compound of claim 4 or a pharmaceutically acceptable salt form thereof.

12. A pharmaceutical compositions, comprising: a pharmaceutically acceptable carrier and a therapeutically effective amount of a compound of claim 5 or a pharmaceutically acceptable salt form thereof.

13. A pharmaceutical compositions, comprising: a pharmaceutically acceptable carrier and a therapeutically effective amount of a compound of claim 6 or a pharmaceutically acceptable salt form thereof.

14. A method for treating or preventing a tbromboembolic disorder, comprising: administering to a patient in need thereof a therapeutically effective amount of a compound of claim 2 or a pharmaceutically acceptable salt form thereof.

15. A method for treating or preventing a thromboembolic disorder, comprising: administering to a patient in need thereof a therapeutically effective amount of a compound of claim 3 or a pharmaceutically acceptable salt form thereof.

16. A method for treating or preventing a thromboembolic disorder, comprising: administering to a patient in need thereof a therapeutically effective amount of a compound of claim 4 or a pharmaceutically acceptable salt form thereof.

17. A method for treating or preventing a thromboembolic disorder, comprising: administering to a patient in need thereof a therapeutically effective amount of a compound of claim 5 or a pharmaceutically acceptable salt form thereof.

18. A method for treating or preventing a thromboembolic disorder, comprising: administering to a patient in need thereof a therapeutically effective amount of a compound of claim 6 or a pharmaceutically acceptable salt form thereof.

* * * * *